United States Patent
Geall

(10) Patent No.: US 11,666,534 B2
(45) Date of Patent: *Jun. 6, 2023

(54) METHODS OF ADMINISTERING LIPID FORMULATIONS WITH VIRAL IMMUNOGENS

(71) Applicant: GLAXOSMITHKLINE BIOLOGICALS SA, Rixensart (BE)

(72) Inventor: Andrew Geall, Littleton, MA (US)

(73) Assignee: GlaxoSmithKline Biologicals SA, Rixensart (BE)

(*) Notice: Subject to any disclaimer, the term of this patent is extended or adjusted under 35 U.S.C. 154(b) by 0 days.

This patent is subject to a terminal disclaimer.

(21) Appl. No.: 17/560,138

(22) Filed: Dec. 22, 2021

(65) Prior Publication Data

US 2022/0125727 A1 Apr. 28, 2022

Related U.S. Application Data

(62) Division of application No. 13/808,080, filed as application No. PCT/US2011/043105 on Jul. 6, 2011.

(60) Provisional application No. 61/378,837, filed on Aug. 31, 2010, provisional application No. 61/361,830, filed on Jul. 6, 2010.

(51) Int. Cl.
| | | |
|---|---|---|
| *A61K 48/00* | (2006.01) | |
| *A61K 9/127* | (2006.01) | |
| *A61K 39/12* | (2006.01) | |
| *C12N 15/86* | (2006.01) | |
| *A61K 31/7088* | (2006.01) | |
| *A61K 39/00* | (2006.01) | |
| *A61K 39/39* | (2006.01) | |

(52) U.S. Cl.
CPC ............ *A61K 9/127* (2013.01); *A61K 9/1272* (2013.01); *A61K 31/7088* (2013.01); *A61K 39/00* (2013.01); *A61K 39/12* (2013.01); *C12N 15/86* (2013.01); *A61K 39/39* (2013.01); *A61K 2039/53* (2013.01); *A61K 2039/55555* (2013.01); *C12N 2710/16134* (2013.01); *C12N 2760/18534* (2013.01); *C12N 2770/36134* (2013.01)

(58) Field of Classification Search
None
See application file for complete search history.

(56) References Cited

U.S. PATENT DOCUMENTS

| | | | |
|---|---|---|---|
| 5,013,556 A | 5/1991 | Woodle et al. | |
| 5,279,833 A | 1/1994 | Rose | |
| 5,459,127 A | 10/1995 | Felgner et al. | |
| 5,474,914 A | 12/1995 | Spaete | |
| 5,750,390 A | 5/1998 | Thompson et al. | |
| 5,814,482 A | 9/1998 | Dubensky, Jr. et al. | |
| 5,843,723 A | 12/1998 | Dubensky, Jr. | |
| 5,885,613 A * | 3/1999 | Holland | A61K 9/1272 |
| | | | 428/402.2 |
| 5,965,434 A | 10/1999 | Wolff et al. | |
| 5,972,704 A | 10/1999 | Draper et al. | |
| 6,009,406 A | 12/1999 | Nick | |
| 6,015,686 A | 1/2000 | Dubensky et al. | |
| 6,048,546 A | 4/2000 | Sasaki et al. | |
| 6,060,308 A | 5/2000 | Parrington | |
| 6,090,406 A | 7/2000 | Popescu et al. | |
| 6,156,558 A | 12/2000 | Johnston et al. | |
| 6,395,302 B1 | 5/2002 | Hennink et al. | |
| 6,432,925 B1 | 8/2002 | Hoon et al. | |
| 6,602,705 B1 | 8/2003 | Barnett et al. | |
| 6,610,321 B2 | 8/2003 | Huang et al. | |
| 6,790,449 B2 | 9/2004 | Collins | |
| 6,815,432 B2 | 11/2004 | Wheeler et al. | |
| 6,858,225 B2 | 2/2005 | Semple et al. | |
| 6,890,554 B2 | 5/2005 | Jessee et al. | |
| 7,250,404 B2 | 7/2007 | Feigner et al. | |
| 7,303,881 B2 | 12/2007 | Huang et al. | |
| 7,384,923 B2 | 6/2008 | Gregoriadis | |
| 7,422,902 B1 | 9/2008 | Wheeler et al. | |
| 7,442,381 B2 | 10/2008 | Smith et al. | |
| 7,557,200 B2 | 7/2009 | Wu et al. | |
| 7,604,803 B2 | 10/2009 | Bacon et al. | |
| 7,691,405 B2 | 4/2010 | Chen et al. | |
| 7,745,651 B2 | 6/2010 | Heyes et al. | |
| 7,799,565 B2 | 9/2010 | MacLachlan et al. | |
| 7,811,812 B2 | 10/2010 | Dubensky et al. | |
| 7,862,829 B2 | 1/2011 | Johnston et al. | |
| 7,977,091 B2 | 7/2011 | Dubensky et al. | |
| 8,058,069 B2 | 11/2011 | Yaworski et al. | |

(Continued)

FOREIGN PATENT DOCUMENTS

| | | |
|---|---|---|
| BR | 112013004879 | 4/2018 |
| BR | 112012001666-0 A2 | 9/2019 |

(Continued)

OTHER PUBLICATIONS

Soong et al. (BBA, 2007, 1805-1814) (Year: 2007).*

(Continued)

*Primary Examiner* — Arthur S Leonard
(74) *Attorney, Agent, or Firm* — Knobbe Martens Olson & Bear LLP

(57) ABSTRACT

RNA encoding an immunogen is delivered in a liposome for the purposes of immunisation. The liposome includes lipids which have a pKa in the range of 5.0 to 7.6 and, preferably, a tertiary amine. These liposomes can have essentially neutral surface charge at physiological pH and are effective for immunisation.

37 Claims, 12 Drawing Sheets

(56) References Cited

U.S. PATENT DOCUMENTS

| | | |
|---|---|---|
| 8,338,583 B2 | 12/2012 | Schulamit |
| 8,877,206 B2 | 11/2014 | Chen et al. |
| 9,254,265 B2 | 2/2016 | Geall et al. |
| 9,504,651 B2 | 11/2016 | MacLachlan et al. |
| 9,770,463 B2 | 9/2017 | Geall et al. |
| 9,801,897 B2 | 10/2017 | Geall et al. |
| 9,801,987 B2 | 10/2017 | Farnan et al. |
| 10,188,748 B2 | 1/2019 | Mulbe et al. |
| 10,487,332 B2 | 11/2019 | Geall |
| 10,532,067 B2 | 1/2020 | Geall et al. |
| 10,906,867 B2 | 2/2021 | Brito et al. |
| 11,026,964 B2 | 6/2021 | Geall et al. |
| 11,058,762 B2 | 7/2021 | Geall et al. |
| 11,078,237 B2 | 8/2021 | Franti et al. |
| 11,291,635 B2 | 4/2022 | Geall et al. |
| 11,291,682 B2 | 4/2022 | Geall et al. |
| 11,324,770 B2 | 5/2022 | Geall et al. |
| 2003/0091591 A1 | 5/2003 | Xiong et al. |
| 2003/0096397 A1 | 5/2003 | Schlesinger |
| 2003/0124134 A1 | 7/2003 | Edwards et al. |
| 2003/0138453 A1 | 7/2003 | O'Hagan et al. |
| 2003/0203865 A1* | 10/2003 | Harvie .................. A61P 29/00 435/458 |
| 2003/0212022 A1 | 11/2003 | Vogel et al. |
| 2003/0232058 A1 | 12/2003 | Dubensky, Jr. |
| 2004/0142025 A1 | 7/2004 | MacLachlan |
| 2004/0208848 A1 | 10/2004 | Smith et al. |
| 2004/0228842 A1 | 11/2004 | Lu et al. |
| 2005/0032730 A1 | 2/2005 | von der Mulbe et al. |
| 2005/0042230 A1 | 2/2005 | Anderson et al. |
| 2005/0064026 A1 | 3/2005 | Garidel et al. |
| 2005/0064595 A1 | 3/2005 | MacLachlan et al. |
| 2005/0118566 A1 | 6/2005 | Escriou et al. |
| 2005/0266550 A1 | 12/2005 | Rayner et al. |
| 2006/0002991 A1 | 1/2006 | Essler et al. |
| 2006/0051405 A1 | 3/2006 | MacLachlan et al. |
| 2006/0063732 A1 | 3/2006 | Vogel et al. |
| 2006/0083780 A1 | 4/2006 | Heyes et al. |
| 2006/0177819 A1 | 8/2006 | Smith et al. |
| 2006/0240554 A1 | 10/2006 | Chen et al. |
| 2006/0251620 A1 | 11/2006 | Ivanova et al. |
| 2007/0014805 A1 | 1/2007 | Dalencon et al. |
| 2007/0118094 A1 | 5/2007 | Bingham et al. |
| 2007/0207526 A1 | 9/2007 | Coit |
| 2008/0057080 A1 | 3/2008 | Luke et al. |
| 2008/0085870 A1 | 4/2008 | Hermanson et al. |
| 2008/0187545 A1 | 8/2008 | Shenk et al. |
| 2008/0249046 A1 | 10/2008 | MacLachlan et al. |
| 2008/0260698 A1 | 10/2008 | Weaver |
| 2008/0311158 A1 | 12/2008 | Merola |
| 2009/0068221 A1 | 3/2009 | Morrison |
| 2009/0075384 A1 | 3/2009 | Kamrud |
| 2009/0104226 A1 | 4/2009 | Perri et al. |
| 2009/0143323 A1 | 6/2009 | Bavari |
| 2010/0040650 A1 | 2/2010 | Crowe et al. |
| 2010/0092481 A1 | 4/2010 | Lanzavecchia |
| 2010/0173980 A1 | 7/2010 | Valliant et al. |
| 2010/0196492 A1 | 8/2010 | Green et al. |
| 2010/0285112 A1 | 11/2010 | Novobrantseva |
| 2011/0053893 A1 | 3/2011 | Wu et al. |
| 2011/0070260 A1 | 3/2011 | Baric et al. |
| 2011/0076335 A1 | 3/2011 | Yaworski et al. |
| 2011/0117125 A1 | 5/2011 | Hope et al. |
| 2011/0200582 A1 | 8/2011 | Baryza |
| 2011/0200667 A1 | 8/2011 | Contreras et al. |
| 2011/0229969 A1 | 9/2011 | Sandig et al. |
| 2011/0244026 A1 | 10/2011 | Guild et al. |
| 2011/0300205 A1 | 12/2011 | Geall |
| 2011/0305727 A1 | 12/2011 | Swanson et al. |
| 2012/0030901 A1 | 2/2012 | Manninen et al. |
| 2012/0100207 A1 | 4/2012 | Motokui et al. |
| 2012/0156251 A1 | 6/2012 | Brito et al. |
| 2012/0177677 A1 | 7/2012 | Carmon |
| 2012/0195936 A1 | 8/2012 | Rudolph et al. |
| 2012/0237546 A1 | 9/2012 | Singh et al. |
| 2013/0101609 A1 | 4/2013 | O'Hagan et al. |
| 2013/0149375 A1 | 6/2013 | Geall |
| 2013/0164289 A1 | 6/2013 | McVoy et al. |
| 2013/0171185 A1 | 7/2013 | Settembre et al. |
| 2013/0171241 A1 | 7/2013 | Geall |
| 2013/0177639 A1 | 7/2013 | Geall et al. |
| 2013/0177640 A1 | 7/2013 | Geall et al. |
| 2013/0183355 A1 | 7/2013 | Jain et al. |
| 2013/0189351 A1 | 7/2013 | Geall |
| 2013/0195968 A1 | 8/2013 | Geall et al. |
| 2013/0195969 A1 | 8/2013 | Geall et al. |
| 2013/0202684 A1 | 8/2013 | Geall et al. |
| 2013/0225409 A1 | 8/2013 | Allen et al. |
| 2013/0245105 A1 | 9/2013 | De Fougerolles et al. |
| 2014/0030292 A1 | 1/2014 | Franti et al. |
| 2014/0044751 A1 | 2/2014 | Dormitzer |
| 2014/0141070 A1 | 5/2014 | Geall et al. |
| 2014/0193484 A1 | 7/2014 | Bertholet Girardin et al. |
| 2014/0212498 A1 | 7/2014 | Brito et al. |
| 2014/0220083 A1 | 8/2014 | Brito et al. |
| 2014/0227346 A1 | 8/2014 | Geall et al. |
| 2014/0242152 A1 | 8/2014 | Geall et al. |
| 2014/0248314 A1 | 9/2014 | Swanson et al. |
| 2014/0255472 A1 | 9/2014 | Geall |
| 2014/0271829 A1 | 9/2014 | Lilja et al. |
| 2014/0275227 A1 | 9/2014 | Hoge et al. |
| 2014/0303232 A1 | 10/2014 | Baryza et al. |
| 2014/0348863 A1 | 11/2014 | Bianchi et al. |
| 2015/0017251 A1 | 1/2015 | Malvala et al. |
| 2016/0024157 A1 | 1/2016 | Masignani et al. |
| 2016/0129105 A1 | 5/2016 | Mulbe et al. |
| 2018/0094033 A1 | 4/2018 | Telford et al. |
| 2019/0343862 A1 | 11/2019 | Geall |
| 2020/0048636 A1 | 2/2020 | Geall |
| 2020/0069793 A1 | 3/2020 | Ciaramella |
| 2020/0113830 A1 | 4/2020 | Geall et al. |
| 2020/0113831 A1 | 4/2020 | Geall et al. |
| 2020/0230058 A1 | 7/2020 | Geall et al. |
| 2020/0323896 A1 | 10/2020 | Geall |
| 2021/0290755 A1 | 8/2021 | Geall et al. |
| 2021/0268013 A1 | 9/2021 | Geall et al. |
| 2022/0054525 A1 | 2/2022 | Geall et al. |
| 2022/0056449 A1 | 2/2022 | Geall |
| 2022/0119455 A1 | 4/2022 | Franti et al. |
| 2022/0192997 A1 | 6/2022 | Geall et al. |
| 2022/0213149 A1 | 7/2022 | Franti et al. |

FOREIGN PATENT DOCUMENTS

| | | |
|---|---|---|
| EP | 0786522 A1 | 7/1997 |
| EP | 1083232 A1 | 3/2001 |
| EP | 0880360 | 10/2002 |
| EP | 1392341-81 | 3/2005 |
| EP | 1637144 A1 | 3/2006 |
| EP | 1764089 | 3/2007 |
| EP | 2338478 | 6/2011 |
| EP | 2510099 | 10/2012 |
| EP | 2578685 | 4/2013 |
| EP | 2791160 | 10/2014 |
| EP | 2590626 | 10/2015 |
| EP | 2591114 B1 | 6/2016 |
| EP | 2590676 B1 | 8/2016 |
| EP | 3336082 | 6/2018 |
| EP | 2750707 | 10/2018 |
| EP | 3318248 B1 | 4/2019 |
| EP | 3492109 | 6/2019 |
| EP | 2591103 B1 | 8/2019 |
| EP | 3611266 | 2/2020 |
| EP | 3682905 | 7/2020 |
| EP | 2729126 | 12/2020 |
| JP | 2000-505802 | 5/2000 |
| JP | 2001514857 A | 9/2001 |
| JP | 2007-112768 A1 | 5/2007 |
| JP | 2007-521247 | 8/2007 |
| JP | 2008501729 A | 1/2008 |
| JP | 2009-510097 | 3/2009 |
| JP | 2009-539845 | 11/2009 |
| JP | 2010-025644 | 2/2010 |
| JP | 2010-528591 | 8/2010 |

(56) References Cited

FOREIGN PATENT DOCUMENTS

| | | |
|---|---|---|
| JP | 2011-504802 | 2/2011 |
| WO | WO 1989/00812 | 2/1989 |
| WO | WO 1990/11092 | 10/1990 |
| WO | WO 1992/19752 | 11/1992 |
| WO | WO-1993024640 A2 | 12/1993 |
| WO | WO 1995/27721 | 10/1995 |
| WO | WO 1996/08235 | 3/1996 |
| WO | WO 1996/17072 | 6/1996 |
| WO | WO 1997/28818 | 8/1997 |
| WO | WO 1997/030170 | 8/1997 |
| WO | WO-1998010748 A1 | 3/1998 |
| WO | WO 1998/051278 | 11/1998 |
| WO | WO-1999011808 A1 | 3/1999 |
| WO | WO 1999/28487 | 6/1999 |
| WO | WO 1999/30733 | 6/1999 |
| WO | WO-1999052503 A2 | 10/1999 |
| WO | WO 1999/55310 | 11/1999 |
| WO | WO 2000/03683 | 1/2000 |
| WO | WO-2000000617 A2 | 1/2000 |
| WO | WO-2001029233 A2 | 4/2001 |
| WO | WO 2001/79253 A1 | 10/2001 |
| WO | WO 2001/93836 | 12/2001 |
| WO | WO-2002002606 A2 | 1/2002 |
| WO | WO-200209645 A2 | 2/2002 |
| WO | WO-2002026209 A2 | 4/2002 |
| WO | WO-2002034771 A2 | 5/2002 |
| WO | WO-2002061113 A2 | 8/2002 |
| WO | WO 2002/074920 | 9/2002 |
| WO | WO-2002072027 A2 | 9/2002 |
| WO | WO-2002079239 A2 | 10/2002 |
| WO | WO-2002095023 A2 | 11/2002 |
| WO | WO-2002098443 A2 | 12/2002 |
| WO | WO-2002026209 A3 | 1/2003 |
| WO | WO-2003018054 A1 | 3/2003 |
| WO | WO-2003068190 A1 | 8/2003 |
| WO | WO 2004/076645 | 9/2004 |
| WO | WO-2004098509 A2 | 11/2004 |
| WO | WO 2005/007689 | 1/2005 |
| WO | WO-2005002619 A2 | 1/2005 |
| WO | WO-2005032582 A2 | 4/2005 |
| WO | WO 2005/046621 | 5/2005 |
| WO | WO 2005/060934 | 7/2005 |
| WO | WO-2005111066 A2 | 11/2005 |
| WO | WO 2005/113781 | 12/2005 |
| WO | WO-2005113782 A1 | 12/2005 |
| WO | WO-2005120152 A2 | 12/2005 |
| WO | WO-2005121348 A1 | 12/2005 |
| WO | WO 2006/053646 | 5/2006 |
| WO | WO 2006/061643 | 6/2006 |
| WO | WO-2006078294 A2 | 7/2006 |
| WO | WO-2006089264 A2 | 8/2006 |
| WO | WO-2006091517 A2 | 8/2006 |
| WO | WO 2006/094756 | 9/2006 |
| WO | WO-2006092607 A1 | 9/2006 |
| WO | WO-2006110413 A2 | 10/2006 |
| WO | WO-2006138004 A2 | 12/2006 |
| WO | WO 2007/014754 | 2/2007 |
| WO | WO-2007024708 A2 | 3/2007 |
| WO | WO 2007/036366 | 4/2007 |
| WO | WO 2007/041270 | 4/2007 |
| WO | WO-2007047749 A1 | 4/2007 |
| WO | WO-2007049155 A2 | 5/2007 |
| WO | WO 2007107304 A2 | 9/2007 |
| WO | WO 2007/146024 | 12/2007 |
| WO | WO 2007/149518 | 12/2007 |
| WO | WO-2008020330 A2 | 2/2008 |
| WO | WO 2008/033966 | 3/2008 |
| WO | WO 2008/051245 | 5/2008 |
| WO | WO 2008/083949 | 7/2008 |
| WO | WO-2008103276 A2 | 8/2008 |
| WO | WO-2008137758 A2 | 11/2008 |
| WO | WO 2008/148068 | 12/2008 |
| WO | WO-2008155141 A2 | 12/2008 |
| WO | WO 2009/003975 | 1/2009 |
| WO | WO 2009/026328 | 2/2009 |
| WO | WO-2009016515 A2 | 2/2009 |
| WO | WO-2009031043 A2 | 3/2009 |
| WO | WO-2009040443 A1 * | 4/2009 ........... A61K 38/208 |
| WO | WO-2009042794 A2 | 4/2009 |
| WO | WO 2009/068485 | 6/2009 |
| WO | WO 2009/074861 | 6/2009 |
| WO | WO-2009079185 A2 | 6/2009 |
| WO | WO-2009086558 A1 | 7/2009 |
| WO | WO-2009104092 A2 | 8/2009 |
| WO | WO-2009109860 A2 | 9/2009 |
| WO | WO-2009111088 A2 | 9/2009 |
| WO | WO 2009/132131 | 10/2009 |
| WO | WO-2009127230 A1 | 10/2009 |
| WO | WO-2009132206 A1 | 10/2009 |
| WO | WO 2009/156852 | 12/2009 |
| WO | WO-2009146867 A1 | 12/2009 |
| WO | WO 2010/007463 | 1/2010 |
| WO | WO 2010/007533 | 1/2010 |
| WO | WO 2010/019718 | 2/2010 |
| WO | WO-2010015098 A1 | 2/2010 |
| WO | WO 2010/036948 | 4/2010 |
| WO | WO-2010042877 A1 | 4/2010 |
| WO | WO 2010/053572 | 5/2010 |
| WO | WO 2010/054401 | 5/2010 |
| WO | WO-2010059689 A2 | 5/2010 |
| WO | WO 2010/088537 | 8/2010 |
| WO | WO-2010119343 A2 | 10/2010 |
| WO | WO 2010/144740 | 12/2010 |
| WO | WO-2011001780 A1 | 1/2011 |
| WO | WO-2011005799 A2 | 1/2011 |
| WO | WO-2011008974 A2 | 1/2011 |
| WO | WO 2011/012316 | 2/2011 |
| WO | WO 2011/071931 | 6/2011 |
| WO | WO 2011/075656 | 6/2011 |
| WO | WO-2011068810 A | 6/2011 |
| WO | WO-2011071860 A2 | 6/2011 |
| WO | WO-2011076807 A2 | 6/2011 |
| WO | WO 2011/112717 | 9/2011 |
| WO | WO 2011/127316 | 10/2011 |
| WO | WO-2011140627 A1 | 11/2011 |
| WO | WO-2012006369 A2 | 1/2012 |
| WO | WO-2012006372 A1 | 1/2012 |
| WO | WO-2012006376 A2 | 1/2012 |
| WO | WO-2012006377 A2 | 1/2012 |
| WO | WO-2012006378 A1 | 1/2012 |
| WO | WO-2012006380 A2 | 1/2012 |
| WO | WO 2012/019168 | 2/2012 |
| WO | WO 2012/034025 | 3/2012 |
| WO | WO-2012030901 A1 | 3/2012 |
| WO | WO-2012031043 A2 | 3/2012 |
| WO | WO-2012031046 A1 | 3/2012 |
| WO | WO 2012/045075 | 4/2012 |
| WO | WO 2012/045082 | 4/2012 |
| WO | WO 2012/135805 | 10/2012 |
| WO | WO 2012/158736 | 11/2012 |
| WO | WO 2012/170889 | 12/2012 |
| WO | WO 2013/006825 | 1/2013 |
| WO | WO 2013/006837 | 1/2013 |
| WO | WO 2013/039861 | 3/2013 |
| WO | WO-2013033563 A1 | 3/2013 |
| WO | WO 2013/052523 | 4/2013 |
| WO | WO 2013/090648 | 6/2013 |
| WO | WO 2013/096709 | 6/2013 |
| WO | WO 2013/130161 | 9/2013 |
| WO | WO 2013/151663 | 10/2013 |
| WO | WO 2013/151664 | 10/2013 |
| WO | WO 2013/151665 | 10/2013 |
| WO | WO 2013/151666 | 10/2013 |
| WO | WO 2013/151667 | 10/2013 |
| WO | WO 2013/151668 | 10/2013 |
| WO | WO 2013/151669 | 10/2013 |
| WO | WO 2013/151670 | 10/2013 |
| WO | WO 2013/151671 | 10/2013 |
| WO | WO 2013/151672 | 10/2013 |
| WO | WO 2013/151736 | 10/2013 |
| WO | WO 2014/081507 | 5/2014 |
| WO | WO 2014/152211 | 9/2014 |
| WO | WO 2014/160243 | 10/2014 |
| WO | WO 2017/049245 | 3/2017 |

(56) References Cited

FOREIGN PATENT DOCUMENTS

| WO | WO 2017/075531 | 5/2017 |
|---|---|---|
| WO | WO 2018/089790 | 5/2018 |
| WO | WO 2020/106946 | 5/2020 |
| WO | WO 2021/038508 | 3/2021 |
| WO | WO 2022/137133 | 6/2022 |

OTHER PUBLICATIONS

Hofmann et al., (J Lip Res, 1984, 25:1477-1489) (Year: 1984).*
Schedin-Weiss et al. (Biochemistry, 2008, 47:13610-13619) (Year: 2008).*
Qa'Dan et al. (Infect & Immun, 2000, 68:2470-2474) (Year: 2000).*
U.S. Appl. No. 61/280,510, filed Nov. 4, 2009, Cullis et al.
U.S. Appl. No. 17/511,762, filed Oct. 27, 2021, Geall et al.
U.S. Appl. No. 17/512,248, filed Oct. 27, 2021, Geall.
"Encyclopedia Britannica" House Mouse; 2005.
"Pschyrembel, Klinisches Wörtenbuch" Immunisierung, Immunreaktion; 1997; pp. 747-748.
Aberle et al., "Humeral and Cellular Immune Response to RNA Immunization with Flavivirus Replicons Derived from Tick-Borne Encephalitis Virus". J Virol. (2005) 79(24):15107-15113.
Acheampong et al. "Ionization and transfection activity of n-methyl-substituted carbamoyl-cholesterol derivatives". J Biophys Chem. (2011) 2(2):53-62.
Anonymous, "Mengovirus", Wikipedia, (Apr. 25, 2020), pp. 1-2, URL: https://en.wikipedia.org/wiki/Mengovirus.
Atwood et al., "Comprehensive Supramolecular Chemistry II". Gen Prine SupraMol Chem Mol Recogn. pp. 141-143.
Babiuk et al., "Electroporation improves the efficacy of DNA vaccines in large animals". Vaccine 20(27-28):3399-3408.
Bagarazzi et al., "Immunotherapy against HPV16/18 generates potent TH1 and cytotoxic cellular immune responses", Scie Transl Med. (2012) 4(155):155ra138.
Bailey et al., "Modulation of membrane fusion by asymmetric transbilayer distributions of amino lipids". Biochemistry (1994) 33(42): 12573-12580.
Barai et al., "Production of highly purified RNA from yeast using calcium". Appl Biochem Microbiol. (1995) 31(5):421-424.
Birdi K.S., Handbook of Surface and Colloidal Chemistry, CRC Press, Inc. (1997).
Bogers, et al., "Macaques Primed with Self-Amplifying RNA Vaccines Expressing HIV-1 Envelope and Boosted with Recombinant Protein Show Potent T- and B-Cell Responses" poster at the AIDS Vaccine 2012 meeting; Sep. 9-12, 2012; Boston, MA USA.
Bogers et al., "Potent Immune Responses in Rhesus Macaques Induced by Nonviral Delivery of a Self-amplifying RNA Vaccines Expressing HIV Type 1 Envelope With a Cationic Nanoemulsion". J Infect Dis. (2015) 211:947-955.
Boxus et al., "DNA immunization with plasmids encoding fusion and nucleocapsid proteins of bovine respiratory synctial virus induces a strong cell-mediated immunity and protects calves against challeng", J Virol. (2007)81 (13):6879-6889.
Bramwell et al., "The rational design of vaccines". Drug Discov Today (2005) 10(22):1527-1534.
Bringmann et al., "RNA Vaccines in Cancer Treatment". J Biomed Biotech. (2010) 2010: 12 pages.
Brito et al., "A Cationic Nanoemulsion for the Delivery of Next-generation RNA Vaccines". J Am Soc Gene Cell Thera. (2014) 22:2118-2129.
Brito et al. "Self-Amplifying mRNA Vaccines". Advances Gene. (2014) 89:179-233.
Broz et al., "Newly described pattern recognition receptors team up against intracellular pathogens". Nat Rev Immunol. (2013) 13(8):551-565.
Buyens et al., "Elucidating the encapsulation of short interfering RNA in PEGylated cationic liposomes". Langmuir (2009) 25:4886-4891.

Buza et al., "CD14+ cells are required for IL-12 response in bovine blood mononuclear cells activated with Toll-like receptor (TLR) 7 and TLR8 ligands". Vet Immunol Immunopath. (2008) 126(3-4):273-282.
Cannon et al., "RNA Based Vaccines", DNA Cell Biol. (2002) 21(12): 953-961.
Caplen N.J., "Nucleic acid transfer using cationic lipids". In Kmiec E.B. (Eds) Gene Targeting Protocols. Methods in Mole. Biol., (2000) 133:1-19.
Carralot et al., "Polarization of immunity induced by direct injection of naked sequence-stabilized mRNA vaccines". Cell Mole Life Sci. (2004) 61 (18):2418-2424.
Chambers et al., "Vaccination of mice and cattle with plasmid DNA encoding the *Mycobacterium bovis* antigent MPB83". Clin Infect Dis. (2000) 30(3):S283-S287.

Cheng et al., "Enhancement of Sindbis virus self-replicating RNA vaccine potency by linkage of *Mycobacterium tuberculosis* heat shock protein 70 gene to an antigen gene". J Immunol. 166(10):6218-6226, 2001.

Cheng et al, "Enhancement of Sindbis Virus Self-Replicating RNA Vaccine Potency by Linkage of Herpes Simplex Virus Type 1 VP22 Protein to Antigen". J Viral. (2001) 75(5): 2368-2376.

Chiaramoni et al., "Liposome/DNA systems: correlation between hydrophobicity and DNA conformational change". J Biol Phys (2008) 34:179-188.

Chrai, et al. "Liposomes: A Review Part I: Manufacturing Issues", (Apr.), Biotech Trends, Pharma. Technology, (2001), pp. 28-34.

Conry et al., "Characterization of a Messenger RNA Polynucleotide Vaccine Vector". Cancer Res. (1995) 55:1397-1400.

Cox et al., "Bovine herpesvirus 1: immune responses in mice and cattle injected with plasmid DNA". J Virol. (1993) 67(9):5664-5667.

Crooke Stanley T., Antisense Drug Technology: Principles, Strategies, and Applications, 2nd ed., (2008), Chapter 9, "Liposomal Formulations for Nucleic Acid Delivery", pp. 237-270.

Cui et al., "DNA Vaccine". Adv Genetics (2005) 54:257-289.

Cavagna et al., "The National Park of the Casentine Forests", 2003, article "7—The Signs and Work of Man",(2003) p. 175.

Davis et al., "DNA vaccine for hepatitis B Evidence for immunogenicity in chimpanzees and comparison with other vaccines". Proc Natl Acad Sci USA (1996) 93:7213-7218.

Deering et al., "Nucleic acid vaccines: prospects for non-viral delivery of mRNA vaccines". Exp Opin Drug Deliv. (2014) 11(6):885-899.

Diebold et al., "Innate Antiviral Responses by Means ofTLR7-Mediated Recognition of Single-Stranded RNA". Science (2004) 303(5663):1529-1531.

Dupuis et al., "Dendritic cells internalize vaccine adjuvant after intramuscular injection". Cellular Immunol. (1998) 186(1):18-27.

Dupuis et al., "Distribution of DNA vaccines determines their immunogenicity after intramuscular injection in mice". J Immunol. (2000) 165(5):2850-2858.

El Ouahabi et al., "Double long-chain amidine liposome-mediated self replicating RNA transfection", FEBS Letters, (1996) 380(1-2): 108-112.

Elbashir et al., Duplexes of 21-nucleotide RNAs mediate RNA interference in cultured mammalian ceils. Nature (2001) 411 (6836): 494-498.

Evers et al., "State-of-the-Art Design and Rapid-Mixing Production Techniques of Lipid Nanoparticles for Nucleic Acid Delivery". Smail Methods (2018) 2(9):1700375.

Excerpt from "Comprehensive Supermolecuiar Chemistry II" 2017; vol. 1, Elsevier Ltd.

Felgner et al., "Lipofection: A Highly Efficient, Lipid-Mediated DNA-Transfection Procedure". Proc Natl Acad Sci USA (1987) 84:7413-7417.

Fenske et al., "Liposomal Nanomedicines: An Emerging Field", Toxicol Pathol. (2008) 36(1):21-29.

Fleeton et al. "Self-Repiicave RNA Vaccines Elicit Protection against influenza A Virus, Respiratory Syncytial Virus and a Tickborne Encephalitis Virus". J Infect Diseases (2001) 183:1395-1398.

Fraenkel-Conrat H., "Togaviridae". Virology second edition, Prentice-Hall Inc. (1988) p. 2 pp. 99.

(56) References Cited

OTHER PUBLICATIONS

Freddolino et al., "Molecular Dynamics Simulations of the Complete Satellite Tobacco Mosaic Virus". Structure (2006) 14:437-449.
Fynan et al., "DNA vaccines: Protective Immunizations by parenteral, mucosal, and gene-gun inoculations". Proc Natl Acad Sci. (1993) 90:11478-11482.
Gamvrellis et al., "Vaccines that facilitate antigen entry into dendritic cells". Immunol Cell Biol. (2004) 82(5):506-516.
Geall et al. "Nonviral delivery of self-amplifying RNA vaccines". Proc Nat Acad Sci USA (2012) 109(36):14604-14609.
Geall et al., "Using self-amplifying mRNA vaccines to facilitate a rapid response to pandemic influenza". Eur Pharm Review (2014) 19:3 20-23.
Geisbert et al., "Postexposure Protection of Guinea Pigs against a Lethal Ebola Virus Challenge Is Conferred by RNA Interference". J Infect Dis. (2006) 193:1650-1657.
Giuliani et al., "A universal vaccine for serogroup B meningococcus". Proc Natl Acad Sci USA (2006) 103(29):10834-10839.
Gonçalves et al. "The effect of liposome size on the final lipid/DNA ratio of cationic lipoplexes". Biophysical J. (2004) 86(3): 1554-1563.
Graham, et al., "Priming Immunization Determines T Helper Cytokine mRNA Expression Patterns in Lungs of Mice Challenged with Respiratory Syncytial Virus". J Immunol. (1993) 151(4):2032-2040.
Granstein et al., "Induction of Anti-Tumor Immunity with Epidermal Cells Pulsed with Tumor-Derived RNA or Intradermal Administration of RNA". J Invest Dermatol. (2000) 114(4):632-636.
Greer et al., "A chimeric alphavirus RNA replicon gene-based vaccine for human parainfluenza virus type 3 induces protective immunity against intranasal virus challenge". Vaccine (2007) 25(3): 481-489.
Hamm et al., "Immunostimulatory RNA is a potent, inducer of antigen-specific cytotoxic and humoral immune response in vivo", Int Immunol. (2007) 19:297-304.
Heidel et al., "Administration in non-human primated of escalating intravenous doses of targeted nanoparticles containing ribonucleotide reductase subunit M2 siRNA". Proc Natl Acad Sci USA (2007) 104(14):5715-5721.
Herweijer et al., "Self-amplifying vectors for gene delivery". Adv Drug Delivery Rev. (1997) 27:5-16.
Heyes et al., "Cationic lipid saturation influences intracellular delivery of encapsulated nucleic acids". J Control Release (2005) 107:276-287.
Hoerr et al. "In vivo application of RNA leads to induction of specific cytotoxic T lymphocytes and antibodies", Eur J Immunol. (2000) 30:1-7.
Hope, et al., "Reduction of Liposome Size and Preparation of unilamellar Vesicles by Extrusion Techniques". Chapter 8 in Liposome Technology (1993) 1:123-129.
Hornung et al., "5'-Triphosphate RNA Is the Ligand for RIG-I". Science (2006) 314:994-997.
Huang, et al., "Immunization with a bovine herpesvirus 1 glycoprotein B DNA vaccine induces cytotoxic T-lymphocyte responses in mice and cattie". J General Virol. (2005) 86(4):887-898.
Iavarone et al., "A Point Mutation in the Amino Terminus of TLR7 Abolishes Signaling without Affecting Ligand Binding". J Immunol. (2011) 186:4213-4222.
Jeffs et al. "A scalable, extrusion-free method for efficient liposomal encapsulation of plasmid DNA", Pharma Research (2005) 22(3):362-372.
Johanning et al., "A Sindbis virus mRNA polynucleotide vector achieves prolonged and high level heterologous gene expression in vivo". Nucleic Acids Res. (1995) 23(9):1495-1501.
Johnson et al., "TLR9 agonist, but not TLR7/8, functions as an adjuvant, to diminish FI-RSV vaccine-enhanced disease, while either agonist used as therapy during primary RSV infection increases disease severity". Vaccine (2009) 27(23):3045-3052.
Kariko et al., "mRNA Is an Endogenous Ligand for Toll-like Receptor 3". J Biol Chem. (2004) 279(13):12542-12550.
Kariko et al., "Suppression of RNA Recognition by Toll-like Receptors: The Impact of Nucleoside Modification and the Evolutionary Origin of RNA". Immunity (2005) 23:165-175.
Khan K.H., "Review DNA vaccines roles against diseases". GERMS (2013) 3(1):26-35.
Kinnan et al., "Enhanced Immunogenicity to *Mycobacterium tuberculosis* by Vaccination with an Alphavirus Plasmid Replicon Expressing Antigen 85A". Infect Immun. (2003) 71 (1):575-579.
Kita et al. "Replication of Genetic information with Self-Encoded Replicase in Liposomes," Chembiochem. (2008) 9(15):2403-2410.
Knipe, et al. [Eds.]; Fields Virology, 4th edition, Lippincott Williams & Wilkins, 2001; pp. 690; vol. 1, p. 2.
Kofler et al., "Mimicking live fiavivirus immunization with a noninfectious RNA vaccine". Proc Natl Acad Sci USA (2004) 1001(7):1951-1956.
Kornbluth at al., "Immunostimulatory combinations: designing the next generation of vaccine adjuvants". J Leukocyte Biol. (2006) 80:1084-1102.
Kulkarni et al. "Factors affecting microencapsulation of drugs in liposomes". J Microencapsulation (1995) 12 (3):229-246.
Kumar et al., "Toll-like receptors and innate immunity". Biochem Biophys Res Commun. (2009) 388(4):621-625.
Kutzler et al., "DNA vaccines; ready for primetime?". Nature Rev Genetics (2008) 9(10):776-788.
Lazzaro et al., "CD 8 T-cell priming upon mRNA vaccination is restricted to bone-marrow-derived antigen-presenting cells and may involve antigen transfer from myocytes". Immunology (2015) 146(2):312-326.
Lee et al., "Venezuelan Equine Encephatlitis VirVectored Vaccines Protect Mice Against Anthrax Spore Challenge", Infect Immunity (2003) 71:1491-1496.
Leitner et al. "DNA and RNA-based vaccines: principles, progress and prospects". Vaccine (1999) 18(9-10):765-777.
Levine et al., "Vaccine development strategies for improving immunization: the role of modern immunology". Nature Immunol. (2004) 5(5):460-464.
Levy et al. "Quantitation of supercoiled circular content in plasmid DNA solutions using a fluorescence based method", Nucleic Acids Res. (2000) 28(12):e57.
Liljestrom et al., "A new generation of animal ceil expression vectors based on the Semliki Forest virus replicon." Bio/technology (1991) 9(12):1356-1361.
Liljestrom et. al., "In vitro mutagenesis of a full-length cDNA clone of Semliki Forest virus: the small 6,000-molecular-weight membrane protein modulates virus release." J Virology (1991) 65(8):4107-4113.
Ljungberg et al., "Increased Immunogenicity of a DNA-Launched Venezuelan Equine Encephalitis VirBased Replicon DNA Vaccine". J Virology (2007) 81(24):13412-13423.
Lonez et al., "Cationic liposomal lipids: From gene carriers to cell signaling", Progress in Lipid Research (2008) 47(5):340-347.
Lu et al., "Optimization of methods to achieve mRNA-mediated transfection of tumor cells in vitro and in vivo employing cationic liposome vectors". Cancer Gene Ther. (1994) 1(4):245-252 (Abstract).
Lundstrom K., "Biology and application of alphaviruses in gene therapy". Gene Thera. (2005) 12(Suppl 1):S92-S97.
Lyubchenko et al., "Visualization of supercoiled DNA with atomic force microscopy in situ". Proc Natl Acad Sci USA. (1997) 94:496-501.
Malone et al., "Cationic liposome-mediated RNA transfection", Proc. Natl. Acad. Sci. (PNAS) USA: Biochemistry (1989) 86(16):6077-6081.
Manning et al., "Infectivity of Liposomally Encapsulated Nucleic Acids Isolated From EMC Virus and Scrapie-Infected Mouse Brain", Intervirology (1983) 20:164-168.
Martin et al., "Characterization of formaldehyde-inactlvated poliovirus preparations made from live-attenuated strains". J General Virol. (2003) 84:1781-1788.
Martinon et al. "Induction of virspecific cytotoxic T lymphocytes in vivo by liposome-entrapped Mrna", Eur J Immuno. (1993) 23:1719-1722.

(56) References Cited

OTHER PUBLICATIONS

Maurer et al., "Spontaneous Entrapment of Polynucleotides upon Electrostatic Interaction with Ethanol-Destabilized Cationic Liposomes". Biophys J. (2001) 80:2310-2326.
McGlone, et al., Pig Production: Biological Principles and Applications. Cengage Learning, (2003)Chapter 8; pp. 99.
Merriam-Webster definition of "virion" (downloaded Mar. 14, 2016).
Merriam Webster, "IMAGINES Immunization" Merriam Webster's Medical Desk Dictionary (1993) pp. 326-327.
Mockey et al. "mRNA-based cancer vaccine: prevention of B16 melanoma progression and metastasis by systemic injection of MART1 mRNA histidyiated lipopolyplexes". Cancer Gene Therapy (2007) 14(9):802-814.
Morris-Downes et al., "A recombinant Semliki Forest virus particle vaccine encoding the prME and NS1 proteins of louping ill virus is effective in a sheep challenge model". Vaccine (2001) 19:3877-3884.
Mosca et al., "Molecular and cellular signatures of human vaccine adjuvants". Proc Natl Acad Sci USA (2008) 105(30):10501-10506.
Mossman et al., "Protection against Lethal Simian Immunodeficiency Virus SIVsmmPBj14 Disease by a Recombinant Semliki Forest Virus gp160 Vaccines and by a gp120 Subunit Vaccine". J Virology (1996) 70:1953-1960.
NCBI Reference Sequence. *Homo sapiens* coagulation factor VIII (FB), transcript variant 1, mRNA. Mar. 2016, pp. 1-18.
Obata et al., "Evaluation of pH-responsive liposomes containing amino acid-based zwitterionic lipids for improving intracellular drug delivery in vitro and in vivo". J Cont Release (2010); 142(2):267-276.
O'Hagan et al., "Induction of potent immune responses by cationic microparticles with adsorbed human immunodeficiency virus DNA vaccines". J Virol. (2001) 75(19):9037-9043.
National Library of Medicine. Organism overview of Encephalomyocarditis virus and of Poliovirus obtained from PubMed "Encephalomyocarditis virus" retrieved on Jun. 4, 2019 from https://www.ncbi.nlm.mih.gov/genome/?term=encephalomyocarditis+virus, and "Enterovirus C" retrieved on Jun. 4, 2019 from https://www.ncbi.nlm.nih.gov/genome/?term=poliovirus[orgn].
Ott et al., "A Cationic sub-micron emulsion [M59/DOTAP] is an effective delivery system for DNA vaccines". J Controlled Release (2002) 79(1-3): 1-5.
Papahadjopoulos, et al., "Cochleate Lipid Cylinders: Formation by Fusion of Unilamellar Lipid Vesicles". Biochim et Biophys Acta (1975) 394:483-491.
Papahadjopoulos, et al., "Incorporation of Macromolecules within Large Unilamellar Vesicles (LUV)", Annals NY Academy of Sciences (1978) 308(1):259-267.
Perri et al., "An alphavirus replicon particle chimera derived from Venezuelan equine encephalitis and sindbis viruses is a potent gene-based vaccine delivery vector". J Virol. (2003) 77(19):10394-10403.
Ramana et al. "Development of a liposomal nanodelivery system for nevirapine". J Biomed Science (2010) 17(1): 1-9.
Rayner et al., "Alphavirus vectors and vaccination". Rev Med Virol. (2002) 12:279-296.
Ren et al. "Immunogene therapy of recurrent glioblastoma multiforme with a liposomally encapsulated replication-incompetent Semliki forest virus vector carrying the human interleukin-12 gene—a phase 1/11 clinical protocol". J NeuroOnc. (2003) 64:147-154.
Rodriguez-Gascón et al., "Development of nucleic acid vaccines: use of self-amplifying RNA in lipid nanoparticles". Int J Nanomed. (2014) 9(1):1833-1843.
Sacco et al., "The Average Body Surface Area of Adult Cancer Patients in the UK: A Multicentre Retrospective Study". PLoS ONE (2010) 5(1):1-6.
Saeki et al., "Development and Characterization of Cationic Liposomes Conjugated with HVJ (Sendai Virus): reciprocal Effect of Cationic Lipid for In Vitro and In Vivo Gene Transfer", Human Gene Therapy (1997) 8(17):2134-2135.

Saenz-Badillos et al., "RNA as a tumor vaccine; a review of the literature". Exper Dermatol. (2001) 10(3): 143-154.
Samad et al. "Liposomal drug delivery systems: an updated review". Curr Drug Deliv. (Oct. 2007) 4(4):297-305.
Saxena et al., "Induction of immune responses and protection in mice against rabies using a self-replicating RNA vaccine encoding rabies virus glycoprotein". Vet Microbiol. (2009) 136(1-2):36-44.
Scheel, et al., "Toll-like receptor-dependent activation of several human blood cell types by protamine-condensed mRNA"; European Journal of Immunology; 2005; pp. 1557-1566.
Schirrmacher et al., "Intra-pinna anti-tumor vaccination with self-replicating infectious RNA or with DNA encoding a model tumor antigen and a cytokine". Gene Therapy (2000) 7:1137-1146.
Schlesinger et al. "Aiphavirus vectors for gene expression and vaccines". Curr Opin Biotech. (1999) 10:434-439.
Semple et al., "Efficient encapsulation of antisense oligonucleotides in lipid vesicles using ionizable aminolipids: formation of novel small multilamellar vesicle structures". Biochimica et Biophysics Acta (BBA)—Biomembranes, (2001) 1510(1-2):152-166.
Semple et al. "Rational design of cationic lipids for siRNA delivery". Nature Biotechnol. (2010) 28(2):172-176.
Sharma et al., "To scale or not to scale: the prinicples of does extrapolation". Br J Pharmacol. (2009) 157:907-921.
Silva, et al. "Effect of ultrasound parameters for unilamellar liposome preparation". Ultrasonics Sonochemistry (2010) 17(3):628-632.
Singh et al. "The effect of CTAB concentration in cationic PLG microparticles on DNA adsorption and in vivo performance". Pharma Res. (2003), 20(2):247-251.
Singh et al., "Cationic microparticles: A potent delivery system for DNA vaccines". Proc Natl Acad Sci USA (2000) 97(2):811-816.
Smerdou et al., "Non-viral amplification systems for gene transfer: Vectors based on alphaviruses." Curr Opin Mol Ther. (1999) 1(2):244-251.
Stability data of licensed vaccines as of Nov. 29, 2012.
Strejan, "Suppression of Chronic-Relapsing Experimental Allergic Encephalomyelitis in Strain-13 Guinea Pigs by Administration of Liposome-Associated Myelin Basic Protein". J Neuroimmun. (1984)7:27-41.
Stuart et al, "A new liposomal formulation for antisense oligodeoxynucleotides with small size, high incorporation efficiency and good stability", Biochimica et Biophysica Acta (2000) 1463(2):219-229.
Sugiyama et al., "Immunoadjuvant effects of polyadenylic:polyuridylic acids through LR3 and LR7", Int. Immunol. (2008) 20(1 ): 1-9.
Taylor et al., "DNA vaccination against respiratory syncytial virus in young calves". Vaccine (2005) 23(10):1242-1250.
Tseng et al. "Liposomes incorporated with cholesterol for drug release triggered by magnetic field". J Med Biol Engineering, (2007) 27(1): 29-34.
Ulmer et al., "Heterologous Protection Against influenza by Injection of DNA Encoding a Viral Protein". Science (1993) 259:1745-1749.
Vajdy et al. "Mucosal adjuvants and delivery systems for protein-, DNA- and RNA-based vaccines". Immunol Cell Biol. (Dec. 2004) 82(6):617-27.
Vasiljeva et al., "Identification of a novel function of the alphavirus capping apparatus. RNA 5'-triphosphatase activity of Nsp2". J Biol Chem. (2000) 275(23):17281-17287.
Vassilev et al., "Microparticle-mediated RNA immunization against bovine viral diarrhea virus." Vaccine (2001) 19:2012-2019.
Vignuzzi et ai., "Naked RNA immunization with replicons derived from poliovirus and Semliki Forest virus genomes for the generation of a cytotoxic T cell response against the influenza A virus nucleoprotein". J Gen Virol. (2001) 82(7):1737-1747.
Wang et al., "PH-sensitive immunoliposomes mediate target-cell-specific delivery and controlled expression of a foreign gene in mouse". Proc Natl Acad Sci USA (1987) 84:7851-7855.
Ward et al., "Generation of CTL responses using Kunjin replicon RNA". Immun Cell Biol. (2003) 81(1):73-78.
Weide et al., "Direct injection of Protamine-protected mRNA: Results of a Phase 1/2 Vaccination Trial in Metastatic Melanoma Patients". J Immunother. (2009) 32(5):498-507.

(56) References Cited

OTHER PUBLICATIONS

Weide et al., "Results of the First Phase I/II Clinical Vaccination Trial with Direct injection of mRNA". J Immunother. (2008) 31(2):180-188.
Whitehead et al., "Knocking down barriers: advances in siRNA delivery". Nat Rev Drug Discovery (2009) 8:129-138.
Wilson et al., "Biological properties of poliovirus encapsulated in lipid vesicles: Antibody resistance and infectivity in virresistant cells". Proc Natl Acad Sci USA (1977) 74(8):3471-3475.
Wilson et al., "The Introduction of Poliovirus RNA into Ceils via Lipid Vesicles (Liposomes)". Ceil (1979) 17:77-84.
Wilson et al. "The combination of stabilized plasmid lipid particles and lipid nanoparticle encapsulated CpG containing oligodexoynucleotides as a systemic genetic vaccine". J Gene Med. (2009) 11:14-25.
Wloch et al., "Safety and immunogenicity of a Bivalent of CMV DNA Vaccine in Healthy in Healthy Adult Subjects". J Infect Dis. (2008) 197(12):1634-1642.
Xiong et al., "Sindbis virus: an efficient, broad host range vector for gene expression in animal cells". Science (1989) 243:1188-1191.
Yamamoto et al. "Current, prospects for mRNA gene delivery". Eur J Pharma Biopharm. (2009)71:484-489.
Yi et al., "A Cationic Lipid Emulsion/DNA Complex as a Physically Stable and Serum-Resistant Gene Delivery". Pharma Res. (2000) 17:314-320.
Ying et al. "Cancer therapy using a self-replicating RNA vaccine". Nat Med. (1999) 5:823-827.
Yoder et al., "Role of Complement in Neutralization of Respiratory Syncytial Virus". J Med Virol. (2004) 72:688-694.
Yoffe, "Predicting the sizes of large RNA molecules" PNAS (2008) 105:16153-16158.
Yoneyama et al., "RIG-I family RNA helicases: cytoplasmic sensor for antiviral innate immunity". Cyto Growth Factor Rev.(2007) 18(5-6):545-551.
Yoon et al., "DNA-Mediated Immunization of Mice with Plasmid Encoding HBs Antigen". J Korean Med Sci. (1999) 14:187-192.
Zhang, J., et al., "Ionization Behavior of Amino Lipids for siRNA Delivery: Determination of Ionization Constants, SAR, and the Impact of Lipid pKa on Cationic Lipid-Biomembrane Interactions," Langmuir (2011) 15(5):1907-1914.
Zhou et al., "RNA Melanoma Vaccine: Induction of Antitumor Immunity by Human Glycoprotein 100 mRNA Immunization". Human Gene Therapy (1999) 10(16):2719-2724.
Zhou et al., "Self-replicating Semliki Forest virus RNA as recombinant vaccine". Vaccine (1994) 12(16):1510-1514.
Zimmermann et al. "RNAi-mediated gene silencing in non-human primates". Nature (2006) 441:111-114.
Zuckerman J.N., "The importance of injecting vaccines into muscle. Different patients need different needle sizes". BMJ (2000) 321(7271):1237-1238.
Zuckerman, Principles and Practice of Travel Medicine; (2001) pp. 168.
Notice of Opposition in relation to European Patent No. 2591103B1 (Appln No. 11736498.4) dated May 27, 2020 (17 pages).
Notice of Opposition in relation to European Patent No. 2591103B1 (Appln No. 11736498.4) dated May 28, 2020 (44 pages).
Opposition Document D60—Johnson Declaration from EP2591114, European Equivalent of U.S. Appl. No. 13/808,153, filed Aug. 8, 2018.
Patentee's Reply to Opposition in relation to European Patent No. 2591103B1 (Appln No. 11736498.4) dated Oct. 24, 2020 (28 pages).
Preliminary Opposition Opinion from EP2591114, European Equivalent of U.S. Appl. No. 13/808,153. dated Feb. 23, 2018.
Final Decision and Upheld Claims from EP2591114, European Equivalent of U.S. Appl. No. 13/808,153, dated Nov. 27, 2018.
Certified U.S. Appl. No. 61/223,347, filed Jul. 6, 2009; priority document to WO2011005799.
Certified U.S. Appl. No. 61/265,653, filed Dec. 1, 2009.

Certified Priority Document U.S. Appl. No. 61/280,510; priority WO2011140627 (Cullis, Pieter).
Certified U.S. Appl. No. 61/361,780, filed Jul. 6, 2010.
Certified U.S. Appl. No. 61/361,794, filed Jul. 6, 2010.
Declaration by Prof. Peter Liljestrom, dated Aug. 7, 2018.
Declaration by Prof. Peter Liljestrom, dated Mar. 31, 2019.
Declaration Andrew Geaii dated Sep. 11, 2014.
Declaration of Prof. Liljestrom submitted to the European Patent Office in the opposition proceedings concerning EP2590676 B1.
Declaration of Professor Liljestrom dated Dec. 11, 2018 submitted in EP2590676, itself having annexes A-G.
Declaration by Johnson dated Oct. 22, 2020 (9 pages).
Third Party Observations under Art. 115 EPC Nov. 3, 2016; pp. 1-17.
Kumar et al., "Single histidine residue in head-group region is sufficient to impart remarkable gene transfection properties to cationic iipids: evidence for histidine-mediated membrane fusion at acidic pH". Gene Therapy (2003) 10:1208-1215.
Xu et al., "Drug Delivery Trends in Clinical Trials and Translational Medicine: challenges and opportunities in the delivery of nucleic acid-based therapeutics". J Pharma Sci. (2011) 100(1):38-52.
Certified U.S. Appl. No. 61/361,828, filed Jul. 6, 2010.
EP 2729126 (Application No. 12738679.5) Third Party Observations filed Mar. 8, 2019, 24 pages.
Declaration by Russell Johnson cited in EP2729126 on Jul. 4, 2018 and in opposition filed on Sep. 23, 2021 (4 pages).
Opponents arguments by Georg Schnappauf filed on Jan. 14, 2022 in opposition to European Patent No. 2591103, in 17 pages.
Opponents arguments by Janssen Vaccines & Prevention B.V. filed on Jan. 14, 2022 in opposition to European Patent No. 2591103, in 24 pages.
Auxiliary requests 1,2 and 3 (claims 1-13) filed on Dec. 22, 2017 in relation to the Opposition of European Patent No. 259067661 (Appln No. 11741348.4), in 6 pages.
Szoka et al., "Procedure for Preparation of Liposomes with Large Internal Aqueous Space and High Capture by Reverse-phase Evaporation", Proc Natl Acad Sci. USA (1978) 75(9): 4194-4198.
ThermoFisher Scientific, "Ribosomal RNA Sizes", submitted in EP Opposition against Application No. EP 2591103 on Jan. 14, 2022, 1 page.
Lorenzi et al. "Intranasal vaccination with messenger RNA as a new approach in gene therapy: use against tuberculosis." BMC Biotech. (2010) 10(1): 1-11.
Smith Korsholm et al. "The adjuvant mechanism of cationic dimethyldioctadecylammonium liposomes." Immunol. (2007) 121(2): 216-226.
Espuelas et al. "Effect of synthetic lipopeptides formulated in liposomes on the maturation of human dendritic cells." Mol. Immunol. (2005) 42(6): 721-729.
Communication of the Board of Appeals pursuant to Art. 15(1) of the Rules of Procedure of the Boards of Appeal issued on Mar. 25, 2021 in European Patent Application Publication No. 2590676, in 12 pages.
Jones et al. "DNA vaccination protects against an influenza challenge in a double-blind randomised placebo-controlled phase 1b clinical trial." Vaccine (2009) 27: 2506-2512.
U.S. Appl. No. 17/511,762, filed Oct. 27, 2021.
EP 12722942.5 (Moderna's submission of Jul. 9, 2018).
A-Plus™ Poly(A) Polymerase Tailing Kit Protocol Nov. 16, 2006 (Capture Date).
Adler et al., "Role of human cytomegalovirus UL131A in cell type-specific virus entry and release," J. Gen. Virol., 2006, 87:2451-2460.
Agris et al., "Thermodynamic Contribution of Nucleoside Modifications to Yeast tRNAphe Anticodon Stem Loop Analogs," Acta Biochimica Polonica, vol. 46(1):163-172 (1999).
Aissaoui et al: "Efficient topical delivery of plasmid DNA to lung in vivo mediated by putative triggered, PEGylated pDNA nanoparticles", Journal of Controlled Release, Elsevier, Amsterdam, NL, vol. 154, No. 3, Jun. 4, 2011 Jun. 4, 2011), pp. 275-284.
Akinc et al., "The Onpattro Story and the Clinical Translatioin of Nanomedicines Containing Nucleic Acid-Based Drugs," Nature Nanotechnology, vol. 14:1084-1087 (2019).

(56) References Cited

OTHER PUBLICATIONS

Ambegia et al., "Stabilized Plasmid-Lipid Particles Containing PEG-diacylglycerols Exhibit Extended Circulation Lifetimes and Tumor Selective Gene Expression," Biochimica et Piophysica Acta., vol. 1669:155-163 (2005).
Amidi et al. "Antigen-expressing immunostimulatory liposomes as a genetically programmable synthetic vaccine." Systems and Synthetic Biology, vol. 5, 2011, pp. 21-31. (Year: 2011).
Amidi et al. "Optimization and quantification of protein synthesis inside liposomes." Journal of Liposome Research, vol. 20(1), 2010, pp. 73-83. (Year: 2010).
Amidi, "Induction of humoral and cellular immune responses by antigen-expressing immunostimulatory liposomes." Journal of Controlled Release; Aug. 1, 2012; p. 3, left-hand col. p. 20, lines 13-14 example 1.
Anderson et al. "Incorporation of pseudouridine into mRNA enhances translation by diminishing PKR activation," Nucleic Acids Research, 38(17):5884-5892 (2010).
Anderson et al., "Nucleoside modifications in RNA limit activation of 2'-5'-oligoadenylate synthetase and increase resistance to cleavage by Rnase L", Nucleic Acids Research vol. 39(21):9329, published online on Aug. 3, 2011.
Andries et al., "N(1)-Methylpseudouridine-Incorporated mRNA Outperforms Pseudouridine-Incorporated mRNA by Providing Enhanced Protein Expression and Reduced Immunogenicity in Mammalian Cell Lines and Mice," Journal of Controlled Release, vol. 217:337-344 (2015).
Applicant's Jun. 26, 2017 response in opposition of European Patent Application 12738679.5.
Application underlying the present patent as filed with the application No. EP 18 153 312.6.
Arvin AM, Gershon AA. Live attenuated varicella vaccine. Annu Rev Microbial. 1996;50:59-100.
Aso et al., "Effect of freezing rate on physical stability of lyophilized cationic liposomes", Chem Pharm. Bull. 53(3) 301-204 (2005).
Ausubel et al., "Short protocols in molecular biology", Immunology, Chapter 11, pp. 11-1-11-29.
Bahl et al., "Preclinical and Clinical Demonstration of Immunogenicity by mRNA Vaccines against H10N8 and H7N9 Influenza Viruses," Mol Ther. vol. 25(6):1316-1327, Erratum in: Mol Ther. vol. 30(8):2874 (2017).
Bai et al., "Gene Transfer to Vein Graft Wall by HVJ-Liposome Method: Time Course and Localization fo Gene Expression," Ann Thorac Surg, vol. 66:814-820 (1998).
Balasuriya et al., "Expression of the two major envelope proteins of equine arteritis virus as a heterodimer is necessary for induction of neutralizing antibodies in mice immunized with recombinant venezuelan equine encephalitis virus replicon particles," J. Virol., 2000, 74(22):10623-10630.
Banerjee, "5'-Terminal Cap Structure in Eucaryotic Messenger Ribonucleic Acids," Microbiological Reviews, vol. 44(2):175-205 (1980).
Bangs et al., "Mass Spectrometry of mRNA Cap 4 from Trypanosomatids Reveals Two Novel Nucleosides," The Journal of Biological Chemistry, vol. 267(14):9805-9815 (1992).
Barichello JM, et al., Complexation of siRNA and pDNA with cationic liposomes: the important aspects in lipoplex preparation, Methods Mil. Biol., 2010, 605: 461-72 (Nov. 21, 2009).
Barnett et al., "Antibody-Mediated Protection against Mucosal Simian-Human Immunodeficiency Virus Challenge of Macaques Immunized with Alphavirus Replicon Particles and Boosted with Trimeric Envelope Glycoprotein in MF59 Adjuvant," Journal of Virology, 84(12):5975-5985 (2010).
Barratt, "Therapeutic applications of colloidal drug carriers." PSTT, 2000, vol. 3, No. 5, pp. 163-171.
Bauer et al., "Toll-like receptors (TLRs) and innate immunity", Handbook of Experimental Pharmacology, ISBN 978-3-540-72166-6, 2008, pages i-xi, 1-240, and a cover page (2008).
Bernstein et al., "Randomized, double-blind, Phase 1 trial of an alphavirus replicon vaccine for cytomegalovirus in CMV seronegative adult volunteers," Vaccine, 28:484-493 (2010).
Bettinger T et al. "Peptide-Mediated RNA Delivery: A Novel Approach for Enhanced Transfection of Primary and Post-Mitotic Cells," (2001) Nucleic Acids Research 29(18): 3882-3891.
Bettinger, T., et al., "Recent Developments in RNA-BASED strategies for cancer gene therapy", Current Opinion in Molecular Therapeutics, Current Drugs, London, GB, vol. 3, No. 2, Apr. 1, 2001, pp. 116-124.
Biochemistry/Lubert Stryer (1995) 4th Ed.: title pages and p. 23.
BioRad Product catalog post-published evidence.
Blakney, "The next generation of RNA vaccines: self-amplifying RNA." Document obtained from https://portlandpress.com/biochemist/article/43/4/14/229206/The-next-generation-of-RNA-vaccines-self on Sep. 20, 2021, originally published Aug. 2021, pp. 14-17. (Year: 2021).
Brand et al., "Biosynthesis of a hypermodified nucleotide in *Saccharomyces carlsbergensis* 17S and HeLa-Cell 18S ribosomal ribonucleic acid", Biochem. J., vol. 169:71-77 (1978).
Britt et al., "Cell surface expression of human cytomegalovirus (HCMV) gp55-116 (gB): use of HCMV-recombinant vaccinia virus-infected cells in analysis of the human neutralizing antibody response," J. Virol., 1990, 64(3):1079-1085.
Britt et al., "Cytomegalovirus," In Fields Virology, 3rd edition, BN Fields, DM Knipe, PM Howley (ed.), Philadelphia, PA, Lippincott-Raven, 1996, pp. 2493-2523.
Britt et al., "Human cytomegalovirus virion proteins," Hum. Immunol., 2004, 65:395-402.
CRC Handbook of Chemistry and Physics, 101st Edition, CRC Press 2020—Section 6 vapor pressure of ice.
CV Dr Olatokumbo Ogunleye.
Carine et al., "Vaccination of calves using the BRSV nucleocapsid protein in a DNA prime-protein boost strategy stimulates cell-mediated immunity and protects the lungs against BRSV replication and pathology," Vaccine Elsevier Ltd, GB, 26(37):4840-4848 (2008).
Cha et al., "Human cytomegalovirus clinical isolates carry at least 19 genes not found in laboratory strains," J. Virol., 1996, 70(1):78-83.
Chang et al., "Synthesis and Solution Conformation Studies of 3-substituted Uridine and Pseudouridine Derivatives," Bioorganic & Medicinal Chemistry, vol. 16:2676-2686 (2008).
Chatterjee et al., "The Archaeal COG1901/DUF358 SPOUT-Methyltransferase Members, Together with Pseudouridine Synthase Pus10, Catalyze the Formation of 1-Methylpseudouridine at Position 54 of tRNA," RNA, vol. 18, pp. 421-433 (2012).
Chee et al, "Hypothetical Protein UL128", UniProtKB/Swiss-Prot: P16837, Dep. Feb. 1, 1991.
Chee et al., "Analysis of the protein-coding content of the sequence of human cytomegalovirus strain AD169," Curr. Top. Microbiol. Immunol., 1990, 154:125-169.
Chen et al. "An Overview of Liposome Lyophilization and its Future Potential," Journal of Controlled Release 142:299-311 (2010).
Chen et al., "Influence of particle size on the in vivo potency of lipid nanoparticle formulations of siRNA," J Control Release, PMID: 27238441 (2016).
Cheng et al. "Naked RNA vaccine controls tumors with down-regulated MHC class I expression through NK cells and perforin-dependent pathways" Eur J Immunol. Jul. 2004;34(7):1892-900.
Christ, "Gefriertrocknung mit System" (with D6a, a timestamp, showing that this document was available as of Jan. 22, 2010) (see immediately below for translation.).
Christ, "Smart Freeze Drying" Manual Jan. 2010.
Compton et al., "Receptors and immune sensors: the complex entry path of human cytomegalovirus," Trends Cell. Bio., 2004, 14(1):5-8.
Cortesi et al., "Effect of DNA complexation and freeze-drying on the physicochemical characteristics of cationic liposomes", Antisense & Nucleic Acid Drug Development 10:205-215 (2000).
Cox et al., "Plasmid DNA and Messenger RNA for Therapy," Handbook of Pharmaceutical Biotechnology, Chapter 7.2, pp. 971-1011 (2007).

(56) References Cited

OTHER PUBLICATIONS

Davis et al., "Ribonucleic Acids from Yeast which Contain a Fifth Nucleotide" Document D22, Opposition in App. No. 19216461.4, pp. 907-915 (1957).
Davison AJ, UL115; gL [Human Herpesvirus 5], NCBI Reference Sequence: YP_081555.1, Dep. Sep. 16, 2004.
Davison AJ, UL130 [Human Herpesvirus 5], NCBI Reference Sequence: YP-081565.1, Dep. Sep. 16, 2004.
Davison AJ, UL131A [Human Herpesvirus 5], NCBI Reference Sequence: YP_081566.1, Dep. Sep. 16, 2004.
Davison AJ, UL75; gH [Human Herpesvirus 5], NCBI Reference Sequence: YP_081523.1, Dep. Sep. 16, 2004.
Davison et al., "The human cytomegalovirus genome revisited: comparison with the chimpanzee cytomegalovirus genome," J. Gen. Virol., 2003, 84:17-28.
Declaration by Russell Johnson dated Sep. 21, 2022 in opposition filed in EP2591103, Int'l filing date Jul. 6, 2012, (2 pages).
Declaration entitled "Annex A" by Russell Johnson cited in EP2729126 in opposition filed on Sep. 23, 2021 (4 pages).
Declaration from Dr Olatokumbo Ogunleye.
Declaration of Russell N. Johnson dated Dec. 10, 2018.
Declaration of Russell N. Johnson dated May 6, 2021, filed in Opposition proceeding in EP 2750707.
Declaration of Kimberly J. Hassett, dated Nov. 18, 2021.
Defang et al., "Induction of neutralizing antibodies to Hendra and Nipah glycoproteins using a Venezuelan equine encephalitis virus in vivo expression system," Vaccine Elsevier Ltd. GB,29(2):212-220 (2010).
Depledge et al., "Deep Sequencing of Distinct Preparations of the Live Attenuated Varicella-Zoster Virus Vaccine Reveals a Conserved Core of Attenuating Single-Nucleotide Polymorphisms," J Viral. vol. 90(19):8698-704 (2016).
Dolan et al, "Genetic Content of Wild-Type Human Cytomegalovirus", J. Gen. Virol. May 2004; 85(Pt 5):1301-12.
Drug Discovery Handbook, edited by Shayne Cox Gad, Wiley Interscience, 2005; Chapter 27: RNA—based therapies, pp. 1259 to 1308.
Dunn et al., "Functional profiling of a human cytomegalovirus genome," Proc. Natl. Acad. Sci. USA, 2003, 100 (24): 14223-14228.
Durbin et al., "RNAs Containing Modified Nucleotides Fail to Trigger RIG-I Conformational Changes for Innate Immune Signaling," mBio. vol. 7(5):e00833-16. doi: 10.1128/mBio.00833-16. PMID: 27651356; PMCID: PMC5030355 (2016).
Dwarki et al., "Cationic Liposome-Mediated RNA Transfection," Methods in Enzymology, vol. 217:644-654 (1993).
Earl et al., "A Chemical Synthesis of the Nucleoside I-Methylpseudouridine," J. Heterocyclic Chem, vol. 15:699-700 (1977).
Eastman et al., "Influence of Phospholipid Asymmetry on Fusion between Large Unilamellar Vesicles," Biochemistry, vol. 31, (1992), pp. 4262-4268.
Eberhardt et al. "Modulation of mRNA Stability as a Novel Therapeutic Approach," Pharmacology & Therapeutics 114:56-73 (2007).
Elkington et al., "Ex Vivo Profiling of CD8+—T-Cell Responses to Human Cytomegalovirus Reveals Broad and Multispecific Reactivities in Healthy Virus Carriers," Journal of Virology (2003), vol. 77, No. 9, pp. 5226-5240.
Elliott et al., "Alphavirus replicon particles encoding the fusion or attachment glycoproteins of respiratory syncytial virus elicit protective immune responses in BALB/c mice and functional serum antibodies in rhesus macaques," Vaccine Elsevier LTD, GB, 25(41):7132-7144, (2007).
ER, et al., "The encapsulation and release of guanosine from PEGylated liposomes." Journal of Liposome Research, 2009, vol. 19, No. 1, pp. 29-36.
Ernsting et al., "Factors controlling the pharmacokinetics, biodistribution and intratumoral penetration of nanoparticles," J Control Release, vol. 172(3)782-94. doi: 10.1016/j.jconrel.2013.09.013, PMID: 24075927; PMCID: PMC3891171 (2013).

Excerpt from "Chemical Book" on DLinDMA Sep. 9, 2021.
Excerpt from PubChem: Transfectam.
Excerpt from Moderna's 2018 10-K.
Expert opinion Prof. Schubert.
Excerpt of textbook "The immune system" by Peter Parham, Third edition, (2009) Cover page, Table contents and pp. 49 and 50 common general knowledge.
Faneca et al., "Drug Delivery Systems: Advanced Technologies Potentially Applicable in Personalised Treatment", Advances in Predictive, Preventive and Personalised Medicine 4:153-184, 2013.
Faure et al., "Control of the in vivo Biodistribution of Hybrid Nanoparticles with Different Poly(ethylene glycol) Coatings." Small, 2009, vol. 5, No. 22, pp. 2565-2575.
Felgner et al., "Cationic lipid-mediated transfection in mammalian cells: Lipofection", J. Tiss. Cult. Meth. vol. 15:63-68 (1993).
Fechter et al., "Recognition of mRNA Cap Structures by Viral and Cellular Proteins," Journal fo General Virology, vol. 86:1239-1249 (2005).
Fraenkel-Conrat et al., (Ed.), Virology second edition, Prentice-Hall Inc., Englewood Cliffs, New Jersey; 1988; from Chapter 3, "Enveloped Plus-strand RNA Viruses:Togaviridae", pp. 96-103.
Freer et al., "Varicella-zoster virus infection: natural history, clinical manifestations, immunity and current and future vaccination strategies," New Microbial. vol. 41(2):95-105, (2018).
Frolov et al., "Alphavirus-based expression vectors: Strategies and applications," 93 Proceedings of the National Academy of Sciences USA (1996).
Furuichi et al., "Viral and Cellular mRNA Capping: Past and Prospects," Advances in Virus Research, vol. 55:135-184 (2000).
Gao et al., "Synthesis of a Novel Series of Cationic Lipids that can act as Efficient Gene Delivery Vehicles Through Systematic Heterocyclic Substitution of Cholesterol Derivatives," Gene Therapy 8 (2001), 855-863.
Garcia-Valcarcel et al., "Induction of neutralizing antibody and T-cell responses to varicella-zoster virus (VZV) using Ty-virus-like particles carrying fragments of glycoprotein E (gE)" Vaccine. Apr.-May 1997; 15(6-7): 709-19.
Geldmacher et al., "Therapeutic vaccination for cancer immunotherapy: Antigen selection and clinical responses", Human Vaccines, vol. 7, No. sup1, Jan. 1, 2011 (Jan. 1, 2011), pp. 115-119.
Genini et al., "Serum antibody response to the gH/gL/pUL 128-131 five protein complex of Serum antibody response to the gH/gL/pUL 128-131 five-protein complex of human cytomegalovirus (HCMV) in primary and reactivated HCMV infections,"Journal of Clinical Virology, 52:113-118 (2011).
Giraud et al., "Generation of monoclonal antibodies to native human immunodeficiency virus type 1 envelope glycoprotein by immunization of mice with naked RNA", J Virol Methods. Apr. 1999;79(1):75-84.
GlaxoSmithKline, SAM/Protein Mixed Modality Study Data, PowerPoint presentation (2019).
Goel et al., "Distinct antibody and memory B cell responses in SARS-COV-2 naïve and recovered individuals after mRNA vaccination," Science Immunology, vol. 6, eabi6950, Apr. 2021, pp. 1-13; 2021.
Graham, "Biological challenges and technological opportunities for respiratory syncytial virus vaccine development," Immunological Reviews, 239(1):149-166 (2011).
Hahn et al, "Deletion Mapping of the Encephalomyocarditis Virus Primary Cleavage Site". J. Virol. Aug. 2001; 75 (15):7215-8.
Harvey et al., "Kunjin Virus Replicon Vectors for Human Immunodeficiency Virus Vaccine Development", 2003 Journal of Virology vol. 77 No. 14 pp. 7796-7803.
Hassett et al., "Optimization of Lipid Nanoparticles for Intramuscular Administration of mRNA Vaccines," Mol Ther Nucleic Acids (2019).
Hatakeyama, et al., "Systemic delivery of siRNA to tumors using a lipid nanoparticle containing a tumor-specific cleavable PEG-lipid." Biomaterials, 2011, vol. 32, pp. 4306-4316.
Hess et al., "Vaccination with mRNAs encoding Tumor-Associated Antigens and Granulocyte-Macrophage Colony-Stimulating Factor Efficiently Primes CTL Responses, but is Insufficient to Overcome

(56) References Cited

OTHER PUBLICATIONS

Tolerance to a Model Tumor/Self Antigen,," Cancer Immunol Immunother, vol. 55:672-683 (2006).

Hidmark et al., "Humoral Responses against Coimmunized Protein Antigen but Not against Alphavirus-Encoded Antigens Require Alpha/Beta Interferon Signaling," Journal of Virology, 80(14):7100-7110 (2006).

Hiroshi, et al., "Replication of Genetic Information with Self-Encoded Replicase in Liposomes." ChemBioChem; Oct. 13, 2008; pp. 2403-2410; vol. 9(15).

Ho, "Cytomegalovirus," In Principles and Practice of Infectious Diseases, GL Mandell, RG Douglas, and JE Bennett (ed.), Wiley, New York, NY, 1979, pp. 1307-1323.

Hobo et al., "Improving Dendritic Cell Vaccine Immunogenicity by Silencing PD-1 Ligands using siRNA-lipid Nanoparticles Combined with Antigen mRNA Electroporation," Cancer Immunol Immunother, vol. 62:285-297 (2013).

Hobo et al., "Immunogenicity of Dendritic Cells Pulsed with MAGE3, Survivin and B-Cell Maturation Antigen mRNA for Vaccination of Multiple Myeloma Patients," Cancer Immunol Immunother, vol. 62:1381-1392 (2013).

Hobom et al., "Fast screening procedures for random transposon libraries of cloned herpesvirus genomes: mutational analysis of human cytomegalovirus envelope glycoprotein genes," J. Virol., 2000, 74(17):7720-7729.

Hoerr, "Plenary Lectures and Oral Presentations: Stabilized Messenger RNA (RNActive™) as a Tool for Innovative Gene Delivery," Tissue Engineering 13(4): 886-887; 2007.

Hwang et al., "Alpha-Methylprednisolone Conjugated Cyclodextrin Polymer-Based Nanoparticles for Rheumatoid Arthritis Therapy," International Journal of Nanomedicine, 2008, 3(3), 359-371.

Immordino et al., "Stealth liposomes: review of the basic science, rationala, and clinical application, existing and potential." International Journal of Nanomedicine, 2006, vol. 1, pp. 297-315.

International Search Report for International Application No. PCT/US2012/045847 dated Oct. 10, 2012.

International Search Report for International Application No. PCT/US2012/045854 dated May 9, 2014.

Janeway et al., "Induced innate responses to infection", Immunobiology: The Immune System in Health and Disease, Part 1, Chapter 2, pp. 87-106, 5th Ed., New York: Garland Science (2001), available from https://www.ncbi.nlm.nih.oov/books/NBK27122/.

Jones et al., "Long-term storage of DNA-free RNA for use in vaccine studies", BioTechniques 43:675-681 (Nov. 2007).

Ju et al., "Novel Cholesterol-Based Cationic Lipids as Transfecting Agents of DNA for Efficient Gene Delivery," Int. J. Mol. Sci. 16:5666-5681; 2015.

Kamrud et al., "Development and characterization of promoterless helper RNAs for the production of alphavirus replicon particle", J Gen Virol. Jul. 2010; 91 (Pt 7): 1723-7. Epub Feb. 24, 2010.

Kariko, "Incorporation of Pseudouridine into mRNA yields Superior Nonimmunogenic Vector with Increased Translational Capacity and Biological Stability", Mol Ther., vol. 16(11):1833-1840 (2008).

Kariko et al., "Naturally Occurring Nucleoside Modifications Suppress the Immunostimulatory Activity of RNA: Implication for Therapeutic RNA Development," Curr Opin Drug Disc & Dev., vol. 10(5):524-532 (2007).

Kariko et al., "Increased Erythropoiesis in Mice Injected with Submicrogram Quantities of Pseudouridine—Containing mRNA Encoding Erythropoietin," Mal Ther 20(5):948-53 (2012).

Kariko et al., "Generating the optimal mRNA for therapy: HPLC purification eliminates immune activation and improves translation of nucleoside-modified, protein-encoding mRNA", Nucleic Acids Research, 39 (21), e142, published online on Sep. 2, 2011.

Kawauchi et al., "Gene Therapy for Attenuating Cardiac Allograft Arteriopathy using Ex Vivo E2F Decoy Transfection by HVJ-AVE-Liposome Method in Mice and Nonhuman Primates," Circulation Research, pp. 1063-1068 (2000).

Kawano et al., "Effects of Polyethylene Glycol Spacer Length and Ligand Density on Folate Receptor Targeting of Liposomal Doxorubicin In Vitro." Journal of Drug Delivery, 2011, vol. 2011, No. 160967, pp. 1-6.

Kierzek et al., "Influence of N6-lsopentenyladenosine (k6A) on Thermal Stability of RNA Duplexes," Biophysical Chemistry, vol. 91:135-140 (2001).

Kim et al., "Enhanced siRNA Delivery using Cationic Liposomes with new Polyarginine-Conjugated PEG-Lipid," International Journal of Pharmaceutics, vol. 392:141-147 (2010).

Kimura et al. "Recombinant Varicella-Zoster Virus Glycoproteins E and I: Immunologic Responses and Clearance of Virus in a Guinea Pig Model of Chronic Uveitis", 1998 Journal of Infectious Diseases 178:310-317.

Kimura et al. "Varicella-Zoster Virus Glycoproteins E and I Expressed in Insect Cells Form a Heterodimer That Requires the N-Terminal Domain of Glycoprotein I", 1997 Virology 233:382-391.

Kinnan, et al., "Enhanced Immunogenicity to *Mycobacterium tuberculosis* by Vaccination with an Alphavirus Plasmid Replicon Expressing Antigen 85A" Infection and Immunity, vol. 71(1):575-579 (2003).

Kitajima et al., "Efficient Transfer of Synthetic Ribozymes into Cells using Hemagglutinating Virus of Japan (HVJ)-Cationic Liposomes," The Jounral of Biological Chemistry, vol. 272(43):27099-27106 (1997).

Klibanov et al., "Amphipathic polyethyleneglycols effectively prolong the circulation time of liposomes", FEBS Letters, Elsevier, Amsterdam, NL, vol. 268, No. 1, Jul. 30, 1990 (Jul. 30, 1990), pp. 235-237.

Kreiter et al., "Tumor Vaccination using Messenger RNA: Prospects of a Future Therapy," Current Opinion in Immunology, vol. 23:399-406 (2011).

Kumar et al., "New Histidylated Cationic Lipids for DNA- and mRNA-Based Lipofection," Molecular Therapy 9(S1): S258-S259, 2004.

Kutinova et al., "Immune response to vaccinia virus recombinants expressing glycoproteins gE, gB, gH, and gL of varicella-zoster virus," Virol., 2001,280:211-220.

Lambert et al., "Intradermal Vaccine Delivery: Will New Delivery Systems Transform Vaccine Administration?" Vaccine, vol. 26:3197-3208 (2008).

Lee et al., "Multiagent vaccines vectored by Venezuelan equine encephalitis virus replicon elicits immune responses to Marburg virus and protection against anthrax and botulinum neurotoxin in mice," Vaccine, Elsevier, Amsterdam, NL, vol. 24, No. 47-48; pp. 6886-6892; Nov. 17, 2006.

Leroueil et al., "Wide varieties of cationic nanoparticles induce defects in supported lipid bilayers" Nano Lett. vol. 8(2):420-4. (2008).

Li et al., "Protection against Respiratory Syncytial Virus Infection by DNA Immunization," J Exp Med., vol. 188, (1998), pp. 681-688.

Li et al., "Low-pH-Sensitive Poly(ethylene glycol) (PEG)-Stabilized Plasmid Nanolipoparticles: Effects of PEG Chain Length, Lipid Composition and Assembly Conditions on Gene Delivery," The Journal of Gene Medicine, vol. 7:67-79 (2005).

Liu et al., "Designer Lipids Advance Systemic siRNA Delivery," (2010) Molecular therapy 18(4): 669-670.

Liu et al., "Size Homogeneity of a Liposome Preparation is Crucial for Liposome Biodistribution in Vivo", Journal of Liposome Research 2(1): 57-66 (1992).

Ljungman et al., "Definitions of cytomegalovirus infection and disease in transplant recipients," Clin. Infect. Dis., 2002, 34:1094-1097.

Lobue et al. "Multivalent norovirus vaccines induce strong mucosal and systemic blocking antibodies against multiple strains." Vaccine; 2006; pp. 5220-5234; vol. 24.

Lv et al., "Toxicity of cationic lipids and cationic polymers in gene delivery." Journal of Controlled Release, vol. 114 (2006), pp. 100-109. (Year: 2006).

Macagno et al., "Isolation of Human Monoclonal Antibodies That Potently Neutralize Human Cytomegalovirus Infection by Targeting Different Epitopes on the gH/gL/UL128-131A Complex", 2010 Journal of Virology 84 (2): 1005-1013.

(56) References Cited

OTHER PUBLICATIONS

Maclachlan "Liposomal formulations for nucleic acid delivery", Antisense Drug Technologies, 2nd Edition, Chapter 9, 237-270, 2007.
Mandal et al., "Delivery of Macromolecules into Cytosol using Liposomes Containing Hemolysin," Methods in Enzymology, vol. 372:319-339 (2003).
Mahato, "Water insoluble and soluble lipids for gene delivery", Adv. Drug Delivery Rev.,2005, 57(5):699-712.
Mann et al., "DNA Transfer into Vascular Smooth Muscle using Fusigenic Sendai Virus (HJV)-Liposomes," Molecular and Cellular Biochemistry, vol. 172:3-12 (1997).
Matsuura et al., "Polycation liposome-mediated gene transfer in vivo," Biochimica et Biophysica Acta, vol. 1612, 2003, pp. 136-143.
McGown, "UV Absorbance measurements of DNA in microplates", BioTechniques, vol. 28:60-64 (2000).
Mocarski et al., "Cytomegalovirus and their replication," In Fields Virology, 4th edition, vol. 2, 2001, DM Knipe and PM Howley (ed.), Lippincott Williams and Wilkins, Philadelphia, PA, pp. 2629-2673.
Mok et al., "Venezuelan equine encephalitis virus replicon particles encoding respiratory syncytial virus surface glycoproteins induce protective mucosal responses in mice and cotton rats," Journal of Virology, The American Society for Microbiology, 81(24):13710-13722 (2007).
Molina et al.: The stability of lyophilized lipid/DNA complexes during prolonged storage, Journal of Pharmaceutical Sciences, vol. 93(9), (2004).
Montana et al. "Employment of Cationic Solid-Lipid Nanoparticles as RNA Carriers," Bioconjugate Chem. 18:302-308 (2007).
Monslow et al., "Immunogenicity generated by mRNA vaccine encoding VZV gE antigen is comparable to adjuvanted subunit vaccine and better than live attenuated vaccine in nonhuman primates," Vaccine vol. 38(36):5793-5802 (2020).
Morais et al., "The Critical Contribution of Pseudouridine to mRNA COVID-19 Vaccines," Frontiers in Cell and Development Biology, vol. 9:1-9 (2021).
Motorin et al., "RNA Nucleotide Methylation," Advanced Review, vol. 2:611-631 (2009).
Motorin et al., "5-Methylcytosine in RNA: Detection, Enzymatic Formation and Biological Functions," Nucleic Acids Research, vol. 38(5):1415-1430 (2011).
MRNA-ONLY™ Prokaryotic mRNA Poly(A)—Tailing Kit Protocol Nov. 16, 2006 (Capture Date).
Murphy et al., "Coding potential of laboratory and clinical strains of cytomegalovirus," Proc. Natl. Acad. Sci. USA, 2003, 100(25):14976-14981.
Naslund et al. "Role of innate signalling pathways in the immunogenicity of alphaviral replicon-based vaccines," Virology Journal, 8(1):36 (2011).
Narang et al., "Cationic Lipids with Increased DNA Binding Affinity for Nonviral Gene Transfer in Dividing and Nondividing Cells," Bioconjugate Chem. 16 (2005), 156-166.
Nucleic Acids in Innate Immunity, Various Authors (2008) CRC Press.
Operating manual freeze-dryer Alpha 1-4 LCS plus and Alpha 2-4 LSC plus by Christ, revised version of Dec. 16, 2013.
Oussoren et al., "Lymphatic Uptake and Biodistribution of Liposomes After Subcutaneous Injection: III. Influence of Surface Modification with Poly(ethyleneglycol)." Pharmaceutical Research, 1997, vol. 14, No. 10, pp. 1479-1484.
Pang et al., "Structure of a Modified Nucleoside in Archaebacterial tRNA which Replaces Ribosylthymine," The Journal of Biological Chemistry, vol. 257(7):3589-3592 (1982).
Pardi et al., "Nucleoside-Modified mRNA Vaccines Induce Potent T Follicular Helper and Germinal Center B Cell Responses," Journal of Experimental Medicine, vol. 215(6):1571-1588 (2018).
Pascolo, "Messenger RNA-based vaccines", Expert Opinion on Biological the, Informa Healthcare, Ashley, London; GB, vol. 4, No. 8, Aug. 1, 2004 (Aug. 1, 2004), pp. 1285-1294.
Pascolo, "Vaccination With Messenger RNA." Methods in Molecular Medicine, 2006, vol. 127, pp. 23-40.
Patel et al., "The Importance of Apparent pKa in the Development of Nanoparticles Encapsulating siRNA and mRNA," Trends Pharmacol Sci., vol. 42, No. 6, (2021), pp. 448-460.
Patentee Submission to EPO in EP Application No. 11758014.2, dated Nov. 13, 2018.
Peng et al., "The gH-gL complex of herpes simplex virus (HSV) stimulates neutralizing antibody and protects mice against HSV type 1 challenge," J. Virol., 1998, 72(1):65-72.
Phumiamorn et al., "Induction of humoral and cell-mediated immunity to hepatitis B surface antigen by a novel adjuvant activity of Oka varicella vaccine." Journal of General Virology; 2003; pp. 287-291; vol. 84.
Pomeroy et al., "Cytomegalovirus: epidemiology and infection control," Am. J. Infect. Control, 1987, 15(3):107-119.
Post-filed evidence submitted on Jun. 12, 2014 during prosecution of EP2578685 B1 (D1a).
Post-filing experimental evidence submitted by the Patentee during the examination phase of EP 18 153 312.6 on Apr. 5, 2019.
Poveda et al., "Establishing Preferred Product Characterization for the Evaluation of RNA Vaccine Antigens," Vaccines (Basel) vol. 7(4):131, doi: 10.3390/vaccines7040131, PMID: 31569760; PMCID: PMC6963847 (2019).
Print-out of the entry for the ScriptCap™ m7G Capping System from the Epicentre Biotechnologies homepage from Nov. 2006, pp. 1-2.
Print-out of the entry for the m7G(5')ppp(5')G RNA Cap Structure Analog from the New England Biolabs homepage, from Apr. 2010, pp. 1-2.
"ProductInfoNow," Modern Drug Discovery, vol. 6(6):57-62 (2003).
Pushko et al., "Replicon-Helper Systems from Attenuated Venezuelan Equine Encephalitis Virus: Expression of Heterologous Genes in Vitro an dImmunization against Heterologous Pathogens in Vivo," Virology, 239:389-401(1997).
Reap et al., Development and preclinical evaluation of an alphavirus replicon particle vaccine for cytomegalovirus, Vaccine, Elsevier LTD, GB, 25(42):7441-7449, (2007).
Reap et al., "Cellular and humoral immune responses to alphavirus replicon vaccines expressing cytomegalovirus pp65, IE1 and GB proteins," Clin. Vacc. Immunol., 2007, 14(6):748-755.
Reichman et al., "The Journal of Antibiotics", vol. XXX(2):129-131 (1977).
Reijenga et al., "Development of Methods for the Determination of pKa Values," Analytical Chemistry Insights, vol. 8:53-71 (2013).
Robbins et al., "2'-O-Methyl-Modified RNAs Act as TLR7 Antagonists," Mol. Ther. vol. 15(9):1663-1669 (2007).
Rodrigueza et al. "Development and Antitumor Activity of a BCL-2 Targeted Single-Stranded DNA Oligonucleotide," Cancer Chemother Pharmacol 74:151-166, 2014.
Roldao et al., "Virus-like particles in vaccine development", Expert Rev Vaccines. Oct. 2010;9(10): 1149-76.
Roos, "Europe Approves Sanofi's Intradermal Flu Vaccine," University of Minnesota Center for Infections Disease Research and Policy [online: cidrap.umn.edu/news-perspective/2009/02/europe-approves-sanofis-intradermal-flu-vaccine], pp. 1-2 (2009).
Rubin, "Clinical approach to infection in the compromised host," In Infection in the Organ Transplant Recipient, 4th edition, R Rubin and LS Young (ed.), Kluwer Academic Press, New York, NY, 2002, pp. 573-679.
Ryckman et al., "Characterization of the human cytomegalovirus gH/gL/UL128-131 complex that mediates entry into epithelial and endothelial cells," J. Virol., 2008, 82(1):60-70.
Ryckman et al., "Human cytomegalovirus TR strain glycoprotein O acts as a chaperone promoting gH/gL incorporation into virions, but is not present in virions," J. Virol., 2010, 84(5):2597-2609.
Saccoccio, "Thesis: CMV Vaccine Development based on Epithelial Entry Mediators UL128, UL130, and UL131," Jun. 3, 2011, Retrieved from the Internet: URL: https//digarchiveJibrary.vcu.edu/bitstreamjhandle/10156/3452/SACCOCCIO FRANCES PhD.pdf?sequence=1-1 retrieved on Mar. 18, 2014] Impact on future vaccine design; p. 160 (2011). Chapter: Peptides to UL130 and UL131. Neutralize CMV Infection of Mucosal Epithelial Cells; p. 96.

(56) References Cited

OTHER PUBLICATIONS

Sadzuka et al., "Effect of Polyethyleneglycol (PEG) Chain on Cell Uptake of PEG-Modified Liposomes," J. Liposome Res., 13(2), 157-172 (2003).
Sahin et al., "Nature Reviews Drug Discovery", 13:759-780, published online on Sep. 19, 2014.
Santos et al., "Design of Peptide-Targeted Liposomes Containing Nucleic Acids," Biochimica et Biophysica Acta, vol. 1798:433-441 (2010).
Sawai et al., "A Novel Method of Cell-Specific mRNA Transfection" 64 Molecular Genetics and Metabolism 44-51 (1998).
Schlake et al., "Developing mRNA-Vaccine Technologies," RNA Biology 9(11): 1319-1330, published in Nov. 2012.
Schleiss, "Cytomegalovirus vaccine development", Curr Top Microbiol Immunol. 2008;325:361-82.
Schoenmaker et al., "mRNA-lipid nanoparticle COVID-19 vaccines: Structure and stability," International Journal of Pharmaceutics 601; 120586, pp. 1-13; 2021.
Search Report issued in EP Application No. 21298987.3, dated May 25, 2022.
Shade et al.,"Unknown protein [Human parvovirus B19]". GenBank: AAA66867.1 Dep. 05171995.
Shah et al., "Shingrixfor Herpes Zoster: A Review," Skin Therapy Lett. vol. 24(4):5-7, PMID: 31339679 (2019).
Shimamura et al., "Human cytomegalovirus infection elicits a glycoprotein M (gM)/gN-specific virusneutralizing antibody response," J. Virol., 2006, 80(9):4591-4600.
Sonoke et al., "Tumor Regression in Mice by Delivery of Liposomes," Cancer Research, vol. 68:8843-8851 (2008).
Spelios et al., "Effect of Spacer Attachment Sites and pH-Sensitive Headgroup Expansion on Cationic Lipid-Mediated Gene Delivery of Three Novel Myristoyl Derivatives," Biophys. Chem. 129 (2007), 137-147.
Spikevax Patient Information, European Medicines Agency, pp. 1-5 (2022).
Sriwongsitanont et al. "Physiochemical Properties of PEG-Grafted Liposomes." Chem Pharm Bull; 2002; pp. 1238-1244; vol. 50(9).
Stagno et al., "Cytomegalovirus," In Infectious Diseases of the Fetus and Newborn Infant, 6th edition, JS Remington and JO Klein (ed.), WB Saunders, Philadelphia, PA, 1995, pp. 312-353.
Stedman's Medical Dictionary; 27th Edition; Lippincott, Williams & Wilkins; published 2000, p. 1963.
Sticchi et al., "The Intradermal Vaccination: Past Experiences and Current Perspectives," J Prev Med Hyg, vol. 51:7-14(2010).
Strauss et al., "The Alphaviruses: Gene Expression, Replication, and Evolution," Microbiological Reviews, 58(3): 491-562 (1994) (excerpt).
Su et al., "In Vitro and in Vivo mRNA Delivery using Lipid-Enveloped pH-Responsive Polymer Nanoparticles," Molecular Pharmaceutics, vol. 8:774-787 (2011).
Submitted claims to the EPO on Sep. 30, 2008 in the case EP 06 81 3536.7 (EP1979364) prior art under Art. 54(2) EPC.
Szebeni et. al., "Activation of complement by therapeutic liposomes and other lipid excipient-based therapeutic products: prediction and prevention," Adv Drug Deliv Rev. vol. 63(12):1020-30 (2011).
Szebeni, "Complement activation-related pseudoallergy: a stress reaction in blood triggered by nanomedicines and biolocials," Mol Immunol. vol. 61 (2):163-73 (2014).
Szebeni et al., "Complement activation as a bioequivalence issue relevant to the development of generic liposomes and other nanoparticulate drugs," Biochem Biophys Res Commun. vol. 468(3):490-7. doi: 10.1016/j.bbrc.2015.06.177 (2015).
Tang et al. "Design of Freeze-Drying Processes for Pharmaceuticals: Practical Advice," Pharmaceutical Research, vol. 21(2), (2004).
Tannous et al., "Secreted blood reporters: Insights and applications", Biotechnol. Adv., 2011, 29(6):997-1003.
Tcherepanova et al, "Ectopic Expression of a Truncated CD40L Protein from Synthetic Post-Transcriptionally Capped RNA in Dendritic Cells Induces High Levels of IL-I2 Secretion," BMC Molecular Biology 2008, 9:90.

The International Association for the Properties of Water and Steam, Pizer\ Czech Republic, Sep. 2011.
Thompson et al., "Mucosal and systemic adjuvant activity of alphavirus replicon particles," Proceedings of the National Academy of Sciences,! 03{10):3722-3727 (2006).
Tonkin et al., "Alphavirus Replicon-Based Enhancement of Mucosal and Systemic Immunity is Linked to the Innate Response Generated by Primary Immunization," Vaccine, 28(18): 3238-3246 (2010).
Torchilin et al., "Poly(ethylene glycol) on the liposome surface: on the mechanism of polymer-coated liposome longevity." Biochimica et Biophysica Acta, 1994, vol. 1195, pp. 11-20.
Tranchant et al. "Physicochemical Optimisation of Plasmid Delivery by Cationic Lipids," (2004) J Gene Med 6: S24-S35.
Tubulekas et al., "Alphavirus expression vectors and their use as recombinant vaccines: a minireview" 190 Gene 191-195 (1997).
Uddin "Cationic Lipids Used in Non-Viral Gene Delivery Systems," Biotechnology and Molecular Biology Review 2(3): 058-067, 2007.
Van Bleek et al., "RSV 2010: Recent advances in research on respiratory syncytial virus and other pneumoviruses," Vaccine, 29{43):7285-7291 (2011).
Van Den Berg et al., "Shielding the Cationic Charge of Nanoparticle-Formulated Dermal DNA Vaccines is Essential for Antigen Expression and Immunogenicity," Journal of Controlled Release, vol. 141:234-240 (2010).
Van Der Velden et al., "Vector Design for Optimal Protein Expression", Sep. 1, 2001, p. 576.
Van Winden, "Freeze-drying of liposomes: theory and practice "Methods Enzymol., vol. 367:99-110 (2003).
Varnum et al., "Identification of proteins in human cytomegalovirus (HCMV) particles: the HCMV proteome," J. Virol., 2004, 78(20):10960-10966.
VirTis Advantage Plus marketing brochure 2008.
VirTis Advantage Plus specification sheet 2013.
Wang et al., "Human cytomegalovirus virion protein complex required for epithelial and endothelial cell tropism," Proc. Natl. Acad. Sci. USA, 2005, 102(5):18153-18158.
Weissman et al., "HIV Gag mRNA Transfection of Dendritic Cells (DC) Delivers Encoded Antigen to MHC Class I and II Molecules, Causes DC Maturation, and Induces a Potent Human in Vitro Primary Immune Response," The Journal of Immunology, 165(8):4710, (2000).
Wille et al., "A human cytomegalovirus gO-null mutant fails to incorporate gH/gL into the virion envelope and is unable to enter fibroblasts and epithelial and endothelial cells," J. Virol., 2010, 84(5):2585-2596.
Willis et al., "Liposome-Anchored Vascular Endothelial Growth Factor Aptamers," Bioconjugate Chem., vol. 9:573-582 (1998).
Wisse et al., "The Size of Endothelial Fenestrae in Human Liver Sinusoids: Implications for Hepatocyte-Directed Gene Transfer," Gene Therapy, vol. 15:1193-1199 (2008).
Woodward et al., "Varicella Virus Vaccine Live: A 22-Year Review of Postmarketing Safety Data," Open Forum Infect Dis. Vol. 6(8):ofz295. doi: 10.1093/ofid/ofz295. PMID: 31392326; PMCID: PMC6685817 (2019).
https://www.convertunits.com/from/atmosphere+[standard]/to/mtorr, D42.
Xu et al., "Characterization of immune Responses Elicited in Macaques Immunized Sequentially with Chimeric Vee/ SIN Alphavirus Replicon Particles Expressing SIVGag and/or HIVEnv and with Recombinant HIVgp140Env Protein," Aids Research and Human Retroviruses, Mary Ann Liebert, 22(10): 1022-1030 (2006).
Xu et al., "Sequential priming and boosting with heterologous HIV immunogens predominantly stimulated T cell immunity against conserved epitopes," AIDS; 20(18); 2293-2303; Nov. 28, 2006.
Xu, Y., et al., Physicochemical characterization and purification of cationic lipoplexes, Biophys J., 1999, 77(1):341-53.
Xue et al., "Lipid-Based Nanocarriers for RNA Delivery," Curr Pharm Des. vol. 21(22):3140-7, (2015).
Yadava et al., "Effect of lyophilization and freeze-thawing on the stability of siRNA-liposome complexes", AAPS Pharm Sci Tech, vol. 9(2), (2008).

(56) References Cited

OTHER PUBLICATIONS

Yang et al., "Overcoming the inhibitory effect of serum on lipofection by increasing the charge ratio of cationic liposome to DNA," Gene Therapy, vol. 4, 1997, pp. 950-960; 1997.
Yarian et al., "Structural and Functional Roles of the N1- and N3-Protons of Ψ attRNA's Position 39," Nucleic Acids Research, vol. 27(17):3542-3549 (1999).
Yu et al., "Effects of Moisture Content on the Storage Stability of Dried Lipoplex Formulations," Journal of Pharmaceutical Sciences 98(9): 3278-3289; 2009.
Zhao et al., "N/P ratio significantly influences the transfection efficiency and cytotoxicity of a polyethylenimine/chitosan/DNA complex", Biol. Pharm. Bull., 2009, 32(4):706-10.
Zhu et al. "Vaccines for Gonorrhea: Can We Rise to the Challenge?" Frontiers in Microbiology, vol. 2, Jan. 1, 2011, 13 pages.
Zhu et al., "Lipid and Polymeric Carrier-Mediated Nucleic Acid Delivery," Expert Opin. Drug Deliv. 7(10): 1209-1226, 2010.
Zhu et al., "Systemic Gene Expression after Intravenous DNA Delivery into Adult Mice," Science, 261: 209-211 (1993).
Zimmer et al., "RNA Replicons—A New Approach for Influenza Virus Immunoprophylaxis," Viruses, vol. 2:413-434 (2010).
Zust et al., "Ribose 2'-O-Methylation Provides a Molecular Signature for the Distinction of Self and Non-self mRNA Dependent on the RNA Sensor Mda5,", Nature Immunology, vol. 12(2):137-144 (2011).
U.S. Appl. No. 17/560,019, filed Dec. 22, 2021.
U.S. Appl. No. 17/848,294, filed Jun. 23, 2022.
U.S. Appl. No. 17/848,299, filed Jun. 23, 2022.
U.S. Appl. No. 17/560,052, filed Dec. 22, 2021.
U.S. Appl. No. 17/808,519, filed Jun. 23, 2022.
U.S. Appl. No. 17/560,059, filed Dec. 22, 2021.
U.S. Appl. No. 17/560,116, filed Dec. 22, 2021.
U.S. Appl. No. 17/560,092, filed Dec. 22, 2021.
U.S. Appl. No. 17/848,337, filed Jun. 23, 2022.
U.S. Appl. No. 16/114,621, filed Aug. 28, 2018.
U.S. Appl. No. 16/714,877, filed Nov. 16, 2019.
U.S. Appl. No. 61/361,828, filed Jul. 6, 2010.
U.S. Appl. No. 61/505,088, filed Jul. 6, 2011.
U.S. Appl. No. 61/529,878, filed Aug. 31, 2011.
U.S. Appl. No. 61/494,745, filed Jun. 8, 2011.
U.S. Appl. No. 61/494,882, filed Jun. 8, 2011.
U.S. Appl. No. 61/404,413, filed Oct. 1, 2010.
U.S. Appl. No. 61/542,533, filed Oct. 2, 2011.
U.S. Appl. No. 61/570,690, filed Dec. 14, 2011.
U.S. Appl. No. 61/576,705, filed Dec. 16, 2011.
U.S. Appl. No. 61/578,271, filed Dec. 21, 2011.
U.S. Appl. No. 61/618,862, filed Apr. 2, 2012.
U.S. Appl. No. 17/512,258, filed Oct. 27, 2021.
Office Action issued in U.S. Appl. No. 13/808,080, dated May 25, 2022.
Office Action issued in U.S. Appl. No. 17/560,116, dated May 31, 2022.
Office Action issued in U.S. Appl. No. 17/560,052, dated Jul. 12, 2022.
Office Action issued in U.S. Appl. No. 17/560,138, dated Aug. 23, 2022.
Office Action issued in U.S. Appl. No. 17/560,092, dated Aug. 4, 2022.
Office Action issued in U.S. Appl. No. 17/560,059, dated Jul. 15, 2022.
Office Action issued in U.S. Appl. No. 17/560,019, dated May 31, 2022.
Office Action issued in U.S. Appl. No. 17/696,143, dated Aug. 30, 2022.
Office Action issued in U.S. Appl. No. 17/511,762, dated Sep. 15, 2022.
Office Action issued in U.S. Appl. No. 16/837,115, dated Apr. 22, 2022.
Office Action issued in U.S. Appl. No. 16/714,891, dated May 26, 2022.
Office Action, dated Dec. 21, 2022, issued in U.S. Appl. No. 16/656,929.
Office Action, dated Nov. 23, 2022, in U.S. Appl. No. 17/560,019.
Office Action, dated Nov. 23, 2022, in U.S. Appl. No. 17/560,052.
Office Action, dated Nov. 25, 2022, in U.S. Appl. No. 17/560,059.
Office Action, dated Dec. 8, 2022, in U.S. Appl. No. 17/560,116.

* cited by examiner

DODMA

DLinDMA

DLenDMA

WITHOUT ANY FRAGMENTATION

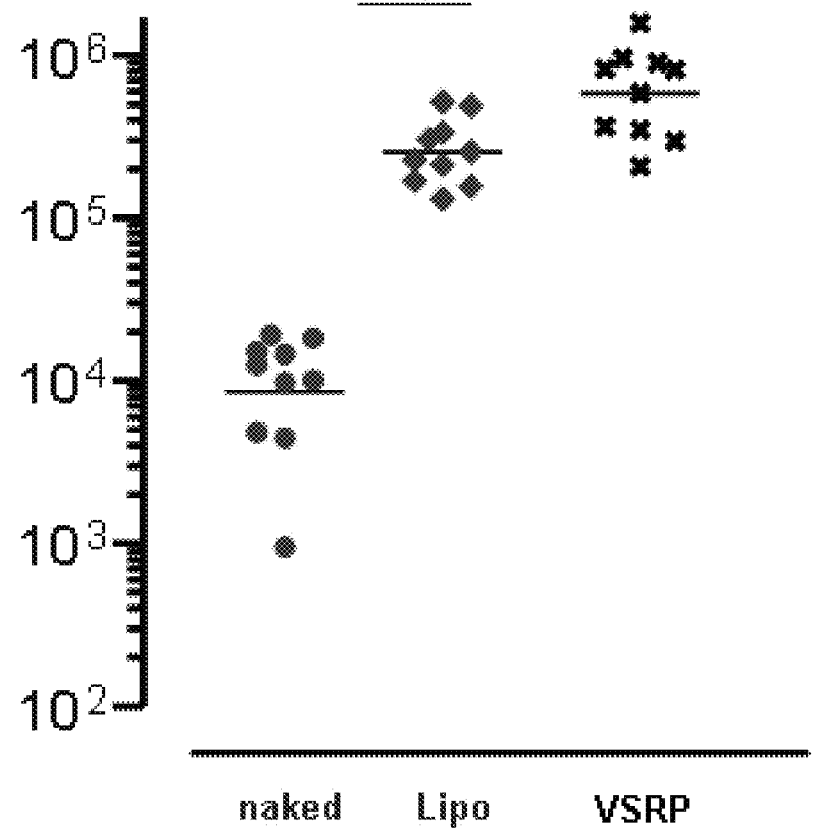
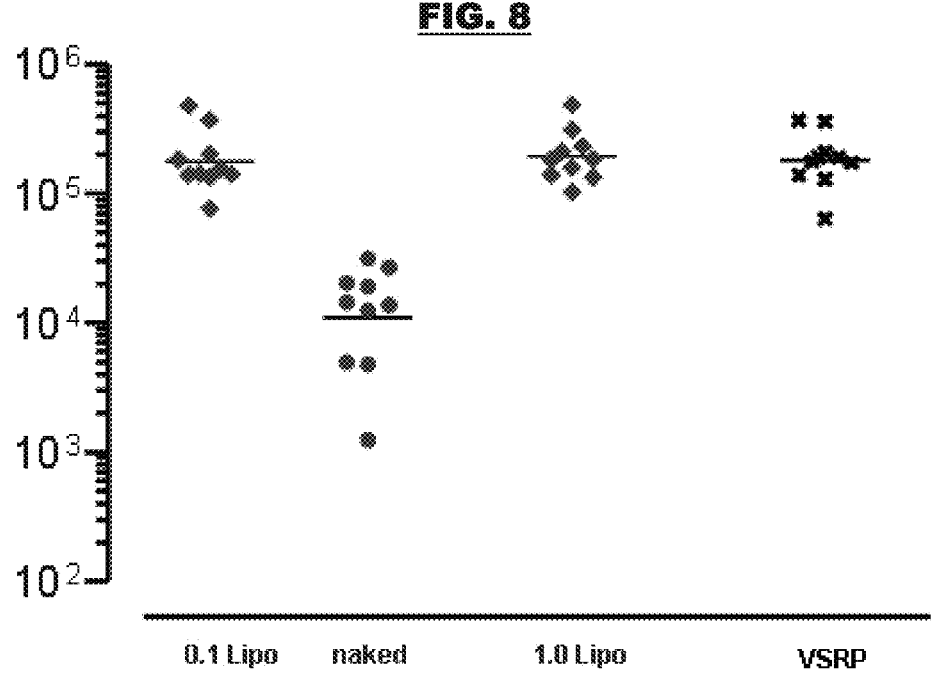

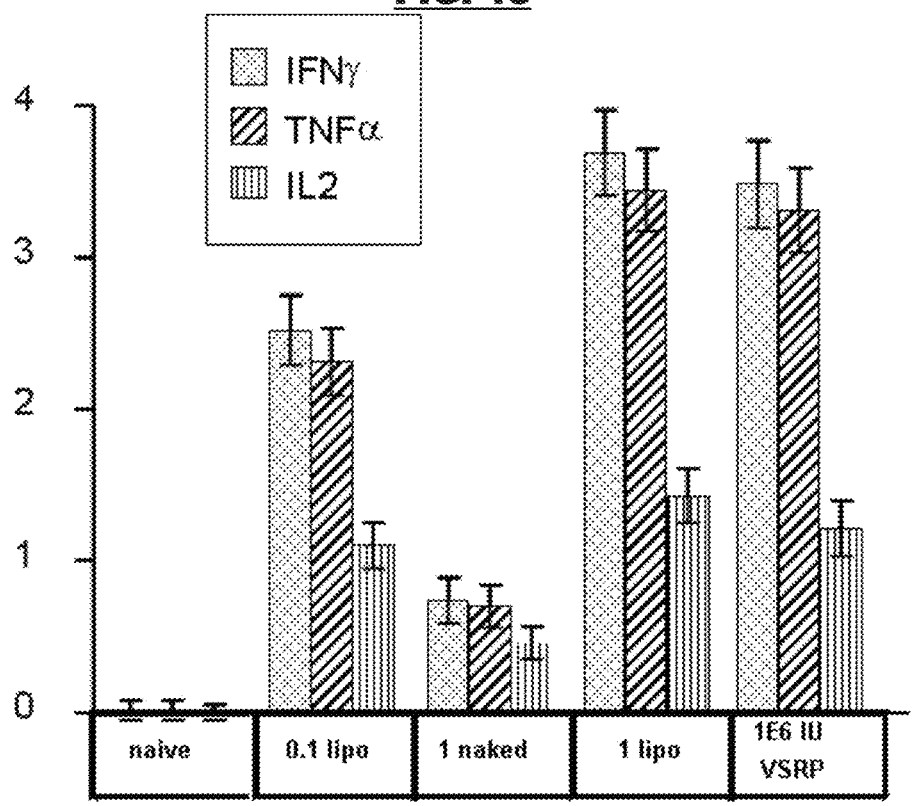
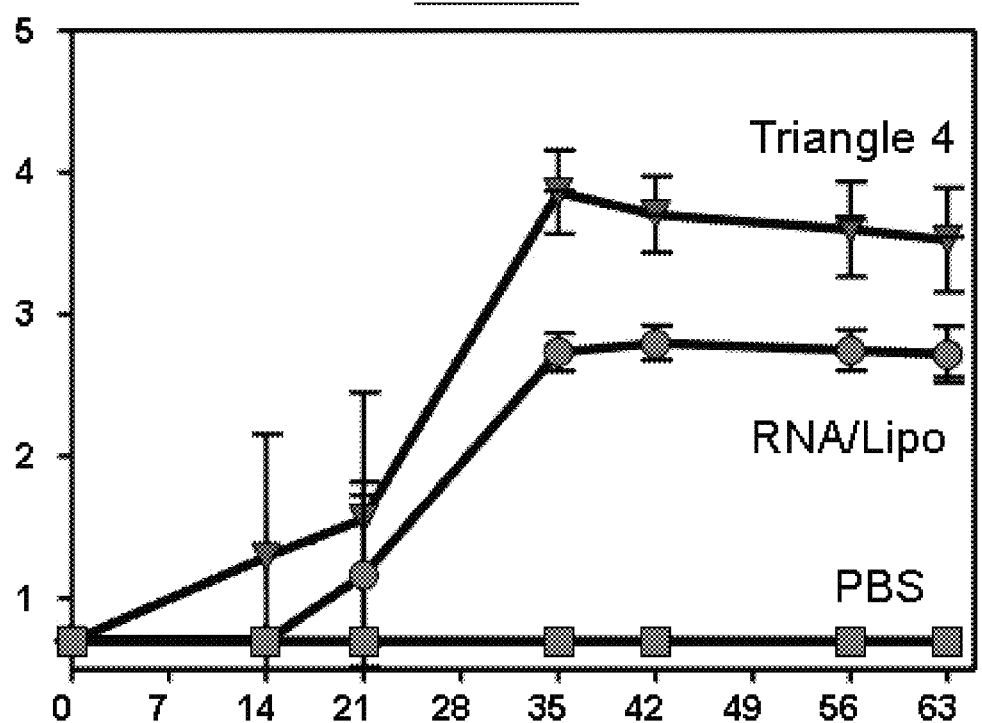

METHODS OF ADMINISTERING LIPID FORMULATIONS WITH VIRAL IMMUNOGENS

CROSS-REFERENCE TO RELATED APPLICATIONS

This application is a divisional of U.S. patent application Ser. No. 13/808,080, filed Mar. 14, 2013, which is a U.S. National Phase of International Application No. PCT/US2011/043105, filed Jul. 6, 2011 and published in English, which claims the benefit of U.S. Provisional Application No. 61/361,830, filed Jul. 6, 2010, and U.S. Provisional Application No. 61/378,837, filed Aug. 31, 2010. The complete contents of the above-listed applications are hereby incorporated herein by reference for all purposes

TECHNICAL FIELD

This invention is in the field of non-viral delivery of RNA for immunisation.

BACKGROUND

The delivery of nucleic acids for immunising animals has been a goal for several years. Various approaches have been tested, including the use of DNA or RNA, of viral or non-viral delivery vehicles (or even no delivery vehicle, in a "naked" vaccine), of replicating or non-replicating vectors, or of viral or non-viral vectors.

There remains a need for further and improved nucleic acid vaccines.

DISCLOSURE OF THE INVENTION

According to the invention, RNA encoding an immunogen is delivered in a liposome for the purposes of immunisation. The liposome includes lipids which have a pKa in the range of 5.0 to 7.6. Ideally the lipid with a pKa in this range has a tertiary amine; such lipids behave differently from lipids such as DOTAP, which has a quaternary amine group. At physiological pH amines with a pKa in the range of 5.0 to 7.6 have neutral or reduced surface charge, whereas a lipid such as DOTAP is strongly cationic. The inventors have found that liposomes formed from quaternary amine lipids (e.g. DOTAP) are less suitable for delivery of immunogen-encoding RNA than liposomes formed from tertiary amine lipids (e.g. DLinDMA).

Thus the invention provides a liposome having a lipid bilayer encapsulating an aqueous core, wherein: (i) the lipid bilayer comprises a lipid having a pKa in the range of 5.0 to 7.6, and preferably having a tertiary amine; and (ii) the aqueous core includes a RNA which encodes an immunogen. These liposomes are suitable for in vivo delivery of the RNA to a vertebrate cell and so they are useful as components in pharmaceutical compositions for immunising subjects against various diseases.

The invention also provides a process for preparing a RNA-containing liposome, comprising steps of: (a) mixing RNA with a lipid at a pH which is below the lipid's pKa but is above 4.5, to form a liposome in which the RNA is encapsulated; and (b) increasing the pH of the resulting liposome-containing mixture to be above the lipid's pKa.

The Liposome

The invention utilises liposomes in which immunogen-encoding RNA is encapsulated. Thus the RNA is (as in a natural virus) separated from any external medium by the liposome's lipid bilayer, and encapsulation in this way has been found to protect RNA from RNase digestion. The liposomes can include some external RNA (e.g. on their surface), but at least half of the RNA (and ideally all of it) is encapsulated in the liposome's core. Encapsulation within liposomes is distinct from, for instance, the lipid/RNA complexes disclosed in reference 1.

Various amphiphilic lipids can form bilayers in an aqueous environment to encapsulate a RNA-containing aqueous core as a liposome. These lipids can have an anionic, cationic or zwitterionic hydrophilic head group. Liposomes of the invention comprise a lipid having a pKa in the range of 5.0 to 7.6, and preferred lipids with a pKa in this range have a tertiary amine. For example, they may comprise 1,2-dilinoleyloxy-N,N-dimethyl-3-aminopropane (DLinDMA; pKa 5.8) and/or 1,2-dilinolenyloxy-N,N-dimethyl-3-aminopropane (DLenDMA). Another suitable lipid having a tertiary amine is 1,2-dioleyloxy-N,Ndimethyl-3-aminopropane (DODMA). See FIG. 3 & reference 2. Some of the amino acid lipids of reference 3 may also be used, as can certain of the amino lipids of reference 4. Further useful lipids with tertiary amines in their headgroups are disclosed in reference 5, the complete contents of which are incorporated herein by reference.

Liposomes of the invention can be formed from a single lipid or from a mixture of lipids, provided that at least one of the lipids has a pKa in the range of 5.0 to 7.6 (and, preferably, a tertiary amine). Within this pKa range, preferred lipids have a pKa of 5.5 to 6.7 e.g. between 5.6 and 6.8, between 5.6 and 6.3, between 5.6 and 6.0, between 5.5 and 6.2, or between 5.7 and 5.9. The pKa is the pH at which 50% of the lipids are charged, lying halfway between the point where the lipids are completely charged and the point where the lipids are completely uncharged. It can be measured in various ways, but is preferably measured using the method disclosed below in the section entitled "pKa measurement". The pKa typically should be measured for the lipid alone rather than for the lipid in the context of a mixture which also includes other lipids (e.g. not as performed in reference 6, which looks at the pKa of a SNALP rather than of the individual lipids).

Where a liposome of the invention is formed from a mixture of lipids, it is preferred that the proportion of those lipids which have a pKa within the desired range should be between 20-80% of the total amount of lipids e.g. between 30-70%, or between 40-60%. For instance, useful liposomes are shown below in which 40% or 60% of the total lipid is a lipid with a pKa in the desired range. The remainder can be made of e.g. cholesterol (e.g. 35-50% cholesterol) and/or DMG (optionally PEGylated) and/or DSPC. Such mixtures are used below. These % values are mole percentages.

A liposome may include an amphiphilic lipid whose hydrophilic portion is PEGylated (i.e. modified by covalent attachment of a polyethylene glycol). This modification can increase stability and prevent non-specific adsorption of the liposomes. For instance, lipids can be conjugated to PEG using techniques such as those disclosed in references 6 and 7. PEG provides the liposomes with a coat which can confer favourable pharmacokinetic characteristics. The combination of efficient encapsulation of a RNA (particularly a self-replicating RNA), a cationic lipid having a pKa in the range 5.0-7.6, and a PEGylated surface, allows for efficient delivery to multiple cell types (including both immune and non-immune cells), thereby eliciting a stronger and better immune response than when using quaternary amines without PEGylation. Various lengths of PEG can be used e.g. between 0.5-8 kDa.

Lipids used with the invention can be saturated or unsaturated. The use of at least one unsaturated lipid for preparing liposomes is preferred. FIG. 3 shows three useful unsaturated lipids. If an unsaturated lipid has two tails, both tails can be unsaturated, or it can have one saturated tail and one unsaturated tail.

A mixture of DSPC, DLinDMA, PEG-DMG and cholesterol is used in the examples. An independent aspect of the invention is a liposome comprising DSPC, DLinDMA, PEG-DMG & cholesterol. This liposome preferably encapsulates RNA, such as a self-replicating RNA e.g. encoding an immunogen.

Liposomal particles are usually divided into three groups: multilamellar vesicles (MLV); small unilamellar vesicles (SUV); and large unilamellar vesicles (LUV). MLVs have multiple bilayers in each vesicle, forming several separate aqueous compartments. SUVs and LUVs have a single bilayer encapsulating an aqueous core; SUVs typically have a diameter ≤50 nm, and LUVs have a diameter >50 nm. Liposomal particles of the invention are ideally LUVs with a diameter in the range of 50-220 nm. For a composition comprising a population of LUVs with different diameters: (i) at least 80% by number should have diameters in the range of 20-220 nm, (ii) the average diameter (Zav, by intensity) of the population is ideally in the range of 40-200 nm, and/or (iii) the diameters should have a polydispersity index <0.2. The liposome/RNA complexes of reference 1 are expected to have a diameter in the range of 600-800 nm and to have a high polydispersity. The liposome can be substantially spherical.

Techniques for preparing suitable liposomes are well known in the art e.g. see references 8 to 10. One useful method is described in reference 11 and involves mixing (i) an ethanolic solution of the lipids (ii) an aqueous solution of the nucleic acid and (iii) buffer, followed by mixing, equilibration, dilution and purification. Preferred liposomes of the invention are obtainable by this mixing process.

Mixing Process

As mentioned above, the invention provides a process for preparing a RNA-containing liposome, comprising steps of: (a) mixing RNA with a lipid at a pH which is below the lipid's pKa but is above 4.5; then (b) increasing the pH to be above the lipid's pKa.

Thus a cationic lipid is positively charged during liposome formation in step (a), but the pH change thereafter means that the majority (or all) of the positively charged groups become neutral. This process is advantageous for preparing liposomes of the invention, and by avoiding a pH below 4.5 during step (a) the stability of the encapsulated RNA is improved.

The pH in step (a) is above 4.5, and is ideally above 4.8. Using a pH in the range of 5.0 to 6.0, or in the range of 5.0 to 5.5, can provide suitable liposomes.

The increased pH in step (b) is above the lipid's pKa. The pH is ideally increased to a pH less than 9, and preferably less than 8. Depending on the lipid's pKa, the pH in step (b) may thus be increased to be within the range of 6 to 8 e.g. to pH 6.5±0.3. The pH increase of step (b) can be achieved by transferring the liposomes into a suitable buffer e.g. into phosphate-buffered saline. The pH increase of step (b) is ideally performed after liposome formation has taken place.

RNA used in step (a) can be in aqueous solution, for mixing with an organic solution of the lipid (e.g. an ethanolic solution, as in reference 11). The mixture can then be diluted to form liposomes, after which the pH can be increased in step (b).

The RNA

The invention is useful for in vivo delivery of RNA which encodes an immunogen. The RNA is translated by non-immune cells at the delivery site, leading to expression of the immunogen, and it also causes immune cells to secrete type I interferons and/or pro-inflammatory cytokines which provide a local adjuvant effect. The non-immune cells may also secrete type I interferons and/or pro-inflammatory cytokines in response to the RNA.

The RNA is +-stranded, and so it can be translated by the non-immune cells without needing any intervening replication steps such as reverse transcription. It can also bind to TLR7 receptors expressed by immune cells, thereby initiating an adjuvant effect.

Preferred +-stranded RNAs are self-replicating. A self-replicating RNA molecule (replicon) can, when delivered to a vertebrate cell even without any proteins, lead to the production of multiple daughter RNAs by transcription from itself (via an antisense copy which it generates from itself). A self-replicating RNA molecule is thus typically a +-strand molecule which can be directly translated after delivery to a cell, and this translation provides a RNA-dependent RNA polymerase which then produces both antisense and sense transcripts from the delivered RNA. Thus the delivered RNA leads to the production of multiple daughter RNAs. These daughter RNAs, as well as collinear subgenomic transcripts, may be translated themselves to provide in situ expression of an encoded immunogen, or may be transcribed to provide further transcripts with the same sense as the delivered RNA which are translated to provide in situ expression of the immunogen. The overall results of this sequence of transcriptions is a huge amplification in the number of the introduced replicon RNAs and so the encoded immunogen becomes a major polypeptide product of the cells.

As shown below, a self-replicating activity is not required for a RNA to provide an adjuvant effect, although it can enhance post-transfection secretion of cytokines. The self-replicating activity is particularly useful for achieving high level expression of the immunogen by non-immune cells. It can also enhance apoptosis of the non-immune cells.

One suitable system for achieving self-replication is to use an alphavirus-based RNA replicon. These +-stranded replicons are translated after delivery to a cell to give of a replicase (or replicase-transcriptase). The replicase is translated as a polyprotein which auto-cleaves to provide a replication complex which creates genomic --strand copies of the +-strand delivered RNA. These --strand transcripts can themselves be transcribed to give further copies of the +-stranded parent RNA and also to give a subgenomic transcript which encodes the immunogen. Translation of the subgenomic transcript thus leads to in situ expression of the immunogen by the infected cell. Suitable alphavirus replicons can use a replicase from a sindbis virus, a semliki forest virus, an eastern equine encephalitis virus, a venezuelan equine encephalitis virus, etc. Mutant or wild-type virus sequences can be used e.g. the attenuated TC83 mutant of VEEV has been used in replicons, as disclosed in reference 12.

A preferred self-replicating RNA molecule thus encodes (i) a RNA-dependent RNA polymerase which can transcribe RNA from the self-replicating RNA molecule and (ii) an immunogen. The polymerase can be an alphavirus replicase e.g. comprising one or more of alphavirus proteins nsP1, nsP2, nsP3 and nsP4.

Whereas natural alphavirus genomes encode structural virion proteins in addition to the non-structural replicase polyprotein, it is preferred that a self-replicating RNA molecule of the invention does not encode alphavirus structural proteins. Thus a preferred self-replicating RNA can lead to the production of genomic RNA copies of itself in a cell, but not to the production of RNA-containing virions. The inability to produce these virions means that, unlike a wild-type alphavirus, the self-replicating RNA molecule cannot perpetuate itself in infectious form. The alphavirus structural proteins which are necessary for perpetuation in wild-type viruses are absent from self-replicating RNAs of the invention and their place is taken by gene(s) encoding the immunogen of interest, such that the subgenomic transcript encodes the immunogen rather than the structural alphavirus virion proteins.

Thus a self-replicating RNA molecule useful with the invention may have two open reading frames. The first (5') open reading frame encodes a replicase; the second (3') open reading frame encodes an immunogen. In some embodiments the RNA may have additional (e.g. downstream) open reading frames e.g. to encode further immunogens (see below) or to encode accessory polypeptides.

A self-replicating RNA molecule can have a 5' sequence which is compatible with the encoded replicase.

Self-replicating RNA molecules can have various lengths but they are typically 5000-25000 nucleotides long e.g. 8000-15000 nucleotides, or 9000-12000 nucleotides. Thus the RNA is longer than seen in siRNA delivery.

A RNA molecule useful with the invention may have a 5' cap (e.g. a 7-methylguanosine). This cap can enhance in vivo translation of the RNA.

The 5' nucleotide of a RNA molecule useful with the invention may have a 5' triphosphate group. In a capped RNA this may be linked to a 7-methylguanosine via a 5'-to-5' bridge. A 5' triphosphate can enhance RIG-I binding and thus promote adjuvant effects.

A RNA molecule may have a 3' poly-A tail. It may also include a poly-A polymerase recognition sequence (e.g. AAUAAA) near its 3' end.

A RNA molecule useful with the invention will typically be single-stranded. Single-stranded RNAs can generally initiate an adjuvant effect by binding to TLR7, TLR8, RNA helicases and/or PKR. RNA delivered in double-stranded form (dsRNA) can bind to TLR3, and this receptor can also be triggered by dsRNA which is formed either during replication of a single-stranded RNA or within the secondary structure of a single-stranded RNA.

A RNA molecule useful with the invention can conveniently be prepared by in vitro transcription (IVT). IVT can use a (cDNA) template created and propagated in plasmid form in bacteria, or created synthetically (for example by gene synthesis and/or polymerase chain-reaction (PCR) engineering methods). For instance, a DNA-dependent RNA polymerase (such as the bacteriophage T7, T3 or SP6 RNA polymerases) can be used to transcribe the RNA from a DNA template. Appropriate capping and poly-A addition reactions can be used as required (although the replicon's poly-A is usually encoded within the DNA template). These RNA polymerases can have stringent requirements for the transcribed 5' nucleotide(s) and in some embodiments these requirements must be matched with the requirements of the encoded replicase, to ensure that the IVT-transcribed RNA can function efficiently as a substrate for its self-encoded replicase.

As discussed in reference 13, the self-replicating RNA can include (in addition to any 5' cap structure) one or more nucleotides having a modified nucleobase. Thus the RNA can comprise m5C (5-methylcytidine), m5U (5-methyluridine), m6A (N6-methyladenosine), s2U (2-thiouridine), Um (2'-O-methyluridine), m1A (1-methyladenosine); m2A (2-methyladenosine); Am (2'-O-methyladenosine); ms2m6A (2-methylthio-N6-methyladenosine); i6A (N6-isopentenyladenosine); ms2i6A (2-methylthio-N6isopentenyladenosine); io6A (N6-(cis-hydroxyisopentenyl)adenosine); ms2io6A (2-methylthio-N6-(cis-hydroxyisopentenyl) adenosine); g6A (N6-glycinylcarbamoyladenosine); t6A (N6-threonyl carbamoyladenosine); ms2t6A (2-methylthio-N6-threonyl carbamoyladenosine); m6t6A (N6-methyl-N6-threonylcarbamoyladenosine); hn6A (N6.-hydroxynorvalylcarbamoyl adenosine); ms2hn6A (2-methylthio-N6-hydroxynorvalyl carbamoyladenosine); Ar(p) (2'-O-ribosyladenosine (phosphate)); I (inosine); m1I (1-methylinosine); m'Im (1,2'-O-dimethylinosine); m3C (3-methylcytidine); Cm (2T-O-methylcytidine); s2C (2-thiocytidine); ac4C (N4-acetylcytidine); f5C (5-fonnylcytidine); m5Cm (5,2-O-dimethylcytidine); ac4Cm (N4acetyl2TOmethylcytidine); k2C (lysidine); m1G (1-methylguanosine); m2G (N2-methylguanosine); m7G (7-methylguanosine); Gm (2'-O-methylguanosine); m22G (N2,N2-dimethylguanosine); m2Gm (N2,2'-O-dimethylguanosine); m22Gm (N2,N2,2'-O-trimethylguanosine); Gr(p) (2'-O-ribosylguanosine (phosphate)); yW (wybutosine); o2yW (peroxywybutosine); OHyW (hydroxywybutosine); OHyW* (undermodified hydroxywybutosine); imG (wyosine); mimG (methylguanosine); Q (queuosine); oQ (epoxyqueuosine); galQ (galtactosyl-queuosine); manQ (mannosyl-queuosine); preQo (7-cyano-7-deazaguanosine); preQi (7-aminomethyl-7-deazaguanosine); G (archaeosine); D (dihydrouridine); m5Um (5,2'-O-dimethyluridine); s4U (4-thiouridine); m5s2U (5-methyl-2-thiouridine); s2Um (2-thio-2'-O-methyluridine); acp3U (3-(3-amino-3-carboxypropyl)uridine); ho5U (5-hydroxyuridine); mo5U (5-methoxyuridine); cmo5U (uridine 5-oxyacetic acid); mcmo5U (uridine 5-oxyacetic acid methyl ester); chm5U (5-(carboxyhydroxymethyl)uridine)); mchm5U (5-(carboxyhydroxymethyl)uridine methyl ester); mcm5U (5-methoxycarbonyl methyluridine); mcm5Um (S-methoxycarbonylmethyl-2-O-methyluridine); mcm5s2U (5-methoxycarbonylmethyl-2-thiouridine); nm5s2U (5-aminomethyl-2-thiouridine); mnm5U (5-methylaminomethyluridine); mnm5s2U (5-methylaminomethyl-2-thiouridine); mnm5se2U (5-methylaminomethyl-2-selenouridine); ncm5U (5-carbamoylmethyl uridine); ncm5Um (5-carbamoylmethyl-2'-O-methyluridine); cmnm5U (5-carboxymethylaminomethyluridine); cnmm5Um (5-carboxymethylaminomethyl-2-L-O-methyluridine); cmnm5s2U (5-carboxymethylaminomethyl-2-thiouridine); m62A (N6,N6-dimethyladenosine); Tm (2'-O-methylinosine); m4C (N4-methylcytidine); m4Cm (N4,2-O-dimethylcytidine); hm5C (5-hydroxymethylcytidine); m3U (3-methyluridine); cm5U (5-carboxymethyluridine); m6Am (N6,T-O-dimethyladenosine); rn62Am (N6,N6,O-2-trimethyladenosine); m2'7G (N2,7-dimethylguanosine); m2'2'7G (N2,N2,7-trimethylguanosine); m3Um (3,2T-O-dimethyluridine); m5D (5-methyldihydrouridine); f5Cm (5-formyl-2'-O-methylcytidine); m1Gm (1,2'-O-dimethylguanosine); m'Am (1,2-O-dimethyl adenosine) irinomethyluridine); tm5s2U (S-taurinomethyl-2-thiouridine)); imG-14 (4-demethyl guanosine); imG2 (isoguanosine); or ac6A (N6-acetyladenosine), hypoxanthine, inosine, 8-oxo-adenine, 7-substituted derivatives thereof, dihydrouracil, pseudouracil, 2-thiouracil, 4-thiouracil, 5-aminouracil, 5-(C1-C6)-alkyluracil, 5-methyluracil, 5-(C2-C6)-alkenyluracil, 5-(C2-C6)-alkynyluracil, 5-(hydroxymethyl)uracil, 5-chlorouracil, 5-fluorouracil, 5-bromouracil, 5-hydroxycytosine, 5-(C1-

C6)-alkylcytosine, 5-methylcytosine, 5-(C2-C6)-alkenylcytosine, 5-(C2-C6)-alkynylcytosine, 5-chlorocytosine, 5-fluorocytosine, 5-bromocytosine, N2-dimethylguanine, 7-deazaguanine, 8-azaguanine, 7-deaza-7-substituted guanine, 7-deaza-7-(C2-C6)alkynylguanine, 7-deaza-8-substituted guanine, 8-hydroxyguanine, 6-thioguanine, 8-oxoguanine, 2-aminopurine, 2-amino-6-chloropurine, 2,4-diaminopurine, 2,6-diaminopurine, 8-azapurine, substituted 7-deazapurine, 7-deaza-7-substituted purine, 7-deaza-8-substituted purine, or an abasic nucleotide. For instance, a self-replicating RNA can include one or more modified pyrimidine nucleobases, such as pseudouridine and/or 5-methylcytosine residues. In some embodiments, however, the RNA includes no modified nucleobases, and may include no modified nucleotides i.e. all of the nucleotides in the RNA are standard A, C, G and U ribonucleotides (except for any 5' cap structure, which may include a 7'-methylguanosine). In other embodiments, the RNA may include a 5' cap comprising a 7'-methylguanosine, and the first 1, 2 or 3 5' ribonucleotides may be methylated at the 2' position of the ribose.

A RNA used with the invention ideally includes only phosphodiester linkages between nucleosides, but in some embodiments it can contain phosphoramidate, phosphorothioate, and/or methylphosphonate linkages.

Ideally, a liposome includes fewer than 10 different species of RNA e.g. 5, 4, 3, or 2 different species; most preferably, a liposome includes a single RNA species i.e. all RNA molecules in the liposome have the same sequence and same length.

The amount of RNA per liposome can vary. The number of individual self-replicating RNA molecules per liposome is typically ≤50 e.g. <20, <10, <5, or 1-4 per liposome.

The Immunogen

RNA molecules used with the invention encode a polypeptide immunogen. After administration of the liposomes the RNA is translated in vivo and the immunogen can elicit an immune response in the recipient. The immunogen may elicit an immune response against a bacterium, a virus, a fungus or a parasite (or, in some embodiments, against an allergen; and in other embodiments, against a tumor antigen). The immune response may comprise an antibody response (usually including IgG) and/or a cell-mediated immune response. The polypeptide immunogen will typically elicit an immune response which recognises the corresponding bacterial, viral, fungal or parasite (or allergen or tumour) polypeptide, but in some embodiments the polypeptide may act as a mimotope to elicit an immune response which recognises a bacterial, viral, fungal or parasite saccharide. The immunogen will typically be a surface polypeptide e.g. an adhesin, a hemagglutinin, an envelope glycoprotein, a spike glycoprotein, etc.

Self-replicating RNA molecules can encode a single polypeptide immunogen or multiple polypeptides. Multiple immunogens can be presented as a single polypeptide immunogen (fusion polypeptide) or as separate polypeptides. If immunogens are expressed as separate polypeptides then one or more of these may be provided with an upstream IRES or an additional viral promoter element. Alternatively, multiple immunogens may be expressed from a polyprotein that encodes individual immunogens fused to a short autocatalytic protease (e.g. foot-and-mouth disease virus 2A protein), or as inteins.

Unlike references 1 and 14, the RNA encodes an immunogen. For the avoidance of doubt, the invention does not encompass RNA which encodes a firefly luciferase or which encodes a fusion protein of *E. coli* β-galactosidase or which encodes a green fluorescent protein (GFP). Also, the RNA is not total mouse thymus RNA.

In some embodiments the immunogen elicits an immune response against one of these bacteria:

*Neisseria meningitidis*: useful immunogens include, but are not limited to, membrane proteins such as adhesins, autotransporters, toxins, iron acquisition proteins, and factor H binding protein. A combination of three useful polypeptides is disclosed in reference 15.

*Streptococcus pneumoniae*: useful polypeptide immunogens are disclosed in reference 16. These include, but are not limited to, the RrgB pilus subunit, the beta-N-acetyl-hexosaminidase precursor (spr0057), spr0096, General stress protein GSP-781 (spr2021, SP2216), serine/threonine kinase StkP (SP1732), and pneumococcal surface adhesin PsaA.

*Streptococcus pyogenes*: useful immunogens include, but are not limited to, the polypeptides disclosed in references 17 and 18.

*Moraxella catarrhalis*.

*Bordetella pertussis*: Useful pertussis immunogens include, but are not limited to, pertussis toxin or toxoid (PT), filamentous haemagglutinin (FHA), pertactin, and agglutinogens 2 and 3.

*Staphylococcus aureus*: Useful immunogens include, but are not limited to, the polypeptides disclosed in reference 19, such as a hemolysin, esxA, esxB, ferrichrome-binding protein (sta006) and/or the sta011 lipoprotein.

*Clostridium tetani*: the typical immunogen is tetanus toxoid.

*Cornynebacterium diphtheriae*: the typical immunogen is diphtheria toxoid.

*Haemophilus influenzae*: Useful immunogens include, but are not limited to, the polypeptides disclosed in references 20 and 21.

*Pseudomonas aeruginosa*

*Streptococcus agalactiae*: useful immunogens include, but are not limited to, the polypeptides disclosed in reference 17.

*Chlamydia trachomatis*: Useful immunogens include, but are not limited to, PepA, LcrE, ArtJ, DnaK, CT398, OmpH-like, L7/L12, OmcA, AtoS, CT547, Eno, HtrA and MurG (e.g. as disclosed in reference 22. LcrE as disclosed in reference 23 and HtrA as disclosed in reference 24 are two preferred immunogens.

*Chlamydia pneumoniae*: Useful immunogens include, but are not limited to, the polypeptides disclosed in reference 25.

*Helicobacter pylori*: Useful immunogens include, but are not limited to, CagA, VacA, NAP, and/or urease as disclosed in reference 26.

*Escherichia coli*: Useful immunogens include, but are not limited to, immunogens derived from enterotoxigenic *E. coli* (ETEC), enteroaggregative *E. coli* (EAggEC), diffusely adhering *E. coli* (DAEC), enteropathogenic *E. coli* (EPEC), extraintestinal pathogenic *E. coli* (ExPEC) and/or enterohemorrhagic *E. coli* (EHEC). ExPEC strains include uropathogenic *E. coli* (UPEC) and meningitis/sepsis-associated *E. coli* (MNEC). Useful UPEC polypeptide immunogens are disclosed in references 27 and 28. Useful MNEC immunogens are disclosed in reference 29. A useful immunogen for several *E. coli* types is AcfD as disclosed in reference 30.

*Bacillus anthracis*

*Yersinia pestis*: Useful immunogens include, but are not limited to, those disclosed in references 31 and 32.

*Staphylococcus epidermis*
*Clostridium perfringens* or *Clostridium botulinums*
*Legionella pneumophila*
*Coxiella burnetii*
*Brucella*, such as *B. abortus*, *B. canis*, *B. melitensis*, *B. neotomae*, *B. ovis*, *B. suis*, *B. pinnipediae*.
*Francisella*, such as *F. novicida*, *F. philomiragia*, *F. tularensis*.
*Neisseria gonorrhoeae*
*Treponema pallidum*
*Haemophilus ducreyi*
*Enterococcus faecalis* or *Enterococcus faecium*
*Staphylococcus saprophyticus*
*Yersinia enterocolitica*
*Mycobacterium tuberculosis*
*Rickettsia*
*Listeria monocytogenes*
*Vibrio cholerae*
*Salmonella typhi*
*Borrelia burgdorferi*
*Porphyromonas gingivalis*
*Klebsiella*

In some embodiments the immunogen elicits an immune response against one of these viruses:

Orthomyxovirus: Useful immunogens can be from an influenza A, B or C virus, such as the hemagglutinin, neuraminidase or matrix M2 proteins. Where the immunogen is an influenza A virus hemagglutinin it may be from any subtype e.g. H1, H2, H3, H4, H5, H6, H7, H8, H9, H10, H11, H12, H13, H14, H15 or H16.

Paramyxoviridae viruses: Viral immunogens include, but are not limited to, those derived from Pneumoviruses (e.g. respiratory syncytial virus, RSV), Rubulaviruses (e.g. mumps virus), Paramyxoviruses (e.g. parainfluenza virus), Metapneumoviruses and Morbilliviruses (e.g. measles).

Poxviridae: Viral immunogens include, but are not limited to, those derived from Orthopoxvirus such as *Variola vera*, including but not limited to, *Variola major* and *Variola minor.*

Picornavirus: Viral immunogens include, but are not limited to, those derived from Picornaviruses, such as Enteroviruses, Rhinoviruses, Heparnavirus, Cardioviruses and Aphthoviruses. In one embodiment, the enterovirus is a poliovirus e.g. a type 1, type 2 and/or type 3 poliovirus. In another embodiment, the enterovirus is an EV71 enterovirus. In another embodiment, the enterovirus is a coxsackie A or B virus.

Bunyavirus: Viral immunogens include, but are not limited to, those derived from an Orthobunyavirus, such as California encephalitis virus, a Phlebovirus, such as Rift Valley Fever virus, or a Nairovirus, such as Crimean-Congo hemorrhagic fever virus.

Heparnavirus: Viral immunogens include, but are not limited to, those derived from a Heparnavirus, such as hepatitis A virus (HAV).

Filovirus: Viral immunogens include, but are not limited to, those derived from a filovirus, such as an Ebola virus (including a Zaire, Ivory Coast, Reston or Sudan ebolavirus) or a Marburg virus.

Togavirus: Viral immunogens include, but are not limited to, those derived from a Togavirus, such as a Rubivirus, an Alphavirus, or an Arterivirus. This includes rubella virus.

Flavivirus: Viral immunogens include, but are not limited to, those derived from a Flavivirus, such as Tick-borne encephalitis (TBE) virus, Dengue (types 1, 2, 3 or 4) virus, Yellow Fever virus, Japanese encephalitis virus, Kyasanur Forest Virus, West Nile encephalitis virus, St. Louis encephalitis virus, Russian spring-summer encephalitis virus, Powassan encephalitis virus.

Pestivirus: Viral immunogens include, but are not limited to, those derived from a Pestivirus, such as Bovine viral diarrhea (BVDV), Classical swine fever (CSFV) or Border disease (BDV).

Hepadnavirus: Viral immunogens include, but are not limited to, those derived from a Hepadnavirus, such as Hepatitis B virus. A composition can include hepatitis B virus surface antigen (HBsAg).

Other hepatitis viruses: A composition can include an immunogen from a hepatitis C virus, delta hepatitis virus, hepatitis E virus, or hepatitis G virus.

Rhabdovirus: Viral immunogens include, but are not limited to, those derived from a Rhabdovirus, such as a Lyssavirus (e.g. a Rabies virus) and Vesiculovirus (VSV).

Caliciviridae: Viral immunogens include, but are not limited to, those derived from Calciviridae, such as Norwalk virus (Norovirus), and Norwalk-like Viruses, such as Hawaii Virus and Snow Mountain Virus.

Coronavirus: Viral immunogens include, but are not limited to, those derived from a SARS coronavirus, avian infectious bronchitis (IBV), Mouse hepatitis virus (MHV), and Porcine transmissible gastroenteritis virus (TGEV). The coronavirus immunogen may be a spike polypeptide.

Retrovirus: Viral immunogens include, but are not limited to, those derived from an Oncovirus, a Lentivirus (e.g. HIV-1 or HIV-2) or a Spumavirus.

Reovirus: Viral immunogens include, but are not limited to, those derived from an Orthoreovirus, a Rotavirus, an Orbivirus, or a Coltivirus.

Parvovirus: Viral immunogens include, but are not limited to, those derived from Parvovirus B19.

Herpesvirus: Viral immunogens include, but are not limited to, those derived from a human herpesvirus, such as, by way of example only, Herpes Simplex Viruses (HSV) (e.g. HSV types 1 and 2), Varicella-zoster virus (VZV), Epstein-Barr virus (EBV), Cytomegalovirus (CMV), Human Herpesvirus 6 (HHV6), Human Herpesvirus 7 (HHV7), and Human Herpesvirus 8 (HHV8).

Papovaviruses: Viral immunogens include, but are not limited to, those derived from Papillomaviruses and Polyomaviruses. The (human) papillomavirus may be of serotype 1, 2, 4, 5, 6, 8, 11, 13, 16, 18, 31, 33, 35, 39, 41, 42, 47, 51, 57, 58, 63 or 65 e.g. from one or more of serotypes 6, 11, 16 and/or 18.

Adenovirus: Viral immunogens include those derived from adenovirus serotype 36 (Ad-36).

In some embodiments, the immunogen elicits an immune response against a virus which infects fish, such as: infectious salmon anemia virus (ISAV), salmon pancreatic disease virus (SPDV), infectious pancreatic necrosis virus (IPNV), channel catfish virus (CCV), fish lymphocystis disease virus (FLDV), infectious hematopoietic necrosis virus (IHNV), koi herpesvirus, salmon picorna-like virus (also known as picorna-like virus of atlantic salmon), landlocked salmon virus (LSV), atlantic salmon rotavirus (ASR), trout strawberry disease virus (TSD), coho salmon tumor virus (CSTV), or viral hemorrhagic septicemia virus (VHSV).

Fungal immunogens may be derived from Dermatophytres, including: *Epidermophyton floccusum, Microspo-*

*rum audouini, Microsporum canis, Microsporum distortum, Microsporum equinum, Microsporum gypseum, Microsporum nanum, Trichophyton concentricum, Trichophyton equinum, Trichophyton gallinae, Trichophyton gypseum, Trichophyton megnini, Trichophyton mentagrophytes, Trichophyton quinckeanum, Trichophyton rubrum, Trichophyton schoenleini, Trichophyton tonsurans, Trichophyton verrucosum, T verrucosum* var. *album,* var. *discoides,* var. *ochraceum, Trichophyton violaceum,* and/or *Trichophyton faviforme;* or from *Aspergillus fumigatus, Aspergillus flavus, Aspergillus niger, Aspergillus nidulans, Aspergillus terreus, Aspergillus sydowii, Aspergillus flavatus, Aspergillus glaucus, Blastoschizomyces capitatus, Candida albicans, Candida enolase, Candida tropicalis, Candida glabrata, Candida krusei, Candida parapsilosis, Candida stellatoidea, Candida kusei, Candida parakwsei, Candida lusitaniae, Candida pseudotropicalis, Candida guilliermondi, Cladosporium carrionii, Coccidioides immitis, Blastomyces dermatidis, Cryptococcus neoformans, Geotrichum clavatum, Histoplasma capsulatum, Klebsiella pneumoniae,* Microsporidia, *Encephalitozoon* spp., *Septata intestinalis* and *Enterocytozoon bieneusi;* the less common are *Brachiola* spp, *Microsporidium* spp., *Nosema* spp., *Pleistophora* spp., *Trachipleistophora* spp., *Vittaforma* spp *Paracoccidioides brasiliensis, Pneumocystis carinii, Pythiumn insidiosum, Pityrosporum ovale, Sacharomyces cerevisae, Saccharomyces boulardii, Saccharomyces pombe, Scedosporium apiosperum, Sporothrix schenckii, Trichosporon beigelii, Toxoplasma gondii, Penicillium marneffei, Malassezia* spp., *Fonsecaea* spp., *Wangiella* spp., *Sporothrix* spp., *Basidiobolus* spp., *Conidiobolus* spp., *Rhizopus* spp, *Mucor* spp, *Absidia* spp, *Mortierella* spp, *Cunninghamella* spp, *Saksenaea* spp., *Alternaria* spp, *Curvularia* spp, *Helminthosporium* spp, *Fusarium* spp, *Aspergillus* spp, *Penicillium* spp, *Monolinia* spp, *Rhizoctonia* spp, *Paecilomyces* spp, *Pithomyces* spp, and *Cladosporium* spp.

In some embodiments the immunogen elicits an immune response against a parasite from the *Plasmodium* genus, such as *P. falciparum, P. vivax, P. malariae* or *P. ovale.* Thus the invention may be used for immunising against malaria. In some embodiments the immunogen elicits an immune response against a parasite from the Caligidae family, particularly those from the *Lepeophtheirus* and *Caligus* genera e.g. sea lice such as *Lepeophtheirus salmonis* or *Caligus rogercresseyi.*

In some embodiments the immunogen elicits an immune response against: pollen allergens (tree-, herb, weed-, and grass pollen allergens); insect or arachnid allergens (inhalant, saliva and venom allergens, e.g. mite allergens, cockroach and midges allergens, hymenopthera venom allergens); animal hair and dandruff allergens (from e.g. dog, cat, horse, rat, mouse, etc.); and food allergens (e.g. a gliadin). Important pollen allergens from trees, grasses and herbs are such originating from the taxonomic orders of Fagales, Oleales, Pinales and platanaceae including, but not limited to, birch (*Betula*), alder (*Alnus*), hazel (*Corylus*), hornbeam (*Carpinus*) and olive (*Olea*), cedar (*Cryptomeria* and *Juniperus*), plane tree (*Platanus*), the order of Poales including grasses of the genera *Lolium, Phleum, Poa, Cynodon, Dactylis, Holcus, Phalaris, Secale,* and *Sorghum,* the orders of Asterales and Urticales including herbs of the genera *Ambrosia, Artemisia,* and *Parietaria.* Other important inhalation allergens are those from house dust mites of the genus *Dermatophagoides* and *Euroglyphus,* storage mite e.g. *Lepidoglyphys, Glycyphagus* and *Tyrophagus,* those from cockroaches, midges and fleas e.g. *Blatella, Periplaneta, Chironomus* and *Ctenocepphalides,* and those from mammals such as cat, dog and horse, venom allergens including such originating from stinging or biting insects such as those from the taxonomic order of Hymenoptera including bees (*Apidae*), wasps (*Vespidea*), and ants (*Formicoidae*).

In some embodiments the immunogen is a tumor antigen selected from: (a) cancer-testis antigens such as NY-ESO-1, SSX2, SCP1 as well as RAGE, BAGE, GAGE and MAGE family polypeptides, for example, GAGE-1, GAGE-2, MAGE-1, MAGE-2, MAGE-3, MAGE-4, MAGE-5, MAGE-6, and MAGE-12 (which can be used, for example, to address melanoma, lung, head and neck, NSCLC, breast, gastrointestinal, and bladder tumors; (b) mutated antigens, for example, p53 (associated with various solid tumors, e.g., colorectal, lung, head and neck cancer), p21/Ras (associated with, e.g., melanoma, pancreatic cancer and colorectal cancer), CDK4 (associated with, e.g., melanoma), MUM1 (associated with, e.g., melanoma), caspase-8 (associated with, e.g., head and neck cancer), CIA 0205 (associated with, e.g., bladder cancer), HLA-A2-R1701, beta catenin (associated with, e.g., melanoma), TCR (associated with, e.g., T-cell non-Hodgkins lymphoma), BCR-abl (associated with, e.g., chronic myelogenous leukemia), triosephosphate isomerase, KIA 0205, CDC-27, and LDLR-FUT; (c) over-expressed antigens, for example, Galectin 4 (associated with, e.g., colorectal cancer), Galectin 9 (associated with, e.g., Hodgkin's disease), proteinase 3 (associated with, e.g., chronic myelogenous leukemia), WT 1 (associated with, e.g., various leukemias), carbonic anhydrase (associated with, e.g., renal cancer), aldolase A (associated with, e.g., lung cancer), PRAME (associated with, e.g., melanoma), HER-2/neu (associated with, e.g., breast, colon, lung and ovarian cancer), mammaglobin, alpha-fetoprotein (associated with, e.g., hepatoma), KSA (associated with, e.g., colorectal cancer), gastrin (associated with, e.g., pancreatic and gastric cancer), telomerase catalytic protein, MUC-1 (associated with, e.g., breast and ovarian cancer), G-250 (associated with, e.g., renal cell carcinoma), p53 (associated with, e.g., breast, colon cancer), and carcinoembryonic antigen (associated with, e.g., breast cancer, lung cancer, and cancers of the gastrointestinal tract such as colorectal cancer); (d) shared antigens, for example, melanoma-melanocyte differentiation antigens such as MART-1/Melan A, gp100, MC1R, melanocyte-stimulating hormone receptor, tyrosinase, tyrosinase related protein-1/TRP1 and tyrosinase related protein-2/ TRP2 (associated with, e.g., melanoma); (e) prostate associated antigens such as PAP, PSA, PSMA, PSH-P1, PSM-P1, PSM-P2, associated with e.g., prostate cancer; (f) immunoglobulin idiotypes (associated with myeloma and B cell lymphomas, for example). In certain embodiments, tumor immunogens include, but are not limited to, p15, Hom/Mel-40, H-Ras, E2A-PRL, H4-RET, IGH-IGK, MYL-RAR, Epstein Barr virus antigens, EBNA, human papillomavirus (HPV) antigens, including E6 and E7, hepatitis B and C virus antigens, human T-cell lymphotropic virus antigens, TSP-180, p185erbB2, p180erbB-3, c-met, mn-23H1, TAG-72-4, CA19-9, CA72-4, CAM 17.1, NuMa, K-ras, p16, TAGE, PSCA, CT7, 43-9F, 5T4, 791 Tgp72, beta-HCG, BCA225, BTAA, CA 125, CA 15-3 (CA 27.29\BCAA), CA 195, CA 242, CA-50, CAM43, CD68\KP1, CO-029, FGF-5, Ga733 (EpCAM), HTgp-175, M344, MA-50, MG7-Ag, MOV18, NB/70K, NY-CO-1, RCAS1, SDCCAG16, TA-90 (Mac-2 binding protein/cyclophilin C-associated protein), TAAL6, TAG72, TLP, TPS, and the like.

Pharmaceutical Compositions

Liposomes of the invention are useful as components in pharmaceutical compositions for immunising subjects against various diseases. These compositions will typically include a pharmaceutically acceptable carrier in addition to the liposomes. A thorough discussion of pharmaceutically acceptable carriers is available in reference 33.

A pharmaceutical composition of the invention may include one or more small molecule immunopotentiators. For example, the composition may include a TLR2 agonist (e.g. Pam3CSK4), a TLR4 agonist (e.g. an aminoalkyl glucosaminide phosphate, such as E6020), a TLR7 agonist (e.g. imiquimod), a TLR8 agonist (e.g. resiquimod) and/or a TLR9 agonist (e.g. IC31). Any such agonist ideally has a molecular weight of <2000 Da. Where a RNA is encapsulated, in some embodiments such agonist(s) are also encapsulated with the RNA, but in other embodiments they are unencapsulated. Where a RNA is adsorbed to a particle, in some embodiments such agonist(s) are also adsorbed with the RNA, but in other embodiments they are unadsorbed.

Pharmaceutical compositions of the invention may include the liposomes in plain water (e.g. w.f.i.) or in a buffer e.g. a phosphate buffer, a Tris buffer, a borate buffer, a succinate buffer, a histidine buffer, or a citrate buffer. Buffer salts will typically be included in the 5-20 mM range.

Pharmaceutical compositions of the invention may have a pH between 5.0 and 9.5 e.g. between 6.0 and 8.0.

Compositions of the invention may include sodium salts (e.g. sodium chloride) to give tonicity. A concentration of 10±2 mg/ml NaCl is typical e.g. about 9 mg/ml.

Compositions of the invention may include metal ion chelators. These can prolong RNA stability by removing ions which can accelerate phosphodiester hydrolysis. Thus a composition may include one or more of EDTA, EGTA, BAPTA, pentetic acid, etc. Such chelators are typically present at between 10-500 µM e.g. 0.1 mM. A citrate salt, such as sodium citrate, can also act as a chelator, while advantageously also providing buffering activity.

Pharmaceutical compositions of the invention may have an osmolality of between 200 mOsm/kg and 400 mOsm/kg, e.g. between 240-360 mOsm/kg, or between 290-310 mOsm/kg.

Pharmaceutical compositions of the invention may include one or more preservatives, such as thiomersal or 2-phenoxyethanol. Mercury-free compositions are preferred, and preservative-free vaccines can be prepared.

Pharmaceutical compositions of the invention are preferably sterile.

Pharmaceutical compositions of the invention are preferably non-pyrogenic e.g. containing <1 EU (endotoxin unit, a standard measure) per dose, and preferably <0.1 EU per dose.

Pharmaceutical compositions of the invention are preferably gluten free.

Pharmaceutical compositions of the invention may be prepared in unit dose form. In some embodiments a unit dose may have a volume of between 0.1-1.0 ml e.g. about 0.5 ml.

The compositions may be prepared as injectables, either as solutions or suspensions. The composition may be prepared for pulmonary administration e.g. by an inhaler, using a fine spray. The composition may be prepared for nasal, aural or ocular administration e.g. as spray or drops. Injectables for intramuscular administration are typical.

Compositions comprise an immunologically effective amount of liposomes, as well as any other components, as needed. By 'immunologically effective amount', it is meant that the administration of that amount to an individual, either in a single dose or as part of a series, is effective for treatment or prevention. This amount varies depending upon the health and physical condition of the individual to be treated, age, the taxonomic group of individual to be treated (e.g. non-human primate, primate, etc.), the capacity of the individual's immune system to synthesise antibodies, the degree of protection desired, the formulation of the vaccine, the treating doctor's assessment of the medical situation, and other relevant factors. It is expected that the amount will fall in a relatively broad range that can be determined through routine trials. The liposome and RNA content of compositions of the invention will generally be expressed in terms of the amount of RNA per dose. A preferred dose has ≤100 µg RNA (e.g. from 10-100 µg, such as about 10 µg, 25 µg, 50 µg, 75 µg or 100 µg), but expression can be seen at much lower levels e.g. ≤1 µg/dose, ≤100 ng/dose, ≤10 ng/dose, ≤1 ng/dose, etc The invention also provides a delivery device (e.g. syringe, nebuliser, sprayer, inhaler, dermal patch, etc.) containing a pharmaceutical composition of the invention. This device can be used to administer the composition to a vertebrate subject.

Liposomes of the invention do not include ribosomes.

Methods of Treatment and Medical Uses

In contrast to the particles disclosed in reference 14, liposomes and pharmaceutical compositions of the invention are for in vivo use for eliciting an immune response against an immunogen of interest.

The invention provides a method for raising an immune response in a vertebrate comprising the step of administering an effective amount of a liposome or pharmaceutical composition of the invention. The immune response is preferably protective and preferably involves antibodies and/or cell-mediated immunity. The method may raise a booster response.

The invention also provides a liposome or pharmaceutical composition of the invention for use in a method for raising an immune response in a vertebrate.

The invention also provides the use of a liposome of the invention in the manufacture of a medicament for raising an immune response in a vertebrate.

By raising an immune response in the vertebrate by these uses and methods, the vertebrate can be protected against various diseases and/or infections e.g. against bacterial and/or viral diseases as discussed above. The liposomes and compositions are immunogenic, and are more preferably vaccine compositions. Vaccines according to the invention may either be prophylactic (i.e. to prevent infection) or therapeutic (i.e. to treat infection), but will typically be prophylactic.

The vertebrate is preferably a mammal, such as a human or a large veterinary mammal (e.g. horses, cattle, deer, goats, pigs). Where the vaccine is for prophylactic use, the human is preferably a child (e.g. a toddler or infant) or a teenager; where the vaccine is for therapeutic use, the human is preferably a teenager or an adult. A vaccine intended for children may also be administered to adults e.g. to assess safety, dosage, immunogenicity, etc.

Vaccines prepared according to the invention may be used to treat both children and adults. Thus a human patient may be less than 1 year old, less than 5 years old, 1-5 years old, 5-15 years old, 15-55 years old, or at least 55 years old. Preferred patients for receiving the vaccines are the elderly (e.g. ≥50 years old, ≥60 years old, and preferably ≥65 years), the young (e.g. ≤5 years old), hospitalised patients, healthcare workers, armed service and military personnel, pregnant women, the chronically ill, or immunodeficient patients. The vaccines are not suitable solely for these groups, however, and may be used more generally in a population.

Compositions of the invention will generally be administered directly to a patient. Direct delivery may be accomplished by parenteral injection (e.g. subcutaneously, intraperitoneally, intravenously, intramuscularly, intradermally, or to the interstitial space of a tissue; unlike reference 1, intraglossal injection is not typically used with the present invention). Alternative delivery routes include rectal, oral (e.g. tablet, spray), buccal, sublingual, vaginal, topical, transdermal or transcutaneous, intranasal, ocular, aural, pulmonary or other mucosal administration. Intradermal and intramuscular administration are two preferred routes. Injection may be via a needle (e.g. a hypodermic needle), but needle-free injection may alternatively be used. A typical intramuscular dose is 0.5 ml.

The invention may be used to elicit systemic and/or mucosal immunity, preferably to elicit an enhanced systemic and/or mucosal immunity.

Dosage can be by a single dose schedule or a multiple dose schedule. Multiple doses may be used in a primary immunisation schedule and/or in a booster immunisation schedule. In a multiple dose schedule the various doses may be given by the same or different routes e.g. a parenteral prime and mucosal boost, a mucosal prime and parenteral boost, etc. Multiple doses will typically be administered at least 1 week apart (e.g. about 2 weeks, about 3 weeks, about 4 weeks, about 6 weeks, about 8 weeks, about 10 weeks, about 12 weeks, about 16 weeks, etc.). In one embodiment, multiple doses may be administered approximately 6 weeks, 10 weeks and 14 weeks after birth, e.g. at an age of 6 weeks, 10 weeks and 14 weeks, as often used in the World Health Organisation's Expanded Program on Immunisation ("EPI"). In an alternative embodiment, two primary doses are administered about two months apart, e.g. about 7, 8 or 9 weeks apart, followed by one or more booster doses about 6 months to 1 year after the second primary dose, e.g. about 6, 8, 10 or 12 months after the second primary dose. In a further embodiment, three primary doses are administered about two months apart, e.g. about 7, 8 or 9 weeks apart, followed by one or more booster doses about 6 months to 1 year after the third primary dose, e.g. about 6, 8, 10, or 12 months after the third primary dose.

General

The practice of the present invention will employ, unless otherwise indicated, conventional methods of chemistry, biochemistry, molecular biology, immunology and pharmacology, within the skill of the art. Such techniques are explained fully in the literature. See, e.g., references 34-40, etc.

The term "comprising" encompasses "including" as well as "consisting" e.g. a composition "comprising" X may consist exclusively of X or may include something additional e.g. X+Y.

The term "about" in relation to a numerical value x is optional and means, for example, x±10%.

The word "substantially" does not exclude "completely" e.g. a composition which is "substantially free" from Y may be completely free from Y. Where necessary, the word "substantially" may be omitted from the definition of the invention.

References to charge, to cations, to anions, to zwitterions, etc., are taken at pH 7.

TLR3 is the Toll-like receptor 3. It is a single membrane-spanning receptor which plays a key role in the innate immune system. Known TLR3 agonists include poly(I:C). "TLR3" is the approved HGNC name for the gene encoding this receptor, and its unique HGNC ID is HGNC:11849. The RefSeq sequence for the human TLR3 gene is GI:2459625.

TLR7 is the Toll-like receptor 7. It is a single membrane-spanning receptor which plays a key role in the innate immune system. Known TLR7 agonists include e.g. imiquimod. "TLR7" is the approved HGNC name for the gene encoding this receptor, and its unique HGNC ID is HGNC:15631. The RefSeq sequence for the human TLR7 gene is GI:67944638.

TLR8 is the Toll-like receptor 8. It is a single membrane-spanning receptor which plays a key role in the innate immune system. Known TLR8 agonists include e.g. resiquimod. "TLR8" is the approved HGNC name for the gene encoding this receptor, and its unique HGNC ID is HGNC:15632. The RefSeq sequence for the human TLR8 gene is GI:20302165.

The RIG-I-like receptor ("RLR") family includes various RNA helicases which play key roles in the innate immune system as disclosed in reference 41. RLR-1 (also known as RIG-I or retinoic acid inducible gene I) has two caspase recruitment domains near its N-terminus. The approved HGNC name for the gene encoding the RLR-1 helicase is "DDX58" (for DEAD (Asp-Glu-Ala-Asp) box polypeptide 58) and the unique HGNC ID is HGNC:19102. The RefSeq sequence for the human RLR-1 gene is GI:77732514. RLR-2 (also known as MDA5 or melanoma differentiation-associated gene 5) also has two caspase recruitment domains near its N-terminus. The approved HGNC name for the gene encoding the RLR-2 helicase is "IFIH1" (for interferon induced with helicase C domain 1) and the unique HGNC ID is HGNC:18873. The RefSeq sequence for the human RLR-2 gene is GI: 27886567. RLR-3 (also known as LGP2 or laboratory of genetics and physiology 2) has no caspase recruitment domains. The approved HGNC name for the gene encoding the RLR-3 helicase is "DHX58" (for DEXH (Asp-Glu-X-His) box polypeptide 58) and the unique HGNC ID is HGNC:29517. The RefSeq sequence for the human RLR-3 gene is GI:149408121.

PKR is a double-stranded RNA-dependent protein kinase. It plays a key role in the innate immune system. "EIF2AK2" (for eukaryotic translation initiation factor 2-alpha kinase 2) is the approved HGNC name for the gene encoding this enzyme, and its unique HGNC ID is HGNC:9437. The RefSeq sequence for the human PKR gene is GI:208431825.

BRIEF DESCRIPTION OF DRAWINGS

FIG. 7 shows anti-F IgG titers in animals receiving virion-packaged replicon (VRP or VSRP), 1 µg naked RNA, and 1 µg liposome-encapsulated RNA.

FIG. 8 shows anti-F IgG titers in animals receiving VRP, 1 µg naked RNA, and 0.1 µg or 1 µg liposome-encapsulated RNA.

FIG. 13 shows intracellular cytokine production after restimulation with synthetic peptides representing the major epitopes in the F protein, 4 weeks after a second dose. The y-axis shows the % cytokine+ of CD8+CD4−.

FIGS. 14A and 14B show F-specific IgG titers (mean $\log_{10}$ titers±std dev) over 63 days (FIG. 14A) and 210 days (FIG. 14B) after immunisation of calves. The three lines are easily distinguished at day 63 and are, from bottom to top: PBS negative control; liposome-delivered RNA; and the "Triangle 4" product.

MODES FOR CARRYING OUT THE INVENTION

RNA Replicons

Figure 1:
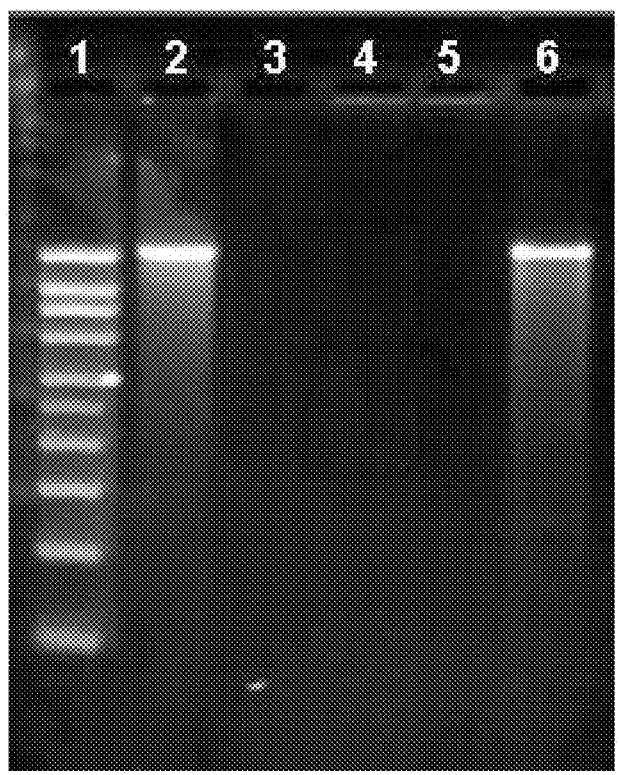
FIG. 1 shows a gel with stained RNA. Lanes show (1) markers (2) naked replicon (3) replicon after RNase treatment (4) replicon encapsulated in liposome (5) liposome after RNase treatment (6) liposome treated with RNase then subjected to phenol/chloroform extraction.

Various replicons are used below. In general these are based on a hybrid alphavirus genome with non-structural proteins from venezuelan equine encephalitis virus (VEEV), a packaging signal from sindbis virus, and a 3' UTR from Sindbis virus or a VEEV mutant. The replicon is about 10 kb long and has a poly-A tail.

Plasmid DNA encoding alphavirus replicons (named: pT7-mVEEV-FL.RSVF or A317; pT7-mVEEV-SEAP or A306; pSP6-VCR-GFP or A50) served as a template for synthesis of RNA in vitro. The replicons contain the alphavirus genetic elements required for RNA replication but lack those encoding gene products necessary for particle assembly; the structural proteins are instead replaced by a protein of interest (either a reporter, such as SEAP or GFP, or an immunogen, such as full-length RSV F protein) and so the replicons are incapable of inducing the generation of infectious particles. A bacteriophage (T7 or SP6) promoter upstream of the alphavirus cDNA facilitates the synthesis of the replicon RNA in vitro and a hepatitis delta virus (HDV) ribozyme immediately downstream of the poly(A)-tail generates the correct 3'-end through its self-cleaving activity.

Following linearization of the plasmid DNA downstream of the HDV ribozyme with a suitable restriction endonuclease, run-off transcripts were synthesized in vitro using T7 or SP6 bacteriophage derived DNA-dependent RNA polymerase. Transcriptions were performed for 2 hours at 37° C. in the presence of 7.5 mM (T7 RNA polymerase) or 5 mM (SP6 RNA polymerase) of each of the nucleoside triphosphates (ATP, CTP, GTP and UTP) following the instructions provided by the manufacturer (Ambion). Following transcription the template DNA was digested with TURBO DNase (Ambion). The replicon RNA was precipitated with LiCl and reconstituted in nuclease-free water. Uncapped RNA was capped post-transcriptionally with Vaccinia Capping Enzyme (VCE) using the ScriptCap m7G Capping System (Epicentre Biotechnologies) as outlined in the user manual; replicons capped in this way are given the "v" prefix e.g. vA317 is the A317 replicon capped by VCE. Post-transcriptionally capped RNA was precipitated with LiCl and reconstituted in nuclease-free water. The concentration of the RNA samples was determined by measuring $OD_{260nm}$. Integrity of the in vitro transcripts was confirmed by denaturing agarose gel electrophoresis.

Liposomal Encapsulation

RNA was encapsulated in liposomes made by the method of references 11 and 42. The liposomes were made of 10% DSPC (zwitterionic), 40% DLinDMA (cationic), 48% cholesterol and 2% PEG-conjugated DMG (2 kDa PEG). These proportions refer to the % moles in the total liposome.

DLinDMA (1,2-dilinoleyloxy-N,N-dimethyl-3-aminopropane) was synthesized using the procedure of reference 6. DSPC (1,2-Diastearoyl-sn-glycero-3-phosphocholine) was purchased from Genzyme. Cholesterol was obtained from Sigma-Aldrich. PEG-conjugated DMG (1,2-dimyristoyl-sn-glycero-3-phosphoethanolamine-N-[methoxy(polyethylene glycol), ammonium salt), DOTAP (1,2-dioleoyl-3-trimethylammonium-propane, chloride salt) and DC-chol (3(3-[N—(N',N'-dimethylaminoethane)-carbamoyl]cholesterol hydrochloride) were from Avanti Polar Lipids. 1,2-dimyristoyl-rac-glycero-3-methoxypolyethylene glycol was obtained from NOF Corporation (catalog #GM-020).

Briefly, lipids were dissolved in ethanol (2 ml), a RNA replicon was dissolved in buffer (2 ml, 100 mM sodium citrate, pH 6) and these were mixed with 2 ml of buffer followed by 1 hour of equilibration. The mixture was diluted with 6 ml buffer then filtered. The resulting product contained liposomes, with ~95% encapsulation efficiency.

For example, in one particular method, fresh lipid stock solutions were prepared in ethanol. 37 mg of DLinDMA, 11.8 mg of DSPC, 27.8 mg of cholesterol and 8.07 mg of PEG-DMG were weighed and dissolved in 7.55 mL of ethanol. The freshly prepared lipid stock solution was gently rocked at 37° C. for about 15 min to form a homogenous mixture. Then, 755 µL of the stock was added to 1.245 mL ethanol to make a working lipid stock solution of 2 mL. This amount of lipids was used to form liposomes with 250 µg RNA. A 2 mL working solution of RNA was also prepared from a stock solution of ~1 µg/µL in 100 mM citrate buffer (pH 6). Three 20 mL glass vials (with stir bars) were rinsed with RNase Away solution (Molecular BioProducts) and washed with plenty of MilliQ water before use to decontaminate the vials of RNases. One of the vials was used for the RNA working solution and the others for collecting the lipid and RNA mixes (as described later). The working lipid and RNA solutions were heated at 37° C. for 10 min before being loaded into 3 cc luer-lok syringes. 2 mL citrate buffer (pH 6) was loaded in another 3 cc syringe. Syringes containing RNA and the lipids were connected to a T mixer (PEEK™ 500 µm ID junction, Idex Health Science) using FEP tubing (fluorinated ethylene-propylene; all FEP tubing used has a 2 mm internal diameter and a 3 mm outer diameter). The outlet from the T mixer was also FEP tubing. The third syringe containing the citrate buffer was connected to a separate piece of FEP tubing. All syringes were then driven at a flow rate of 7 mL/min using a syringe pump. The tube outlets were positioned to collect the mixtures in a 20 mL glass vial (while stirring). The stir bar was taken out and the ethanol/aqueous solution was allowed to equilibrate to room temperature for 1 h. 4 ml of the mixture was loaded into a 5 cc syringe, which was connected to a piece of FEP tubing and in another 5 cc syringe connected to an equal length of FEP tubing, an equal amount of 100 mM citrate buffer (pH 6) was loaded. The two syringes were driven at 7 mL/min flow rate using the syringe pump and the final mixture collected in a 20 mL glass vial (while stirring). Next, the mixture collected from the second mixing step (liposomes) were passed through a Mustang Q membrane (an anion-exchange support that binds and removes anionic molecules, obtained from Pall Corporation). Before using this membrane for the liposomes, 4 mL of 1 M NaOH, 4 mL of 1 M NaCl and 10 mL of 100 mM citrate buffer (pH 6) were successively passed through it. Liposomes were warmed for 10 min at 37° C. before passing through the membrane. Next, liposomes were concentrated to 2 mL and dialyzed against 10-15 volumes of 1×PBS using by tangential flow filtration before recovering the final product. The TFF system and hollow fiber filtration membranes were purchased from Spectrum Labs (Rancho Dominguez) and were used according to the manufacturer's guidelines. Polysulfone hollow fiber filtration membranes with a 100 kD pore size cutoff and 8 cm$^2$ surface area were used. For in vitro and in vivo experiments formulations were diluted to the required RNA concentration with 1×PBS.

Figure 2:
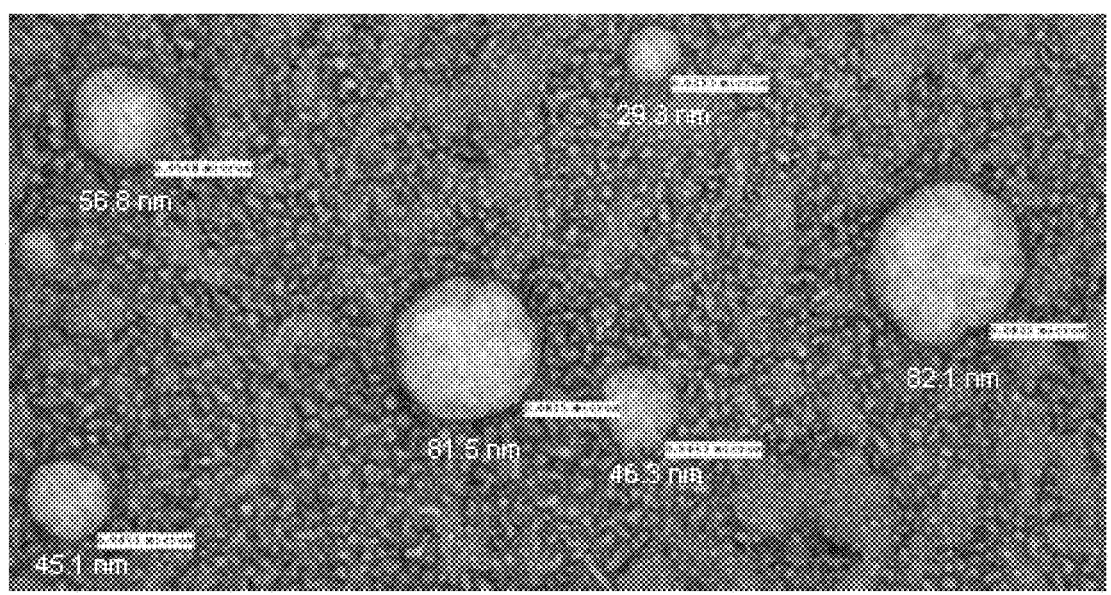
FIG. 2 is an electron micrograph of liposomes.
Figure 3:
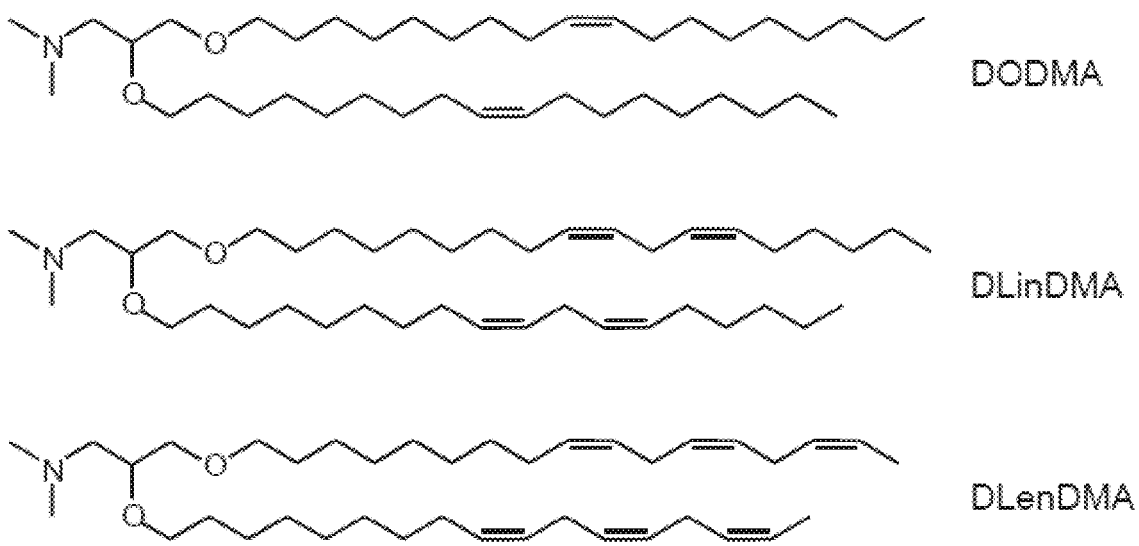
FIG. 3 shows the structures of DLinDMA, DLenDMA and DODMA.

FIG. 2 shows an example electron micrograph of liposomes prepared by these methods. These liposomes contain encapsulated RNA encoding full-length RSV F antigen. Dynamic light scattering of one batch showed an average diameter of 141 nm (by intensity) or 78 nm (by number).

The percentage of encapsulated RNA and RNA concentration were determined by Quant-iT RiboGreen RNA reagent kit (Invitrogen), following manufacturer's instructions. The ribosomal RNA standard provided in the kit was used to generate a standard curve. Liposomes were diluted 10× or 100× in 1×TE buffer (from kit) before addition of the dye. Separately, liposomes were diluted 10× or 100× in 1×TE buffer containing 0.5% Triton X before addition of the dye (to disrupt the liposomes and thus to assay total RNA). Thereafter an equal amount of dye was added to each solution and then ~180 µL of each solution after dye addition was loaded in duplicate into a 96 well tissue culture plate. The fluorescence (Ex 485 nm, Em 528 nm) was read on a microplate reader. All liposome formulations were dosed in vivo based on the encapsulated amount of RNA.

Figure 4:
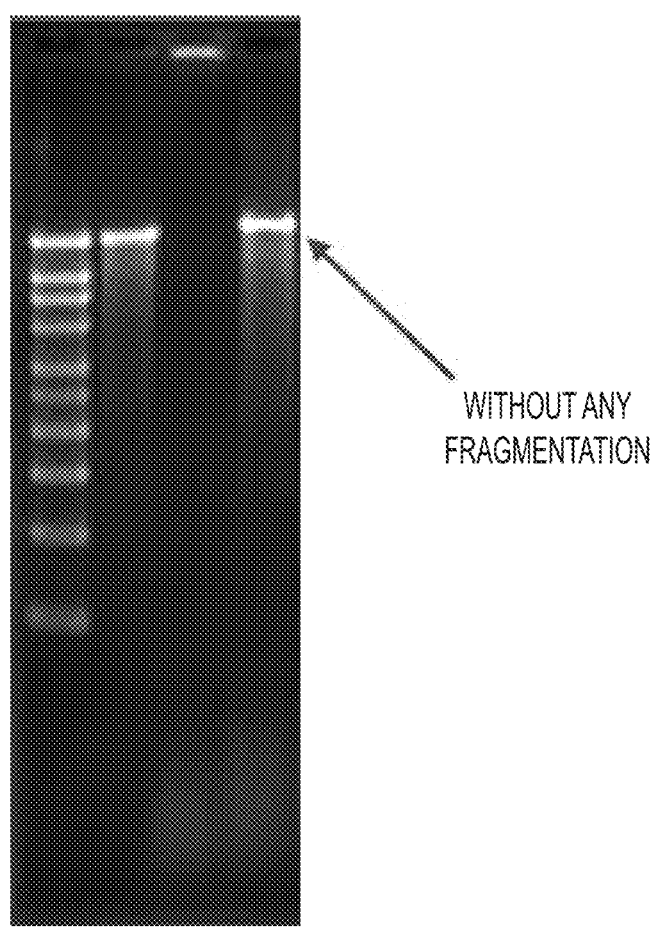
FIG. 4 shows a gel with stained RNA. Lanes show (1) markers (2) naked replicon (3) replicon encapsulated in liposome (4) liposome treated with RNase then subjected to phenol/chloroform extraction.

Encapsulation in liposomes was shown to protect RNA from RNase digestion. Experiments used 3.8 mAU of RNase A per microgram of RNA, incubated for 30 minutes at room temperature. RNase was inactivated with Proteinase K at 55° C. for 10 minutes. A 1:1 v/v mixture of sample to 25:24:1 v/v/v, phenol:chloroform:isoamyl alcohol was then added to extract the RNA from the lipids into the aqueous phase. Samples were mixed by vortexing for a few seconds and then placed on a centrifuge for 15 minutes at 12k RPM. The aqueous phase (containing the RNA) was removed and used to analyze the RNA. Prior to loading (400 ng RNA per well) all the samples were incubated with formaldehyde loading dye, denatured for 10 minutes at 65° C. and cooled to room temperature. Ambion Millennium markers were used to approximate the molecular weight of the RNA construct. The gel was run at 90 V. The gel was stained using 0.1% SYBR gold according to the manufacturer's guidelines in water by rocking at room temperature for 1 hour. FIG. 1 shows that RNase completely digests RNA in the absence of encapsulation (lane 3). RNA is undetectable after encapsulation (lane 4), and no change is seen if these liposomes are treated with RNase (lane 4). After RNase-treated liposomes are subjected to phenol extraction, undigested RNA is seen (lane 6). Even after 1 week at 4° C. the RNA could be seen without any fragmentation (FIG. 4, arrow). Protein expression in vivo was unchanged after 6 weeks at 4° C. and one freeze-thaw cycle. Thus liposome-encapsulated RNA is stable.

To assess in vivo expression of the RNA a reporter enzyme (SEAP; secreted alkaline phosphatase) was encoded in the replicon, rather than an immunogen. Expression levels were measured in sera diluted 1:4 in 1× Phospha-Light dilution buffer using a chemiluminescent alkaline phosphate substrate. 8-10 week old BALB/c mice (5/group) were injected intramuscularly on day 0, 50 µl per leg with 0.1 µg or 1 µg RNA dose. The same vector was also administered without the liposomes (in RNase free 1×PBS) at 1 µg. Virion-packaged replicons were also tested. Virion-packaged replicons used herein (referred to as "VRPs") were obtained by the methods of reference 43, where the alphavirus replicon is derived from the mutant VEEV or a chimera derived from the genome of VEEV engineered to contain the 3' UTR of Sindbis virus and a Sindbis virus packaging signal (PS), packaged by co-electroporating them into BHK cells with defective helper RNAs encoding the Sindbis virus capsid and glycoprotein genes.

Figure 5:
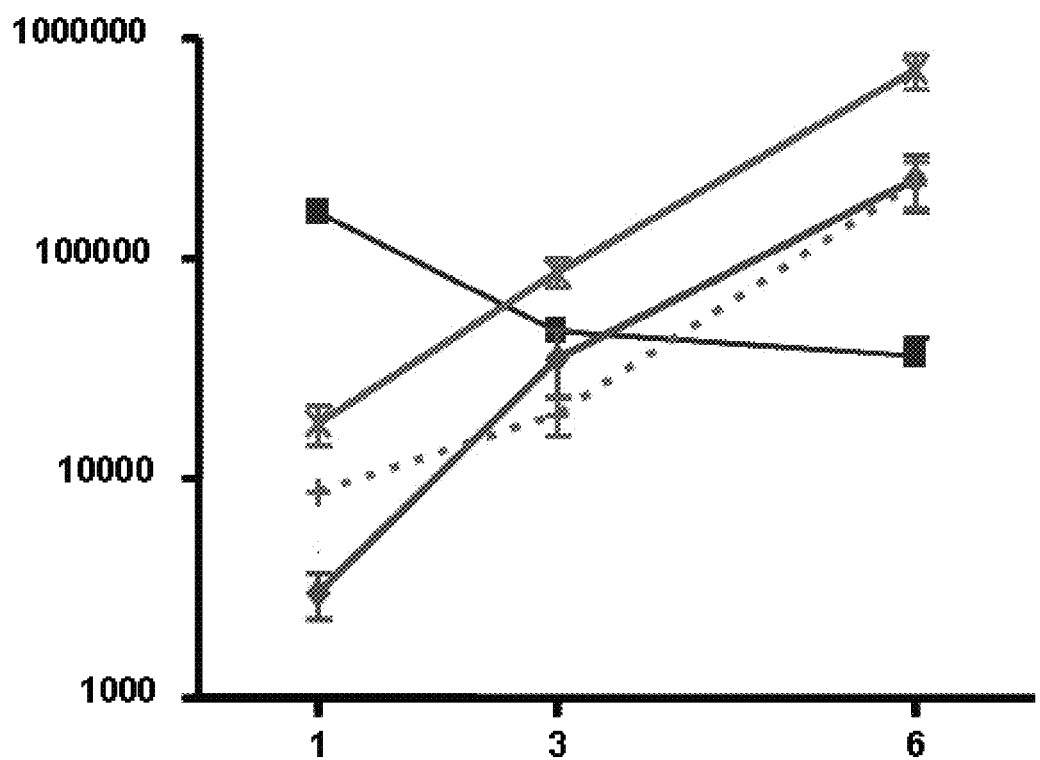
FIG. 5 shows protein expression at days 1, 3 and 6 after delivery of RNA as a virion-packaged replicon (squares), as naked RNA (diamonds), or in liposomes (+=0.1 μg, x=1 μg).
Figure 6:
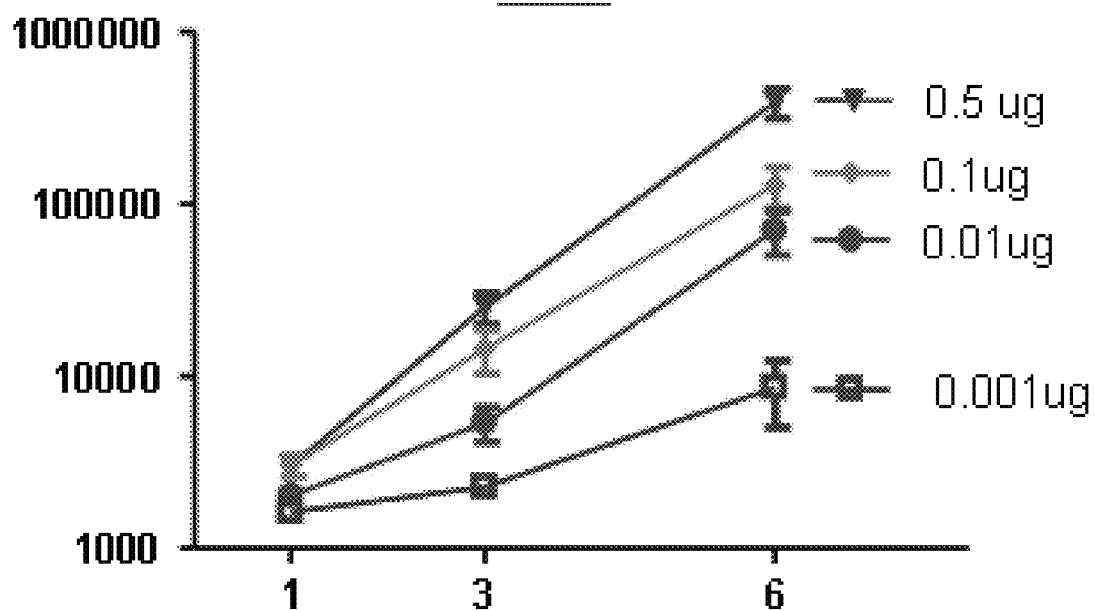
FIG. 6 shows protein expression at days 1, 3 and 6 after delivery of four different doses of liposome-encapsulated RNA.
Figure 9:
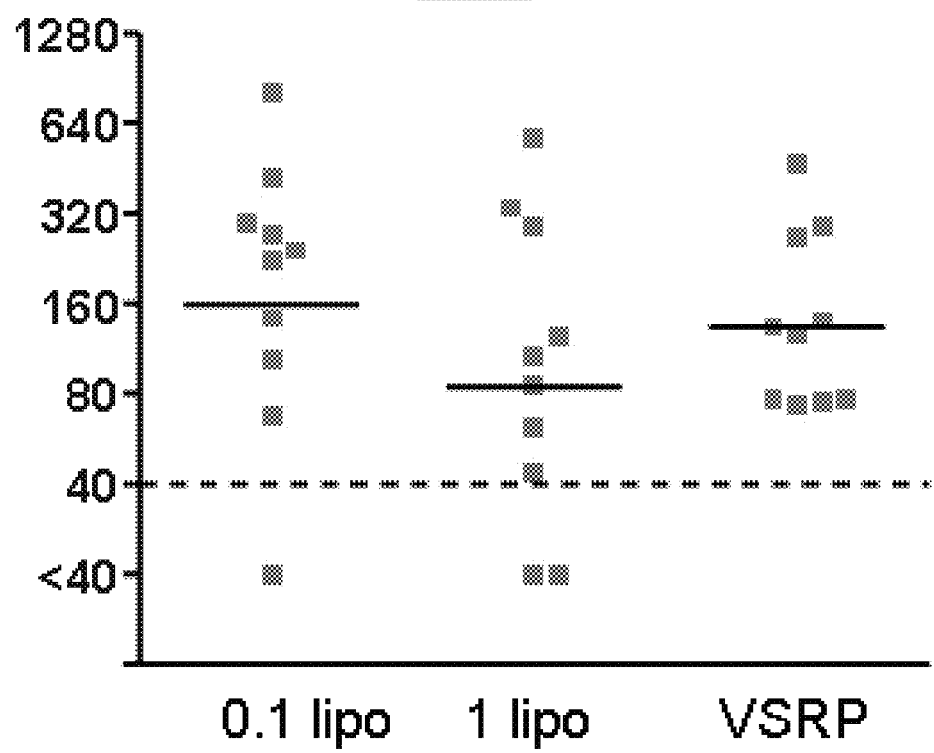
FIG. 9 shows neutralising antibody titers in animals receiving VRP or either 0.1 µg or 1 µg liposome-encapsulated RNA.

As shown in FIG. 5, encapsulation increased SEAP levels by about ½ log at the 1 µg dose, and at day 6 expression from a 0.1 µg encapsulated dose matched levels seen with 1 µg unencapsulated dose. By day 3 expression levels exceeded those achieved with VRPs (squares). Thus expressed increased when the RNA was formulated in the liposomes relative to the naked RNA control, even at a 10× lower dose. Expression was also higher relative to the VRP control, but the kinetics of expression were very different (see FIG. 5). Delivery of the RNA with electroporation resulted in increased expression relative to the naked RNA control, but these levels were lower than with liposomes.

Figure 10:
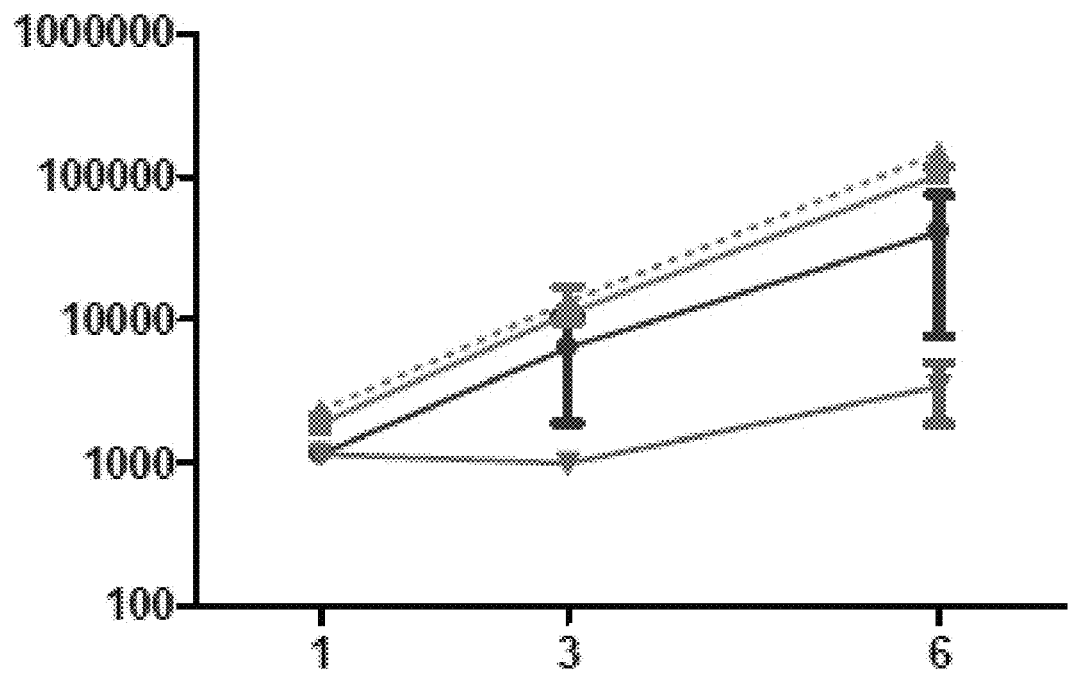
FIG. 10 shows expression levels after delivery of a replicon as naked RNA (circles), liposome-encapsulated RNA (triangle & square), or as a lipoplex (inverted triangle).
Figure 11:
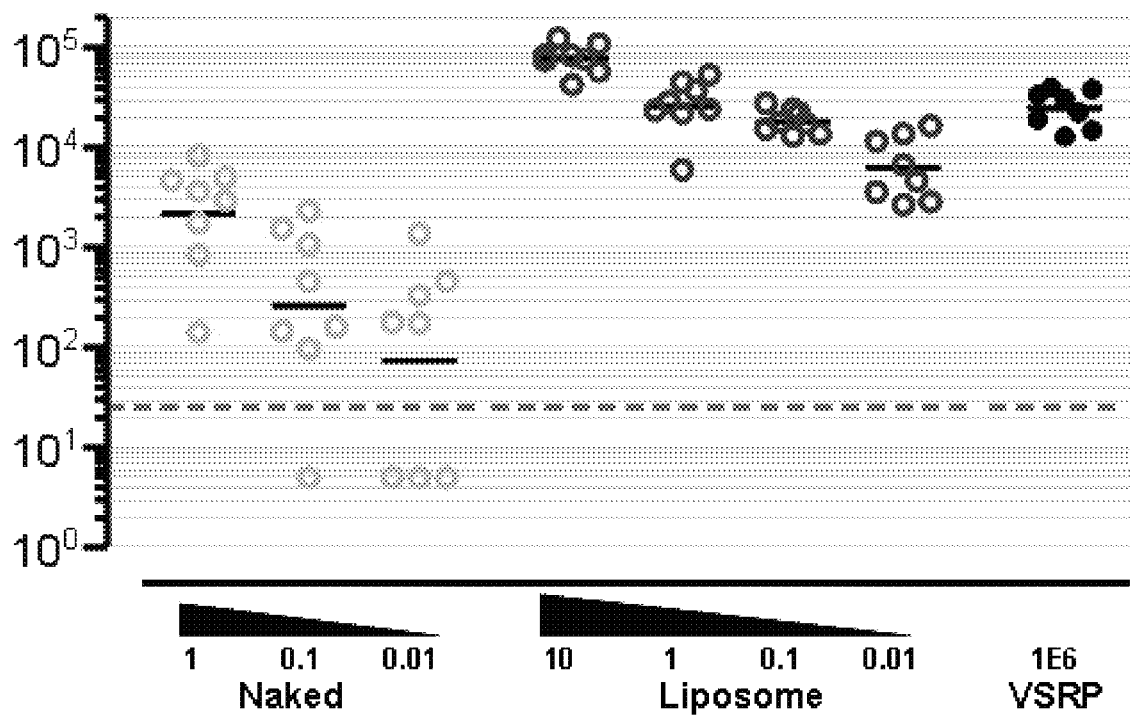
FIG. 11 shows F-specific IgG titers (2 weeks after second dose) after delivery of a replicon as naked RNA (0.01-1 µg), liposome-encapsulated RNA (0.01-10 µg), or packaged as a virion (VRP, $10^6$ infectious units or IU).
Figure 12:
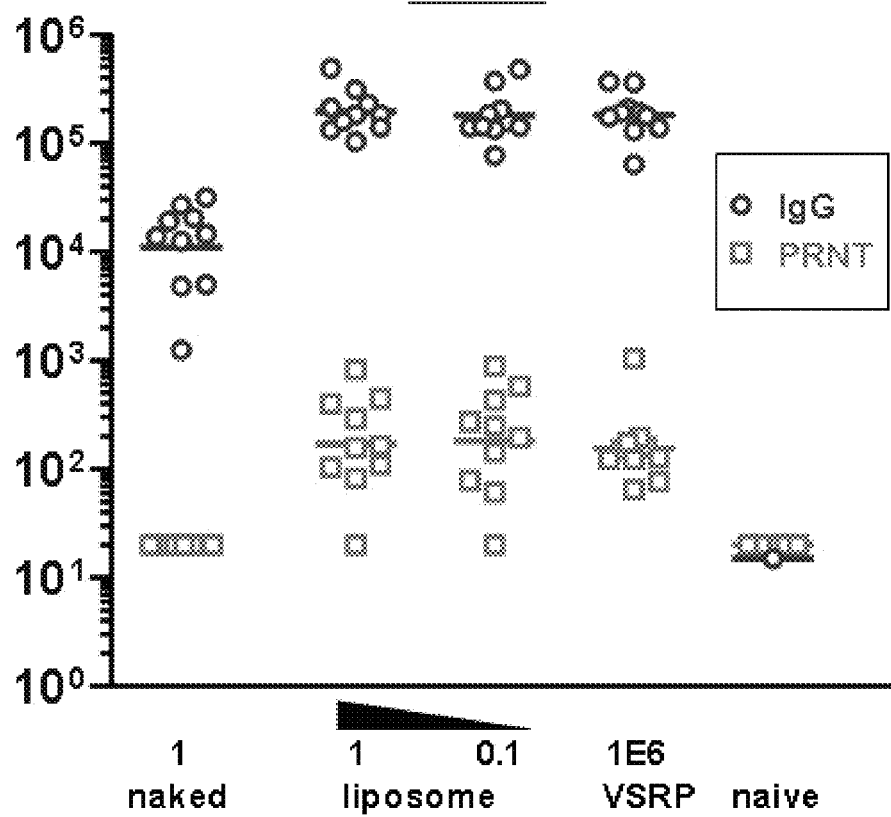
FIG. 12 shows F-specific IgG titers (circles) and PRNT titers (squares) after delivery of a replicon as naked RNA (1 µg), liposome-encapsulated RNA (0.1 or 1 µg), or packaged as a virion (VRP, $10^6$ IU). Titers in naïve mice are also shown. Solid lines show geometric means.
Figure 14B:
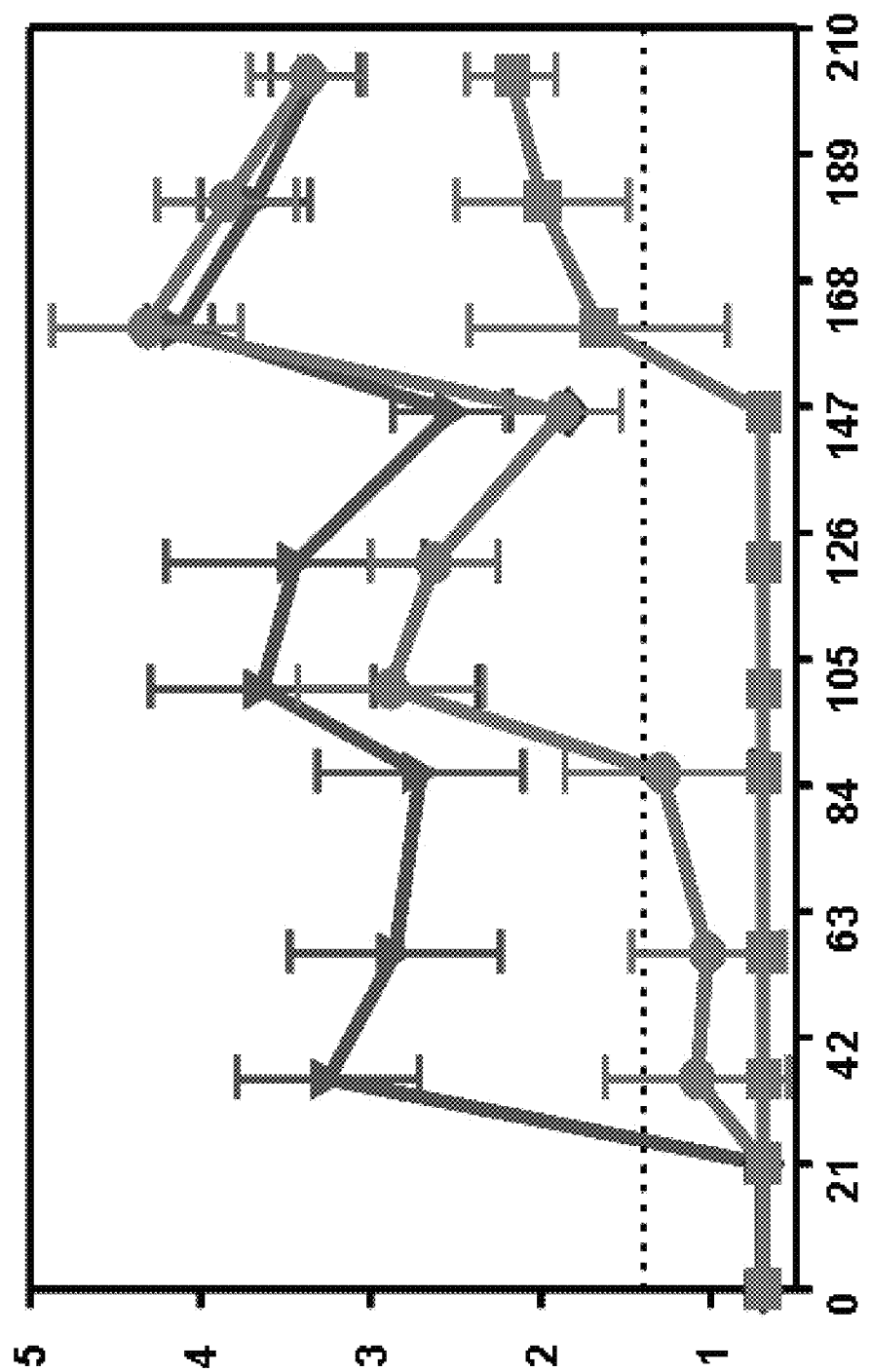

To assess whether the effect seen in the liposome groups was due merely to the liposome components, or was linked to the encapsulation, the replicon was administered in encapsulated form (with two different purification protocols, 0.1 µg RNA), or mixed with the liposomes after their formation (a non-encapsulated "lipoplex", 0.1 µg RNA), or as naked RNA (1 µg). FIG. 10 shows that the lipoplex gave the lowest levels of expression, showing that shows encapsulation is essential for potent expression.

In vivo studies using liposomal delivery confirmed these findings. Mice received various combinations of (i) self-replicating RNA replicon encoding full-length RSV F protein (ii) self-replicating GFP-encoding RNA replicon (iii) GFP-encoding RNA replicon with a knockout in nsP4 which eliminates self-replication (iv) full-length RSV F-protein. 13 groups in total received:

| | | |
|---|---|---|
| A | — | — |
| B | 0.1 µg of (i), naked | — |
| C | 0.1 µg of (i), encapsulated in liposome | — |
| D | 0.1 µg of (i), with separate liposomes | — |
| E | 0.1 µg of (i), naked | 10 µg of (ii), naked |
| F | 0.1 µg of (i), naked | 10 µg of (iii), naked |
| G | 0.1 µg of (i), encapsulated in liposome | 10 µg of (ii), naked |
| H | 0.1 µg of (i), encapsulated in liposome | 10 µg of (iii), naked |
| I | 0.1 µg of (i), encapsulated in liposome | 1 µg of (ii), encapsulated in liposome |
| J | 0.1 µg of (i), encapsulated in liposome | 1 µg of (iii), encapsulated in liposome |
| K | 5 µg F protein | — |
| L | 5 µg F protein | 1 µg of (ii), encapsulated in liposome |
| M | 5 µg F protein | 1 µg of (iii), encapsulated in liposome |

Figure 18:
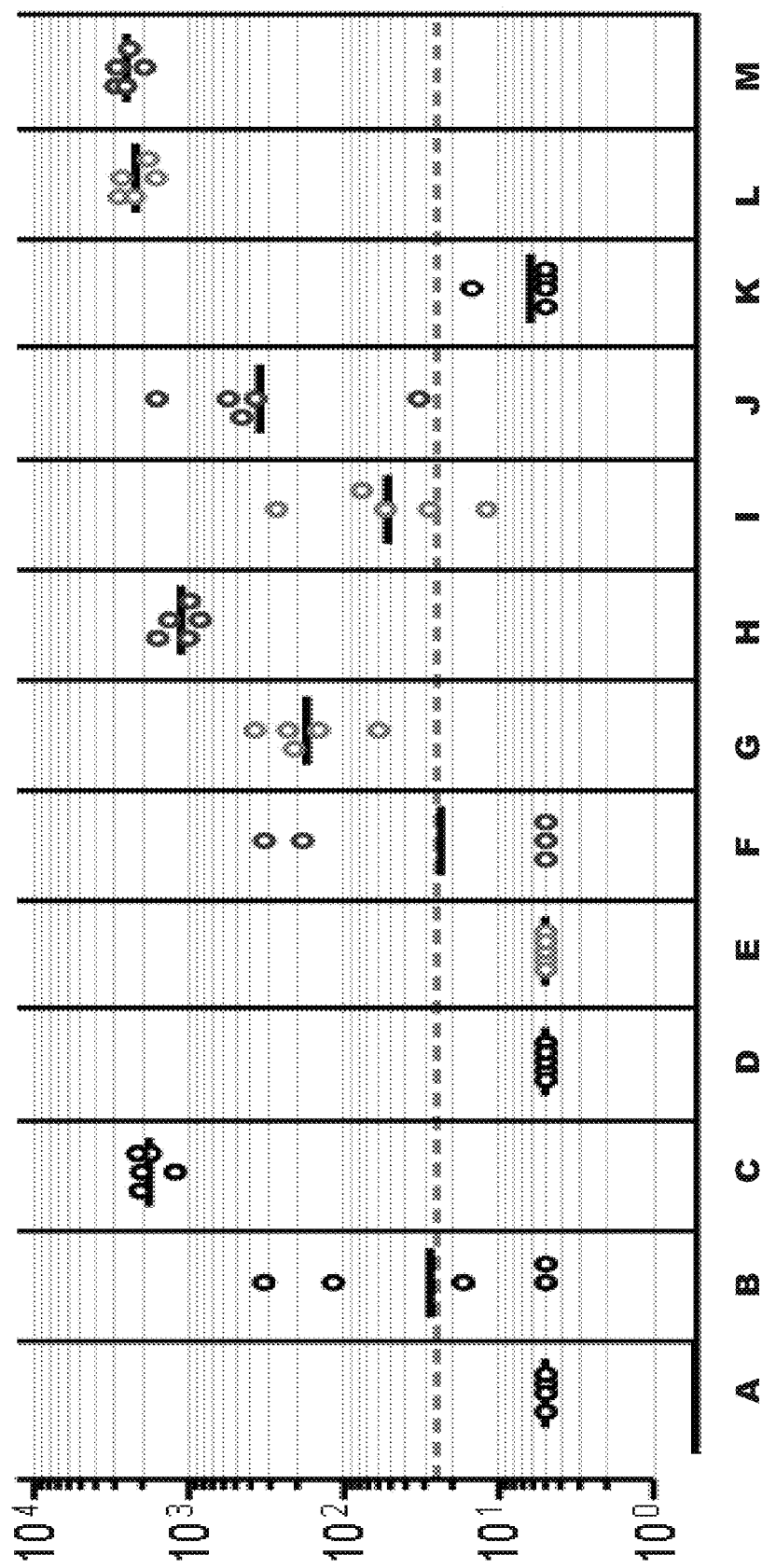
FIG. 18 shows IgG titers in 13 groups of mice. Each circle is an individual mouse, and solid lines show geometric means. The dotted horizontal line is the assay's detection limit. The 13 groups are, from left to right, A to M as described below.

Results in FIG. 18 show that F-specific IgG responses required encapsulation in the liposome rather than mere co-delivery (compare groups C & D). A comparison of groups K, L and M shows that the RNA provided an adjuvant effect against co-delivered protein, and this effect was seen with both replicating and non-replicating RNA.

Further SEAP experiments showed a clear dose response in vivo, with expression seen after delivery of as little as 1 ng RNA (FIG. 6). Further experiments comparing expression from encapsulated and naked replicons indicated that 0.01 μg encapsulated RNA was equivalent to 1 μg of naked RNA. At a 0.5 μg dose of RNA the encapsulated material gave a 12-fold higher expression at day 6; at a 0.1 μg dose levels were 24-fold higher at day 6.

Rather than looking at average levels in the group, individual animals were also studied. Whereas several animals were non-responders to naked replicons, encapsulation eliminated non-responders.

Further experiments replaced DLinDMA with DOTAP. Although the DOTAP liposomes gave better expression than naked replicon, they were inferior to the DLinDMA liposomes (2- to 3-fold difference at day 1). Whereas DOTAP has a quaternary amine, and so have a positive charge at the point of delivery, DLinDMA has a tertiary amine.

To assess in vivo immunogenicity a replicon was constructed to express full-length F protein from respiratory syncytial virus (RSV). This was delivered naked (1 μg), encapsulated in liposomes (0.1 or 1 μg), or packaged in virions ($10^6$ IU; "VRP") at days 0 and 21. FIG. 7 shows anti-F IgG titers 2 weeks after the second dose, and the liposomes clearly enhance immunogenicity. FIG. 8 shows titers 2 weeks later, by which point there was no statistical difference between the encapsulated RNA at 0.1 μg, the encapsulated RNA at 1 μg, or the VRP group. Neutralisation titers (measured as 60% plaque reduction, "PRNT60") were not significantly different in these three groups 2 weeks after the second dose (FIG. 9). FIG. 12 shows both IgG and PRNT titers 4 weeks after the second dose.

FIG. 13 confirms that the RNA elicits a robust CD8 T cell response.

Further experiments compared F-specific IgG titers in mice receiving VRP, 0.1 μg liposome-encapsulated RNA, or 1 μg liposome-encapsulated RNA. Titer ratios (VRP:liposome) at various times after the second dose were as follows:

| | 2 weeks | 4 weeks | 8 weeks |
|---|---|---|---|
| 0.1 μg | 2.9 | 1.0 | 1.1 |
| 1 μg | 2.3 | 0.9 | 0.9 |

Thus the liposome-encapsulated RNA induces essentially the same magnitude of immune response as seen with virion delivery.

Further experiments showed superior F-specific IgG responses with a 10 μg dose, equivalent responses for 1 μg and 0.1 μg doses, and a lower response with a 0.01 μg dose. FIG. 11 shows IgG titers in mice receiving the replicon in naked form at 3 different doses, in liposomes at 4 different doses, or as VRP ($10^6$ IU). The response seen with 1 μg liposome-encapsulated RNA was statistically insignificant (ANOVA) when compared to VRP, but the higher response seen with 10 μg liposome-encapsulated RNA was statistically significant ($p<0.05$) when compared to both of these groups.

A further study confirmed that the 0.1 μg of liposome-encapsulated RNA gave much higher anti-F IgG responses (15 days post-second dose) than 0.1 μg of delivered DNA, and even was more immunogenic than 20 μg plasmid DNA encoding the F antigen, delivered by electroporation (Elgen™ DNA Delivery System, Inovio).

A further study was performed in cotton rats (*Sigmodon hispidis*) instead of mice. At a 1 μg dose liposome encapsulation increased F-specific IgG titers by 8.3-fold compared to naked RNA and increased PRNT titers by 9.5-fold. The magnitude of the antibody response was equivalent to that induced by $5\times10^6$ IU VRP. Both naked and liposome-encapsulated RNA were able to protect the cotton rats from RSV challenge ($1\times10^5$ plaque forming units), reducing lung viral load by at least 3.5 logs. Encapsulation increased the reduction by about 2-fold.

A large-animal study was performed in cattle. Cows were immunised with 66 μg of replicon encoding full-length RSV F protein at days 0 and 21, formulated inside liposomes. PBS alone was used as a negative control, and a licensed vaccine was used as a positive control ("Triangle 4" from Fort Dodge, containing killed virus). FIG. 14 show F-specific IgG titers over 63 day and 210 day periods, respectively, starting from the first immunisation. The RNA replicon was immunogenic in the cows, although it gave lower titers than the licensed vaccine. All vaccinated cows showed F-specific antibodies after the second dose, and titers were very stable from the period of 2 to 6 weeks after the second dose (and were particularly stable for the RNA vaccine).

Mechanism of Action

Figure 19A:
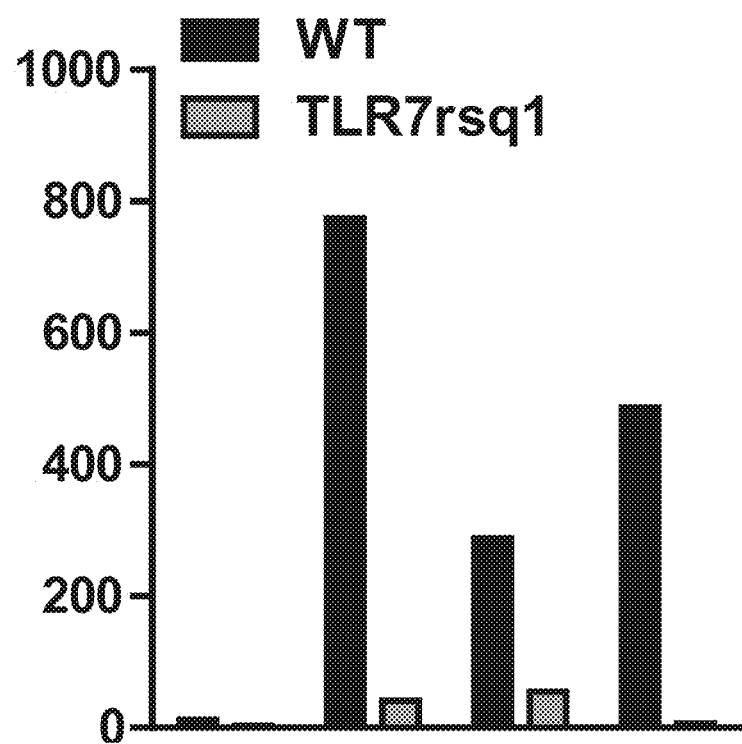
FIGS. 19A and 19B show IL-6 (FIG. 19A) and IFNα (FIG. 19B) (pg/ml) released by pDC. There are 4 pairs of bars, from left to right: control; immunised with RNA+ DOTAP; immunised with RNA+lipofectamine; and immunised with RNA in liposomes. In each pair the black bar is wild-type mice, grey is rsq1 mutant.
Figure 19B:
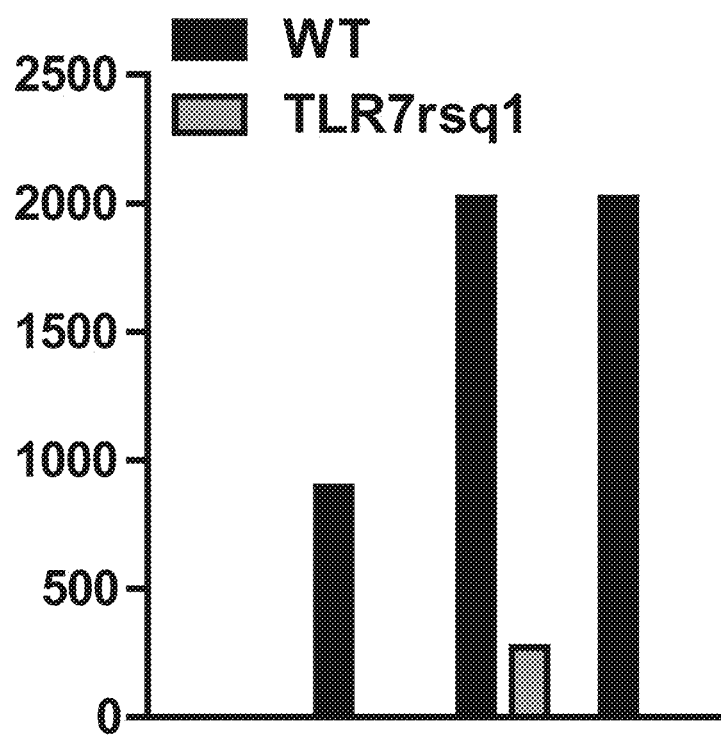

Bone marrow derived dendritic cells (pDC) were obtained from wild-type mice or the "Resq" (rsq1) mutant strain. The mutant strain has a point mutation at the amino terminus of its TLR7 receptor which abolishes TLR7 signalling without affecting ligand binding as disclosed in reference 44. The cells were stimulated with replicon RNA formulated with DOTAP, lipofectamine 2000 or inside a liposome. As shown in FIGS. 19A and 19B, IL-6 and INFα, respectively, were induced in WT cells but this response was almost completely abrogated in mutant mice. These results shows that TLR7 is required for RNA recognition in immune cells, and that liposome-encapsulated replicons can cause immune cells to secrete high levels of both interferons and pro-inflammatory cytokines.

pKa Measurement

The pKa of a lipid is measured in water at standard temperature and pressure using the following technique:

2 mM solution of lipid in ethanol is prepared by weighing the lipid and dissolving in ethanol. 0.3 mM solution of fluorescent probe 6 (p toluidino)-2-naphthalenesulfonic acid (TNS) in ethanol:methanol 9:1 is prepared by first making 3 mM solution of TNS in methanol and then diluting to 0.3 mM with ethanol.

An aqueous buffer containing sodium phosphate, sodium citrate sodium acetate and sodium chloride, at the concentrations 20 mM, 25 mM, 20 mM and 150 mM, respectively, is prepared. The buffer is split into eight parts and the pH adjusted either with 12N HCl or 6N NaOH to 4.44-4.52, 5.27, 6.15-6.21, 6.57, 7.10-7.20, 7.72-7.80, 8.27-8.33 and 10.47-11.12. 400 µL of 2 mM lipid solution and 800 µL of 0.3 mM TNS solution are mixed.

7.5 µL of probe/lipid mix are added to 242.5 µL of buffer in a 1 mL 96 well plate. This is done with all eight buffers. After mixing, 100 µL of each probe/lipid/buffer mixture is transferred to a 250 µL black with clear bottom 96 well plate (e.g. model COSTAR 3904, Corning). A convenient way of performing this mixing is to use the Tecan Genesis RSP150 high throughput liquid handler and Gemini Software.

Fluorescence of each probe/lipid/buffer mixture is measured (e.g. with a SpectraMax M5 spectrophotometer and SoftMax pro 5.2 software) with 322 nm excitation, 431 nm emission (auto cutoff at 420 nm).

After the measurement, the background fluorescence value of an empty well on the 96 well plate is subtracted from each probe/lipid/buffer mixture. The fluorescence intensity values are then normalized to the value at lowest pH. The normalized fluorescence intensity is then plotted against pH and a line of best fit is provided.

The point on the line of best fit at which the normalized fluorescence intensity is equal to 0.5 is found. The pH corresponding to normalized fluorescence intensity equal to 0.5 is found and is considered the pKa of the lipid.

This method gives a pKa of 5.8 for DLinDMA. The pKa values measured by this method for cationic lipids of reference 5 are included below.

Encapsulation in Liposomes Using Alternative Cationic Lipids

As an alternative to using DlinDMA, the cationic lipids of reference 5 are used. These lipids can be synthesised as disclosed in reference 5.

The liposomes formed above using DlinDMA are referred to hereafter as the "RV01" series. The DlinDMA was replaced with various cationic lipids in series "RV02" to "RV12" as described below. Two different types of each liposome were formed, using 2% PEG2000-DMG with either (01) 40% of the cationic lipid, 10% DSPC, and 48% cholesterol, or (02) 60% of the cationic lipid and 38% cholesterol. Thus a comparison of the (01) and (02) liposomes shows the effect of the neutral zwitterionic lipid.

RV02 liposomes were made using the following cationic lipid (pKa >9, without a tertiary amine):

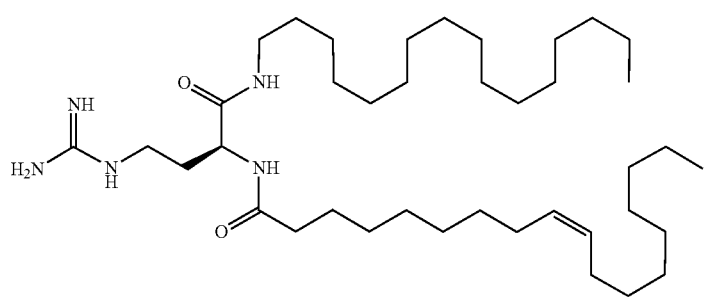

RV03 liposomes were made using the following cationic lipid (pKa 6.4):

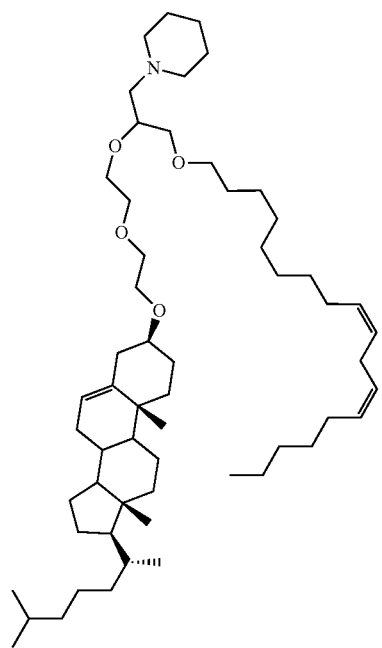
RV04 liposomes were made using the following cationic lipid (pKa 6.62):
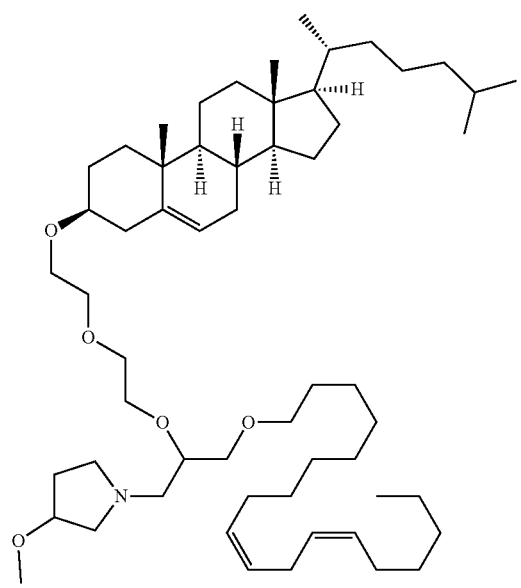
RV05 liposomes were made using the following cationic lipid (pKa 5.85):

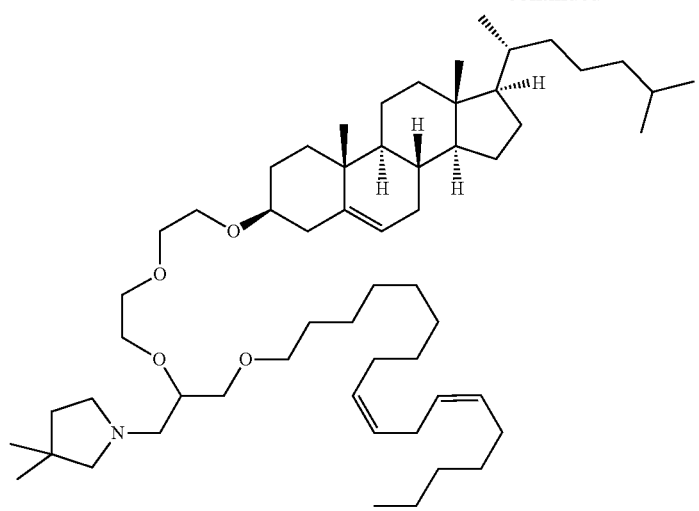
RV06 liposomes were made using the following cationic lipid (pKa 7.27):
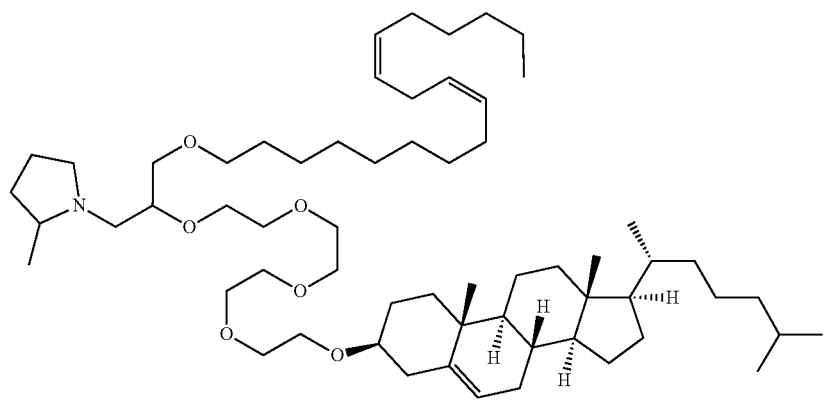
RV07 liposomes were made using the following cationic lipid (pKa 6.8):
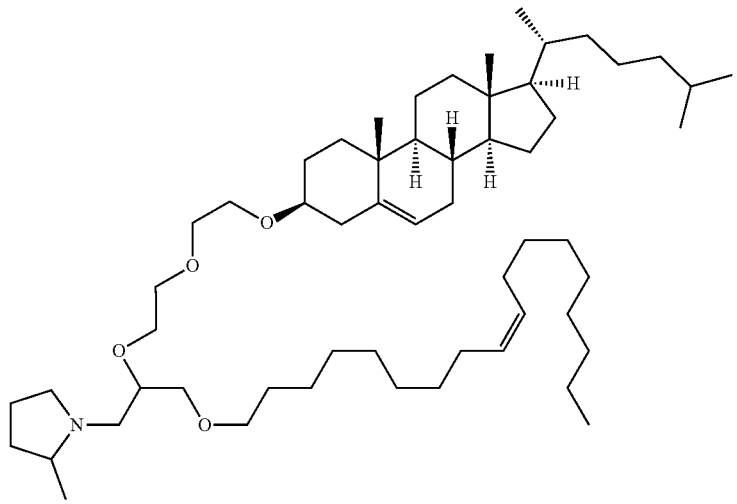
RV08 liposomes were made using the following cationic lipid (pKa 5.72):

-continued
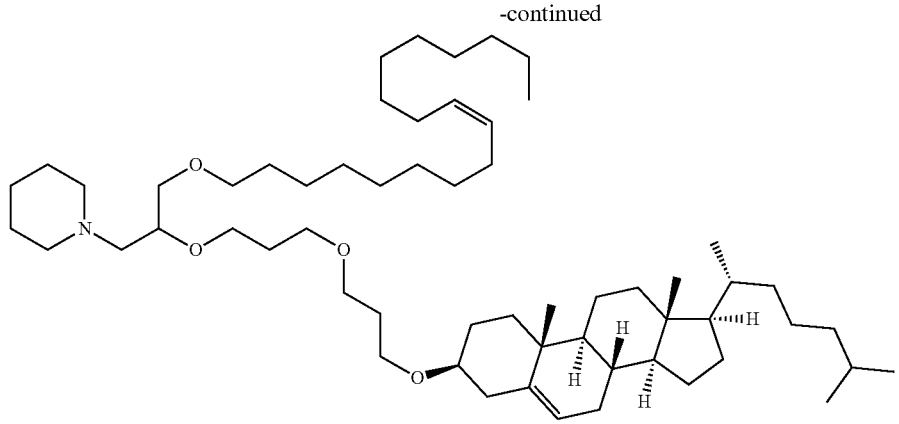
RV09 liposomes were made using the following cationic lipid (pKa 6.07):
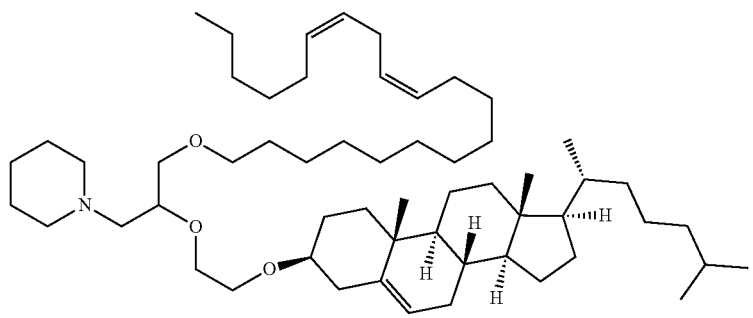
RV10 liposomes were made for comparison using the following cationic lipid (pKa 7.86):
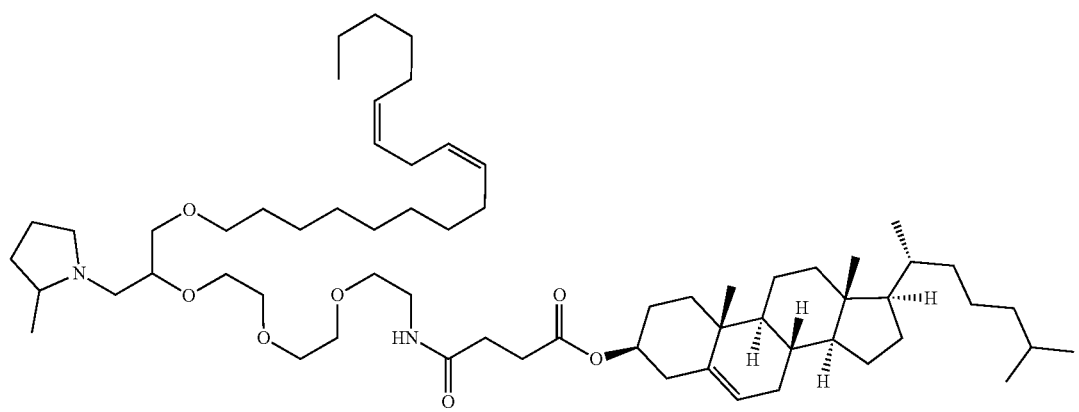
RV11 liposomes were made using the following cationic lipid (pKa 6.41):
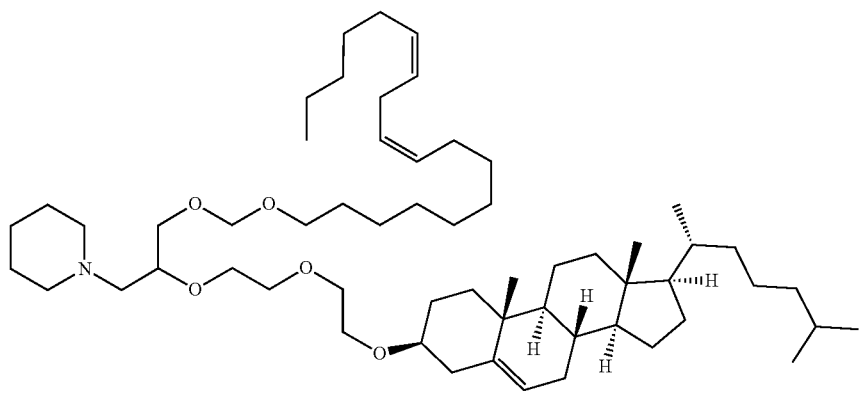
RV12 liposomes were made using the following cationic lipid (pKa 7):

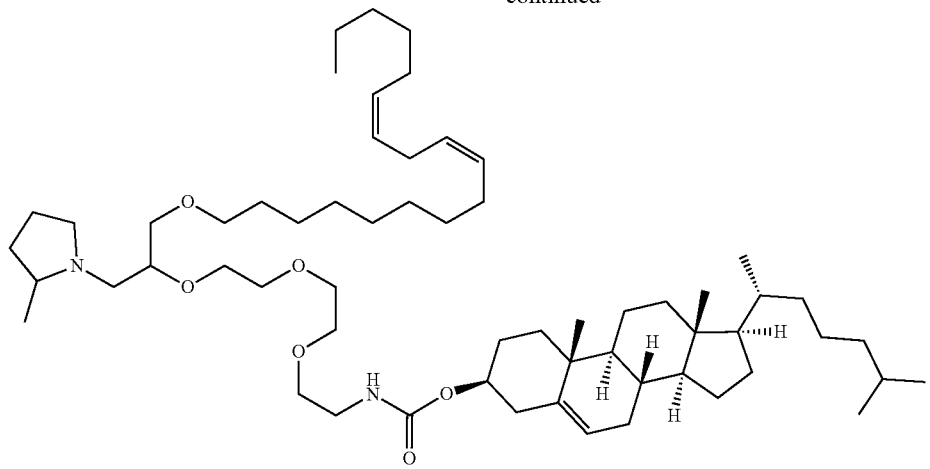

RV16 liposomes were made using the following cationic lipid (pKa 6.1) as disclosed in reference 45:

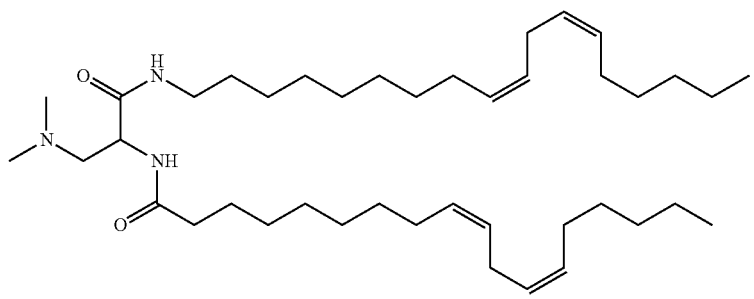

RV17 liposomes were made using the following cationic lipid (pKa 6.1) as disclosed in reference 45:

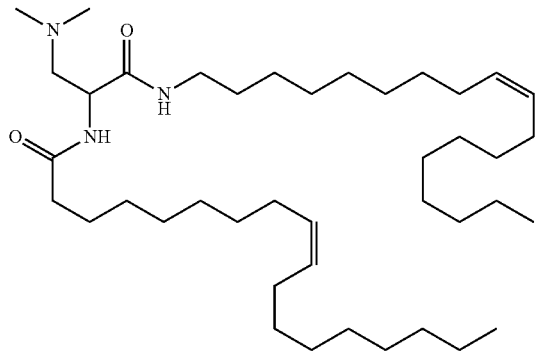

RV18 liposomes were made using DODMA. RV19 liposomes were made using DOTMA, and RV13 liposomes were made with DOTAP, both having a quaternary amine headgroup.

These liposomes were characterised and were tested with the SEAP reporter described above. The following table shows the size of the liposomes (Z average and polydispersity index), the % of RNA encapsulation in each liposome, together with the SEAP activity detected at days 1 and 6 after injection. SEAP activity is relative to "RV01(02)" liposomes made from DlinDMA, cholesterol and PEG-DMG:

| RV | Lipid pKa | Zav (pdI) | % encapsulation | SEAP day 1 | SEAP day 6 |
|---|---|---|---|---|---|
| RV01 (01) | 5.8 | 154.6 (0.131) | 95.5 | 80.9 | 71.1 |
| RV01 (02) | 5.8 | 162.0 (0.134) | 85.3 | 100 | 100 |
| RV02 (01) | >9 | 133.9 (0.185) | 96.5 | 57 | 45.7 |
| RV02 (02) | >9 | 134.6 (0.082) | 97.6 | 54.2 | 4.3 |
| RV03 (01) | 6.4 | 158.3 (0.212) | 62.0 | 65.7 | 44.9 |
| RV03 (02) | 6.4 | 164.2 (0.145) | 86 | 62.2 | 39.7 |
| RV04 (01) | 6.62 | 131.0 (0.145) | 74.0 | 91 | 154.8 |
| RV04 (02) | 6.62 | 134.6 (0.117) | 81.5 | 90.4 | 142.6 |
| RV05 (01) | 5.85 | 164.0 (0.162) | 76.0 | 76.9 | 329.8 |
| RV05 (02) | 5.85 | 177.8 (0.117) | 72.8 | 67.1 | 227.9 |
| RV06 (01) | 7.27 | 116.0 (0.180) | 79.8 | 25.5 | 12.4 |
| RV06 (02) | 7.27 | 136.3 (0.164) | 74.9 | 24.8 | 23.1 |
| RV07 (01) | 6.8 | 140.6 (0.184) | 77 | 26.5 | 163.3 |
| RV07 (02) | 6.8 | 138.6 (0.122) | 87 | 29.7 | 74.8 |
| RV 08 (01) | 5.72 | 176.7 (0.185) | 50 | 76.5 | 187 |
| RV08 (02) | 5.72 | 199.5 (0.191) | 46.3 | 82.4 | 329.8 |
| RV09 (01) | 6.07 | 165.3 (0.169) | 72.2 | 65.1 | 453.9 |
| RV09 (02) | 6.07 | 179.5 (0.157) | 65 | 68.5 | 658.2 |
| RV10 (01) | 7.86 | 129.7 (0.184) | 78.4 | 113.4 | 47.8 |

-continued

| RV | Lipid pKa | Zav (pdI) | % encapsulation | SEAP day 1 | SEAP day 6 |
|---|---|---|---|---|---|
| RV10 (02) | 7.86 | 147.6 (0.131) | 80.9 | 78.2 | 10.4 |
| RV11 (01) | 6.41 | 129.2 (0.186) | 71 | 113.6 | 242.2 |
| RV11 (02) | 6.41 | 139 (0198) | 75.2 | 71.8 | 187.2 |
| RV12 (01) | 7 | 135.7 (0.161) | 78.8 | 65 | 10 |
| RV12 (02) | 7 | 158.3 (0.287) | 69.4 | 78.8 | 8.2 |

Figure 15:
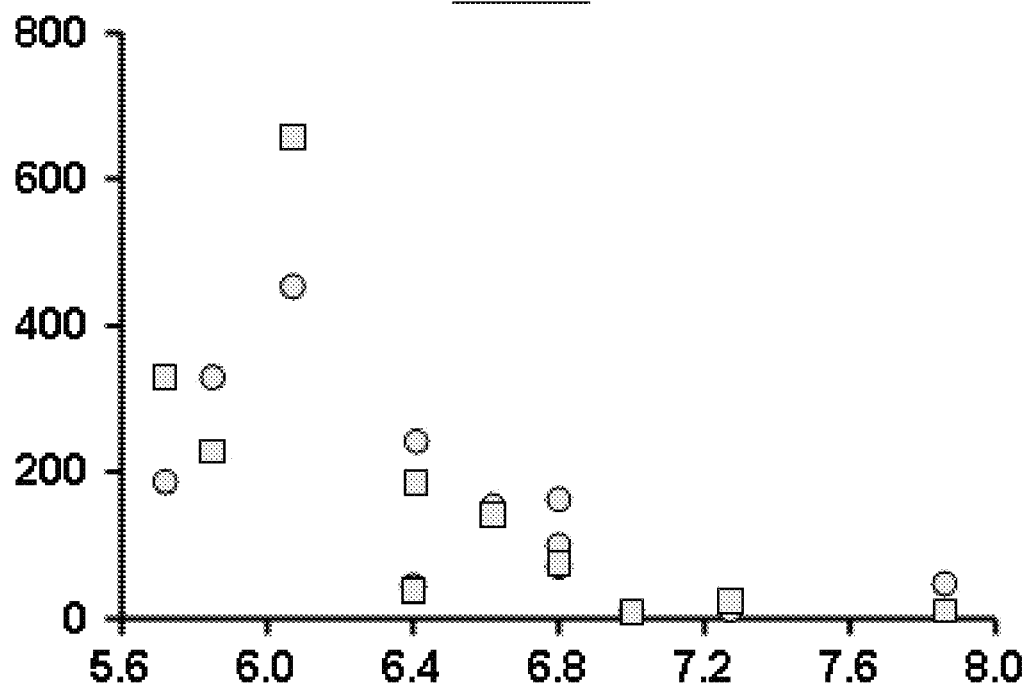
FIG. 15 shows SEAP expression (relative intensity) at day 6 against pKa of lipids used in the liposomes. Circles show levels for liposomes with DSPC, and squares for liposomes without DSPC; sometimes a square and circle overlap, leaving only the square visible for a given pKa.

FIG. 15 plots the SEAP levels at day 6 against the pKa of the cationic lipids. The best results are seen where the lipid has a pKa between 5.6 and 6.8, and ideally between 5.6 and 6.3.

Figure 16:
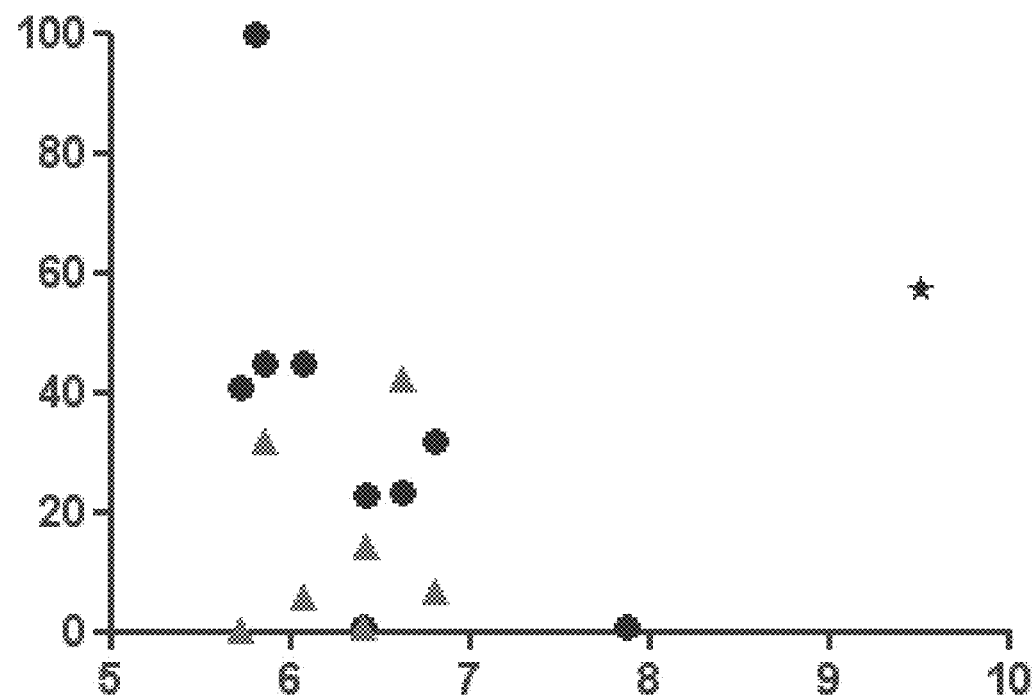
FIG. 16 shows anti-F titers expression (relative to RV01, 100%) two weeks after a first dose of replicon encoding F protein. The titers are plotted against pKa in the same way as in FIG. 15. The star shows RV02, which used a cationic lipid having a higher pKa than the other lipids. Triangles show data for liposomes lacking DSPC; circles are for liposomes which included DSPC.

These liposomes were also used to deliver a replicon encoding full-length RSV F protein. Total IgG titers against F protein two weeks after the first dose (2wp1) are plotted against pKa in FIG. 16. The best results are seen where the pKa is where the cationic lipid has a pKa between 5.7-5.9, but pKa alone is not enough to guarantee a high titer e.g. the lipid must still support liposome formation.

RSV Immunogenicity

Further work was carried out with a self-replicating replicon (vA317) encoding RSV F protein. BALB/c mice, 4 or 8 animals per group, were given bilateral intramuscular vaccinations (50 µL per leg) on days 0 and 21 with the replicon (1 µg) alone or formulated as liposomes with the RV01 or RV05 lipids (see above; pKa of 5.8 or 5.85) or with RV13. The RV01 liposomes had 40% DlinDMA, 10% DSPC, 48% cholesterol and 2% PEG-DMG, but with differing amounts of RNA. The RV05(01) liposomes had 40% cationic lipid, 48% cholesterol, 10% DSPC, and 2% PEG-DMG; the RV05(02) liposomes had 60% cationic lipid, 38% cholesterol, and 2% PEG-DMG. The RV13 liposomes had 40% DOTAP, 10% DPE, 48% cholesterol and 2% PEG-DMG. For comparison, naked plasmid DNA (20 µg) expressing the same RSV-F antigen was delivered either using electroporation or with RV01(10) liposomes (0.1 µg DNA). Four mice were used as a naïve control group.

Liposomes were prepared by method (A) or method (B). In method (A) fresh lipid stock solutions in ethanol were prepared. 37 mg of cationic lipid, 11.8 mg of DSPC, 27.8 mg of cholesterol and 8.07 mg of PEG-DMG were weighed and dissolved in 7.55 mL of ethanol. The freshly prepared lipid stock solution was gently rocked at 37° C. for about 15 min to form a homogenous mixture. Then, 226.7 µL of the stock was added to 1.773 mL ethanol to make a working lipid stock solution of 2 mL. This amount of lipids was used to form liposomes with 75 µg RNA to give an 8:1 nitrogen to phosphate ratio (except that in RV01 (08) and RV01 (09) this ratio was modified to 4:1 or 16:1). A 2 mL working solution of RNA (or, for RV01(10), DNA) was also prepared from a stock solution of ~1 µg/µL in 100 mM citrate buffer (pH 6). Three 20 mL glass vials (with stir bars) were rinsed with RNase Away solution (Molecular BioProducts) and washed with plenty of MilliQ water before use to decontaminate the vials of RNases. One of the vials was used for the RNA working solution and the others for collecting the lipid and RNA mixes (as described later). The working lipid and RNA solutions were heated at 37° C. for 10 min before being loaded into 3 cc syringes. 2 mL of citrate buffer (pH 6) was loaded in another 3 cc syringe. Syringes containing RNA and the lipids were connected to a T mixer (PEEK™ 500 µm ID junction) using FEP tubing. The outlet from the T mixer was also FEP tubing. The third syringe containing the citrate buffer was connected to a separate piece of FEP tubing. All syringes were then driven at a flow rate of 7 mL/min using a syringe pump. The tube outlets were positioned to collect the mixtures in a 20 mL glass vial (while stirring). The stir bar was taken out and the ethanol/aqueous solution was allowed to equilibrate to room temperature for 1 hour. Then the mixture was loaded in a 5 cc syringe, which was fitted to a piece of FEP tubing and in another 5 cc syringe with equal length of FEP tubing, an equal volume of 100 mM citrate buffer (pH 6) was loaded. The two syringes were driven at 7 mL/min flow rate using a syringe pump and the final mixture collected in a 20 mL glass vial (while stirring). Next, liposomes were concentrated to 2 mL and dialyzed against 10-15 volumes of 1×PBS using TFF before recovering the final product. The TFF system and hollow fiber filtration membranes were purchased from Spectrum Labs and were used according to the manufacturer's guidelines. Polyethersulfone (PES) hollow fiber filtration membranes (part number P-C1-100E-100-01N) with a 100 kD pore size cutoff and 20 cm² surface area were used. For in vitro and in vivo experiments, formulations were diluted to the required RNA concentration with 1×PBS.

Preparation method (B) differed in two ways from method (A). Firstly, after collection in the 20 mL glass vial but before TFF concentration, the mixture was passed through a Mustang Q membrane (an anion-exchange support that binds and removes anionic molecules, obtained from Pall Corporation, Ann Arbor, Mich., USA). This membrane was first washed with 4 mL of 1 M NaOH, 4 mL of 1 M NaCl and 10 mL of 100 mM citrate buffer (pH 6) in turn, and liposomes were warmed for 10 min at 37° C. before being filtered. Secondly, the hollow fiber filtration membrane was Polysulfone (part number P/N: X1AB-100-20P).

The Z average particle diameter, polydispersity index and encapsulation efficiency of the liposomes were as follows:

| RV | Zav (nm) | pdI | % encapsulation | Preparation |
|---|---|---|---|---|
| RV01 (10) | 158.6 | 0.088 | 90.7 | (A) |
| RV01 (08) | 156.8 | 0.144 | 88.6 | (A) |
| RV01 (05) | 136.5 | 0.136 | 99 | (B) |
| RV01 (09) | 153.2 | 0.067 | 76.7 | (A) |
| RV05 (01) | 148 | 0.127 | 80.6 | (A) |
| RV05 (02) | 177.2 | 0.136 | 72.4 | (A) |
| RV01 (10) | 134.7 | 0.147 | 87.8 * | (A) |
| RV13 (02) | 128.3 | 0.179 | 97 | (A) |

* For this RV01(10) formulation the nucleic acid was DNA not RNA

Serum was collected for antibody analysis on days 14, 36 and 49. Spleens were harvested from mice at day 49 for T cell analysis.

F-specific serum IgG titers (GMT) were as follows:

| RV | Day 14 | Day 36 |
|---|---|---|
| Naked DNA plasmid | 439 | 6712 |
| Naked A317 RNA | 78 | 2291 |
| RV01 (10) | 3020 | 26170 |
| RV01 (08) | 2326 | 9720 |
| RV01 (05) | 5352 | 54907 |
| RV01 (09) | 4428 | 51316 |
| RV05 (01) | 1356 | 5346 |
| RV05 (02) | 961 | 6915 |
| RV01 (10) DNA | 5 | 13 |
| RV13 (02) | 644 | 3616 |

The proportion of T cells which are cytokine-positive and specific for RSV F51-66 peptide are as follows, showing only figures which are statistically significantly above zero:

| RV | CD4+CD8− | | | | CD4−CD8+ | | | |
|---|---|---|---|---|---|---|---|---|
| | IFNγ | IL2 | IL5 | TNFα | IFNγ | IL2 | IL5 | TNFα |
| Naked DNA plasmid | 0.04 | 0.07 | | 0.10 | 0.57 | 0.29 | | 0.66 |
| Naked A317 RNA | 0.04 | 0.05 | | 0.08 | 0.57 | 0.23 | | 0.67 |
| RV01 (10) | 0.07 | 0.10 | | 0.13 | 1.30 | 0.59 | | 1.32 |
| RV01 (08) | 0.02 | 0.04 | | 0.06 | 0.46 | 0.30 | | 0.51 |
| RV01 (05) | 0.08 | 0.12 | | 0.15 | 1.90 | 0.68 | | 1.94 |
| RV01 (09) | 0.06 | 0.08 | | 0.09 | 1.62 | 0.67 | | 1.71 |
| RV05 (01) | | | | | 0.06 | 0.04 | | 0.19 |
| RV05 (02) | 0.05 | 0.07 | | 0.11 | 0.64 | 0.35 | | 0.69 |
| RV01 (10) DNA | | | | 0.03 | | | | 0.08 |
| RV13 (02) | 0.03 | 0.04 | | 0.06 | 1.15 | 0.41 | | 1.18 |

Thus the liposome formulations significantly enhanced immunogenicity relative to the naked RNA controls, as determined by increased F-specific IgG titers and T cell frequencies. Plasmid DNA formulated with liposomes, or delivered naked using electroporation, was significantly less immunogenic than liposome-formulated self-replicating RNA.

The RV01 and RV05 RNA vaccines were more immunogenic than the RV13 (DOTAP) vaccine. These formulations had comparable physical characteristics and were formulated with the same self-replicating RNA, but they contain different cationic lipids. RV01 and RV05 both have a tertiary amine in the headgroup with a pKa of about 5.8, and also include unsaturated alkyl tails. RV13 has unsaturated alkyl tails but its headgroup has a quaternary amine and is very strongly cationic. These results suggest that lipids with tertiary amines with pKas in the range 5.0 to 7.6 are superior to lipids such as DOTAP, which are strongly cationic, when used in a liposome delivery system for RNA.

Further Alternatives to DLinDMA

Figure 17:
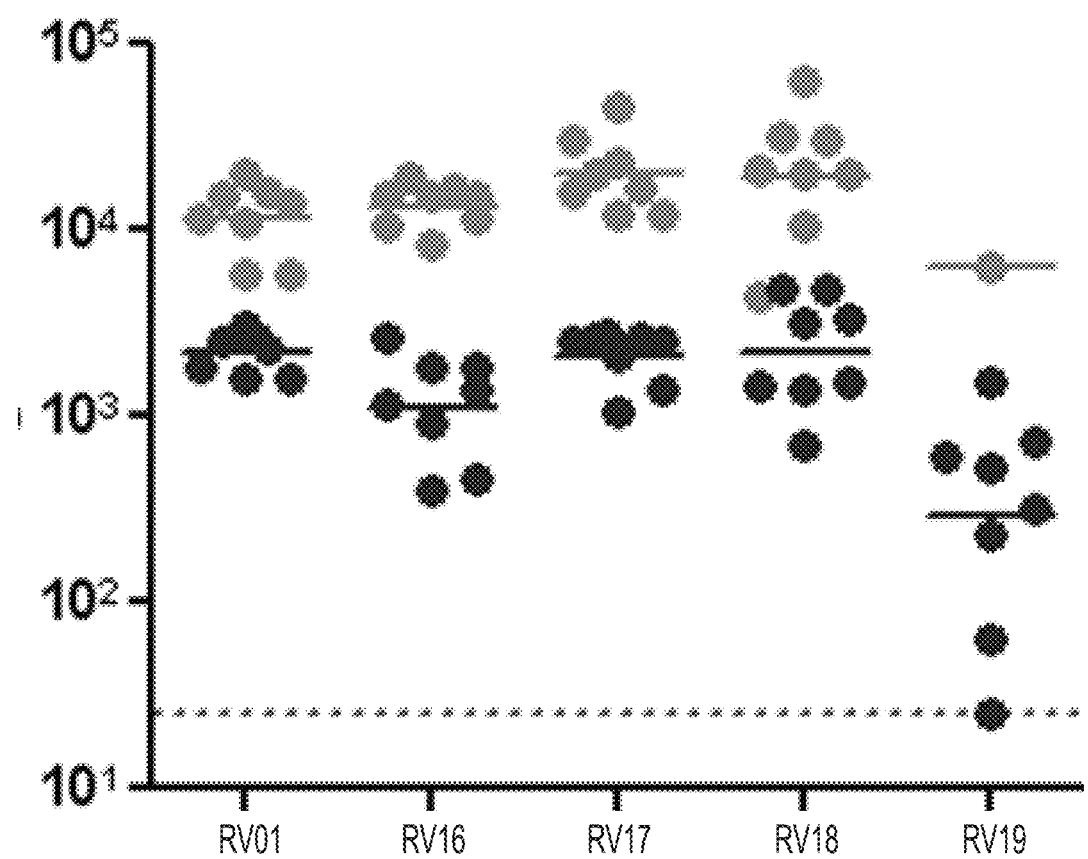
FIG. 17 shows total IgG titers after replicon delivery in liposomes using, from left to right, RV01, RV16, RV17, RV18 or RV19. Bars show means. The upper bar in each case is 2wp2 (i.e. 2 weeks after second dose), whereas the lower bar is 2wp1.

The cationic lipid in RV01 liposomes (DLinDMA) was replaced by RV16, RV17, RV18 or RV19. Total IgG titers are shown in FIG. 17. The lowest results are seen with RV19 i.e. the DOTMA quaternary amine.

BHK Expression

Liposomes with different lipids were incubated with BHK cells overnight and assessed for protein expression potency. From a baseline with RV05 lipid expression could be increased 18× by adding 10% 1,2-diphytanoyl-sn-glycero-3-phosphoethanolamine (DPyPE) to the liposome, 10× by adding 10% 18:2 (cis) phosphatidylcholine, and 900× by instead using RV01.

RSV Immunogenicity in Different Mouse Strains

Replicon "vA142" encodes the full-length wild type surface fusion (F) glycoprotein of RSV but with the fusion peptide deleted, and the 3' end is formed by ribozyme-mediated cleavage. It was tested in three different mouse strains.

BALB/c mice were given bilateral intramuscular vaccinations (50 μL per leg) on days 0 and 22. Animals were divided into 8 test groups (5 animals per group) and a naïve control (2 animals):

Group 1 were given naked replicon (1 μg).
Group 2 were given 1 μg replicon delivered in liposomes "RV01(37)" with 40% DlinDMA, 10% DSPC, 48% Chol, 2% PEG-conjugated DMG.
Group 3 were given the same as group 2, but at 0.1 μg RNA.
Group 4 were given 1 μg replicon in "RV17(10)" liposomes (40% RV17 (see above), 10% DSPC, 49.5% cholesterol, 0.5% PEG-DMG).
Group 5 were 1 μg replicon in "RV05(11)" liposomes (40% RV07 lipid, 30% 18:2 PE (DLoPE, 28% cholesterol, 2% PEG-DMG).
Group 6 were given 0.1 μg replicon in "RV17(10)" liposomes.
Group 7 were given 5 μg RSV-F subunit protein adjuvanted with aluminium hydroxide.
Group 8 were a naïve control (2 animals)

Sera were collected for antibody analysis on days 14, 35 and 49. F-specific serum IgG GMTs were:

| Day | 1 | 2 | 3 | 4 | 5 | 6 | 7 | 8 |
|---|---|---|---|---|---|---|---|---|
| 14 | 82 | 2463 | 1789 | 2496 | 1171 | 1295 | 1293 | 5 |
| 35 | 1538 | 34181 | 25605 | 23579 | 13718 | 8887 | 73809 | 5 |

At day 35 F-specific IgG1 and IgG2a titers (GMT) were as follows:

| IgG | 1 | 2 | 3 | 4 | 5 | 6 | 7 |
|---|---|---|---|---|---|---|---|
| IgG1 | 94 | 6238 | 4836 | 7425 | 8288 | 1817 | 78604 |
| IgG2a | 5386 | 77064 | 59084 | 33749 | 14437 | 17624 | 24 |

RSV serum neutralizing antibody titers at days 35 and 49 were as follows (data are 60% plaque reduction neutralization titers of pools of 2-5 mice, 1 pool per group):

| Day | 1 | 2 | 3 | 4 | 5 | 6 | 7 | 8 |
|---|---|---|---|---|---|---|---|---|
| 35 | <20 | 143 | 20 | 101 | 32 | 30 | 111 | <20 |
| 49 | <20 | 139 | <20 | 83 | 41 | 32 | 1009 | <20 |

Spleens were harvested at day 49 for T cell analysis. Average net F-specific cytokine-positive T cell frequencies (CD4+ or CD8+) were as follows, showing only figures which were statistically significantly above zero (specific for RSV peptides F51-66, F164-178, F309-323 for CD4+, or for peptides F85-93 and F249-258 for CD8+):

| Group | CD4+CD8− | | | | CD4−CD8+ | | | |
|---|---|---|---|---|---|---|---|---|
| | IFNγ | IL2 | IL5 | TNFα | IFNγ | IL2 | IL5 | TNFα |
| 1 | 0.03 | 0.06 | | 0.08 | 0.47 | 0.29 | | 0.48 |
| 2 | 0.05 | 0.10 | | 0.08 | 1.35 | 0.52 | | 1.11 |
| 3 | 0.03 | 0.07 | | 0.06 | 0.64 | 0.31 | | 0.61 |
| 4 | 0.05 | 0.09 | | 0.07 | 1.17 | 0.65 | | 1.09 |
| 5 | 0.03 | 0.08 | | 0.07 | 0.65 | 0.28 | | 0.58 |
| 6 | 0.05 | 0.07 | | 0.07 | 0.74 | 0.36 | | 0.66 |
| 7 | | 0.02 | | | 0.04 | 0.04 | | |
| 8 | | | | | | | | |

C57BL/6 mice were immunised in the same way, but a 9th group received VRPs ($1\times10^6$ IU) expressing the full-length wild-type surface fusion glycoprotein of RSV (fusion peptide deletion).

Sera were collected for antibody analysis on days 14, 35 & 49. F-specific IgG titers (GMT) were:

| Day | 1 | 2 | 3 | 4 | 5 | 6 | 7 | 8 | 9 |
|---|---|---|---|---|---|---|---|---|---|
| 14 | 1140 | 2133 | 1026 | 2792 | 3045 | 1330 | 2975 | 5 | 1101 |
| 35 | 1721 | 5532 | 3184 | 3882 | 9525 | 2409 | 39251 | 5 | 12139 |

At day 35 F-specific IgG1 and IgG2a titers (GMT) were as follows:

| IgG | 1 | 2 | 3 | 4 | 5 | 6 | 7 | 8 |
|---|---|---|---|---|---|---|---|---|
| IgG1 | 66 | 247 | 14 | 328 | 468 | 92 | 56258 | 79 |
| IgG2a | 2170 | 7685 | 5055 | 6161 | 1573 | 2944 | 35 | 14229 |

RSV serum neutralizing antibody titers at days 35 and 49 were as follows (data are 60% plaque reduction neutralization titers of pools of 2-5 mice, 1 pool per group):

| Day | 1 | 2 | 3 | 4 | 5 | 6 | 7 | 8 | 9 |
|---|---|---|---|---|---|---|---|---|---|
| 35 | <20 | 27 | 29 | 22 | 36 | <20 | 28 | <20 | <20 |
| 49 | <20 | 44 | 30 | 23 | 36 | <20 | 33 | <20 | 37 |

Spleens were harvested at day 49 for T cell analysis. Average net F-specific cytokine-positive T cell frequencies (CD8+) were as follows, showing only figures which were statistically significantly above zero (specific for RSV peptides F85-93 and F249-258):

| | CD4-CD8+ | | | |
|---|---|---|---|---|
| Group | IFNγ | IL2 | IL5 | TNFα |
| 1 | 0.42 | 0.13 | | 0.37 |
| 2 | 1.21 | 0.37 | | 1.02 |
| 3 | 1.01 | 0.26 | | 0.77 |
| 4 | 1.26 | 0.23 | | 0.93 |
| 5 | 2.13 | 0.70 | | 1.77 |
| 6 | 0.59 | 0.19 | | 0.49 |
| 7 | 0.10 | 0.05 | | |
| 8 | | | | |
| 9 | 2.83 | 0.72 | | 2.26 |

Nine groups of C3H/HeN mice were immunised in the same way. F-specific IgG titers (GMT) were:

| Day | 1 | 2 | 3 | 4 | 5 | 6 | 7 | 8 | 9 |
|---|---|---|---|---|---|---|---|---|---|
| 14 | 5 | 2049 | 1666 | 1102 | 298 | 984 | 3519 | 5 | 806 |
| 35 | 152 | 27754 | 19008 | 17693 | 3424 | 6100 | 62297 | 5 | 17249 |

At day 35 F-specific IgG1 and IgG2a titers (GMT) were as follows:

| IgG | 1 | 2 | 3 | 4 | 5 | 6 | 7 | 8 |
|---|---|---|---|---|---|---|---|---|
| IgG1 | 5 | 1323 | 170 | 211 | 136 | 34 | 83114 | 189 |
| IgG2a | 302 | 136941 | 78424 | 67385 | 15667 | 27085 | 3800 | 72727 |

RSV serum neutralizing antibody titers at days 35 and 49 were as follows:

| Day | 1 | 2 | 3 | 4 | 5 | 6 | 7 | 8 | 9 |
|---|---|---|---|---|---|---|---|---|---|
| 35 | <20 | 539 | 260 | 65 | 101 | 95 | 443 | <20 | 595 |
| 49 | <20 | 456 | 296 | 35 | 82 | 125 | 1148 | <20 | 387 |

Thus three different lipids (RV01, RV05, RV17; pKa 5.8, 5.85, 6.1) were tested in three different inbred mouse strains. For all 3 strains RV01 was more effective than RV17; for BALB/c and C3H strains RV05 was less effective than either RV01 or RV17, but it was more effective in B6 strain. In all cases, however, the liposomes were more effective than two cationic nanoemulsions which were tested in parallel.

CMV Immunogenicity

RV01 liposomes with DLinDMA as the cationic lipid were used to deliver RNA replicons encoding cytomegalovirus (CMV) glycoproteins. The "vA160" replicon encodes full-length glycoproteins H and L (gH/gL), whereas the "vA322" replicon encodes a soluble form (gHsol/gL). The two proteins are under the control of separate subgenomic promoters in a single replicon; co-administration of two separate vectors, one encoding gH and one encoding gL, did not give good results.

BALB/c mice, 10 per group, were given bilateral intramuscular vaccinations (50 µL per leg) on days 0, 21 and 42 with VRPs expressing gH/gL ($1\times10^6$ IU), VRPs expressing gHsol/gL ($1\times10^6$ IU) and PBS as the controls. Two test groups received 1 µg of the vA160 or vA322 replicon formulated in liposomes (40% DlinDMA, 10% DSPC, 48% Chol, 2% PEG-DMG; made using method (A) as discussed above, but with 150 µg RNA batch size).

The vA160 liposomes had a Zav diameter of 168 nm, a pdI of 0.144, and 87.4% encapsulation. The vA322 liposomes had a Zav diameter of 162 nm, a pdI of 0.131, and 90% encapsulation.

The replicons were able to express two proteins from a single vector.

Sera were collected for immunological analysis on day 63 (3wp3). CMV neutralization titers (the reciprocal of the serum dilution producing a 50% reduction in number of positive virus foci per well, relative to controls) were as follows:

| gH/gL VRP | gHsol/gL VRP | gH/gL liposome | gHsol/gL liposome |
|---|---|---|---|
| 4576 | 2393 | 4240 | 10062 |

RNA expressing either a full-length or a soluble form of the CMV gH/gL complex thus elicited high titers of neutralizing antibodies, as assayed on epithelial cells. The average titers elicited by the liposome-encapsulated RNAs were at least as high as for the corresponding VRPs.

It will be understood that the invention has been described by way of example only and modifications may be made whilst remaining within the scope and spirit of the invention.

REFERENCES

[1] Johanning et al. (1995) *Nucleic Acids Res* 23:1495-1501.
[2] WO2005/121348.
[3] WO2008/137758.
[4] WO2009/086558.
[5] WO2011/076807.
[6] Heyes et al. (2005) *J Controlled Release* 107:276-87.
[7] WO2005/121348.
[8] *Liposomes: Methods and Protocols, Volume 1: Pharmaceutical Nanocarriers: Methods and Protocols*. (ed. Weissig). Humana Press, 2009. ISBN 160327359X.
[9] *Liposome Technology*, volumes I, II & III. (ed. Gregoriadis). Informa Healthcare, 2006.
[10] *Functional Polymer Colloids and Microparticles volume 4 (Microspheres, microcapsules & liposomes)*. (eds. Arshady & Guyot). Citus Books, 2002.
[11] Jeffs et al. (2005) *Pharmaceutical Research* 22 (3):362-372.
[12] WO2005/113782.

[13] WO2011/005799.
[14] El Ouahabi et al. (1996) *FEBS Letts* 380:108-12.
[15] Giuliani et al. (2006) *Proc Natl Acad Sci USA* 103(29): 10834-9.
[16] WO2009/016515.
[17] WO02/34771.
[18] WO2005/032582.
[19] WO2010/119343.
[20] WO2006/110413.
[21] WO2005/111066.
[22] WO2005/002619.
[23] WO2006/138004.
[24] WO2009/109860.
[25] WO02/02606.
[26] WO03/018054.
[27] WO2006/091517.
[28] WO2008/020330.
[29] WO2006/089264.
[30] WO2009/104092.
[31] WO2009/031043.
[32] WO2007/049155.
[33] Gennaro (2000) *Remington: The Science and Practice of Pharmacy.* 20th edition, ISBN: 0683306472.
[34] *Methods In Enzymology* (S. Colowick and N. Kaplan, eds., Academic Press, Inc.)
[35] *Handbook of Experimental Immunology*, Vols. I-IV (D. M. Weir and C. C. Blackwell, eds, 1986, Blackwell Scientific Publications)
[36] Sambrook et al. (2001) *Molecular Cloning: A Laboratory Manual*, 3rd edition (Cold Spring Harbor Laboratory Press).
[37] *Handbook of Surface and Colloidal Chemistry* (Birdi, K. S. ed., CRC Press, 1997)
[38] Ausubel et al. (eds) (2002) *Short protocols in molecular biology,* 5th edition (Current Protocols).
[39] *Molecular Biology Techniques: An Intensive Laboratory Course*, (Ream et al., eds., 1998, Academic Press)
[40] *PCR (Introduction to Biotechniques Series)*, 2nd ed. (Newton & Graham eds., 1997, Springer Verlag)
[41] Yoneyama & Fujita (2007) *Cytokine & Growth Factor Reviews* 18:545-51.
[42] Maurer et al. (2001) *Biophysical Journal,* 80: 2310-2326.
[43] Perri et al. (2003) *J Virol* 77:10394-10403.
[44] Iavarone et al. (2011) *J Immunol* 186; 4213-22.
[45] WO2011/057020.

The invention claimed is:

1. A method of eliciting an immune response against an immunogen in a subject, the method comprising:
administering to the subject an immunologically effective unit dose of a formulation comprising:
ribonucleic acid (RNA) molecules comprising a sequence that encodes the immunogen, wherein the immunogen comprises a respiratory syncytial virus immunogen, an Epstein-Barr virus immunogen, a cytomegalovirus immunogen, a coronavirus spike polypeptide immunogen, an influenza virus A immunogen, a *Varicella zoster* virus immunogen, or a flavivirus immunogen; and
lipids comprising a tertiary amine cationic lipid, a polyethylene glycol-conjugated (PEG-conjugated) lipid, and cholesterol;
wherein the lipids encapsulate at least half of the RNA molecules; and
wherein the immune response against the immunogen comprises an antibody response against the immunogen.

2. The method of claim 1, wherein the subject is a human subject.

3. The method of claim 2, wherein the unit dose comprises from 10 μg to 100 μg of the RNA molecules in 0.1 mL to 1 mL of the formulation.

4. The method of claim 3, wherein the lipids comprise from 40 mole % to 60 mole % tertiary amine cationic lipid.

5. The method of claim 3, wherein the lipids comprise from 35 mole % to 50 mole % cholesterol.

6. The method of claim 2, wherein the PEG-conjugated lipid comprises a PEG that has a molecular weight of 2000 Daltons.

7. The method of claim 2, wherein the PEG-conjugated lipid comprises 1,2-dimyristoyl-rac-glycero-3-methoxy-polyethylene glycol.

8. The method of claim 2, wherein the RNA molecules further comprise a 3' poly(adenosine monophosphate) (poly (A)) tail.

9. The method of claim 8, wherein the RNA molecules further comprise a 5' cap and a 5' first ribonucleotide and wherein the 5' cap is linked 5'-to-5' to the 5' first ribonucleotide.

10. The method of claim 9, wherein the 5' first ribonucleotide comprises a 2'-methylated ribose.

11. The method of claim 10, wherein the lipids comprise from 35 mole % to 50 mole % cholesterol.

12. The method of claim 10, wherein the lipids comprise from 40 mole % to 60 mole % tertiary amine cationic lipid.

13. The method of claim 10, wherein the tertiary amine cationic lipid has a $pK_a$ from 6.07 to 7.6; whereby the $pK_a$ is determined at standard temperature and pressure by:

(1) admixing 400 μL of 2 mM of the tertiary amine cationic lipid that is in ethanol and 800 μL of 0.3 mM of fluorescent probe 6-(p-toluidino)-2-naphthalene-sulfonic acid (TNS), which is in 90 volume % ethanol and 10 volume % methanol, thereby obtaining a lipid/TNS mixture;

(2) admixing 7.5 μL of the lipid/TNS mixture and 242.5 μL of a first buffer consisting essentially of a sodium salt buffer consisting of 20 mM sodium phosphate, 25 mM sodium citrate, 20 mM sodium acetate, and 150 mM sodium chloride, wherein the first buffer has a pH from 4.44 to 4.52, which has been adjusted with 12N hydrochloric acid or 6N sodium hydroxide, thereby obtaining a first mixture, and dispensing 100 μL of the first mixture in a first well of a 96-well plate, which has a clear bottom;

(3) admixing 7.5 μL of the lipid/TNS mixture and 242.5 μL of a second buffer consisting essentially of the sodium salt buffer, wherein the second buffer has a pH of 5.27, which has been adjusted with 12N hydrochloric acid or 6N sodium hydroxide, thereby obtaining a second mixture, and dispensing 100 μL of the second mixture in a second well of the 96-well plate;

(4) admixing 7.5 μL of the lipid/TNS mixture and 242.5 μL of a third buffer consisting essentially of the sodium salt buffer, wherein the third buffer has a pH from 6.15 to 6.21, which has been adjusted with 12N hydrochloric acid or 6N sodium hydroxide, thereby obtaining a third mixture, and dispensing 100 μL of the third mixture in a third well of the 96-well plate;

(5) admixing 7.5 μL of the lipid/TNS mixture and 242.5 μL of a fourth buffer consisting essentially of the sodium salt buffer, wherein the fourth buffer has a pH of 6.57, which has been adjusted with 12N hydrochloric acid or 6N sodium hydroxide, thereby obtaining a fourth mixture, and dispensing 100 μL of the fourth mixture in a fourth well of the 96-well plate;

(6) admixing 7.5 μL of the lipid/TNS mixture and 242.5 μL of a fifth buffer consisting essentially of the sodium salt buffer, wherein the fifth buffer has a pH from 7.10 to 7.20, which has been adjusted with 12N hydrochloric acid or 6N sodium hydroxide, thereby obtaining a fifth mixture, and dispensing 100 μL of the fifth mixture in a fifth well of the 96-well plate;

(7) admixing 7.5 μL of the lipid/TNS mixture and 242.5 μL of a sixth buffer consisting essentially of the sodium salt buffer, wherein the sixth buffer has a pH from 7.72 to 7.80, which has been adjusted with 12N hydrochloric acid or 6N sodium hydroxide, thereby obtaining a sixth mixture, and dispensing 100 μL of the sixth mixture in a sixth well of the 96-well plate;

(8) admixing 7.5 μL of the lipid/TNS mixture and 242.5 μL of a seventh buffer consisting essentially of the sodium salt buffer, wherein the seventh buffer has a pH from 8.27 to 8.33, which has been adjusted with 12N hydrochloric acid or 6N sodium hydroxide, thereby obtaining a seventh mixture, and dispensing 100 μL of the seventh mixture in a seventh well of the 96-well plate;

(9) admixing 7.5 μL of the lipid/TNS mixture and 242.5 μL of an eighth buffer consisting essentially of the sodium salt buffer, wherein the eighth buffer has a pH from 10.47 to 11.12, which has been adjusted with 12N hydrochloric acid or 6N sodium hydroxide, thereby obtaining an eighth mixture, and dispensing 100 μL of the eighth mixture in an eighth well of the 96-well plate;

(10) measuring the fluorescence at a wavelength of 431 nm with an excitation wavelength of 322 nm and a cut-off below a wavelength of 420 nm of each of the first through eighth wells and an empty well of the 96-well plate, thereby obtaining a measured fluorescence for each of the empty well and the first through eighth wells;

(11) subtracting the measured fluorescence of the empty well from each of the measured fluorescences of the first through eighth wells, thereby obtaining a blank-subtracted fluorescence for each of the first through eighth mixtures;

(12) normalizing each of the blank-subtracted fluorescences of the first through eighth mixtures to the blank-subtracted fluorescence of the first mixture, thereby obtaining a relative fluorescence for each of the first through eighth mixtures, the relative fluorescence being 1 for the first mixture;

(13) obtaining a line of best fit of the pHs of the first through eighth buffers versus the respective relative fluorescences of the first through eighth mixtures; and

(14) determining the $pK_a$ as the pH on the line of best fit at which a relative fluorescence of 0.5 is obtained.

14. The method of claim 13, wherein the lipids comprise from 40 mole % to 60 mole % tertiary amine cationic lipid.

15. The method of claim 13, wherein the lipids comprise from 35 mole % to 50 mole % cholesterol.

16. The method of claim 13, wherein the $pK_a$ is from 6.07 to 6.8.

17. The method of claim 2, wherein the lipids further comprise 1,2-di stearoyl-sn-glycero-3-phosphocholine.

18. The method of claim 17, wherein the PEG-conjugated lipid comprises a PEG that has a molecular weight of 2000 Daltons.

19. The method of claim 17, wherein the RNA molecules further comprise a 3' poly(A) tail.

20. The method of claim 19, wherein the RNA molecules further comprise a 5' cap and a 5' first ribonucleotide and wherein the 5' cap is linked 5'-to-5' to the 5' first ribonucleotide.

21. The method of claim 20, wherein the 5' first ribonucleotide comprises a 2'-methylated ribose.

22. The method of claim 21, wherein the lipids comprise from 35 mole % to 50 mole % cholesterol.

23. The method of claim 21, wherein the tertiary amine cationic lipid has a $pK_a$ from 6.07 to 7.6; whereby the $pK_a$ is determined by:

(1) admixing 400 μL of 2 mM of the tertiary amine cationic lipid that is in ethanol and 800 μL of 0.3 mM of TNS, which is in 90 volume % ethanol and 10 volume % methanol, thereby obtaining a lipid/TNS mixture;

(2) admixing 7.5 μL of the lipid/TNS mixture and 242.5 μL of a first buffer consisting essentially of a sodium salt buffer consisting of 20 mM sodium phosphate, 25 mM sodium citrate, 20 mM sodium acetate, and 150 mM sodium chloride, wherein the first buffer has a pH from 4.44 to 4.52, which has been adjusted with 12N hydrochloric acid or 6N sodium hydroxide, thereby obtaining a first mixture, and dispensing 100 μL of the first mixture in a first well of a 96-well plate, which has a clear bottom;

(3) admixing 7.5 μL of the lipid/TNS mixture and 242.5 μL of a second buffer consisting essentially of the sodium salt buffer, wherein the second buffer has a pH of 5.27, which has been adjusted with 12N hydrochloric acid or 6N sodium hydroxide, thereby obtaining a second mixture, and dispensing 100 μL of the second mixture in a second well of the 96-well plate;

(4) admixing 7.5 μL of the lipid/TNS mixture and 242.5 μL of a third buffer consisting essentially of the sodium salt buffer, wherein the third buffer has a pH of from 6.15 to 6.21, which has been adjusted with 12N hydrochloric acid or 6N sodium hydroxide, thereby obtaining a third mixture, and dispensing 100 μL of the third mixture in a third well of the 96-well plate;

(5) admixing 7.5 μL of the lipid/TNS mixture and 242.5 μL of a fourth buffer consisting essentially of the sodium salt buffer, wherein the fourth buffer has a pH of 6.57, which has been adjusted with 12N hydrochloric acid or 6N sodium hydroxide, thereby obtaining a fourth mixture, and dispensing 100 μL of the fourth mixture in a fourth well of the 96-well plate;

(6) admixing 7.5 μL of the lipid/TNS mixture and 242.5 μL of a fifth buffer consisting essentially of the sodium salt buffer, wherein the fifth buffer has a pH of from 7.10 to 7.20, which has been adjusted with 12N hydrochloric acid or 6N sodium hydroxide, thereby obtaining a fifth mixture, and dispensing 100 μL of the fifth mixture in a fifth well of the 96-well plate;

(7) admixing 7.5 μL of the lipid/TNS mixture and 242.5 μL of a sixth buffer consisting essentially of the sodium salt buffer, wherein the sixth buffer has a pH of from 7.72 to 7.80, which has been adjusted with 12N hydrochloric acid or 6N sodium hydroxide, thereby obtaining a sixth mixture, and dispensing 100 μL of the sixth mixture in a sixth well of the 96-well plate;

(8) admixing 7.5 µL of the lipid/TNS mixture and 242.5 µL of a seventh buffer consisting essentially of the sodium salt buffer, wherein the seventh buffer has a pH of from 8.27 to 8.33, which has been adjusted with 12N hydrochloric acid or 6N sodium hydroxide, thereby obtaining a seventh mixture, and dispensing 100 µL of the seventh mixture in a seventh well of the 96-well plate;

(9) admixing 7.5 µL of the lipid/TNS mixture and 242.5 µL of an eighth buffer consisting essentially of the sodium salt buffer, wherein the eighth buffer has a pH of from 10.47 to 11.12, which has been adjusted with 12N hydrochloric acid or 6N sodium hydroxide, thereby obtaining an eighth mixture, and dispensing 100 µL of the eighth mixture in an eighth well of the 96-well plate;

(10) measuring the fluorescence at a wavelength of 431 nm with an excitation wavelength of 322 nm and a cut-off below a wavelength of 420 nm of each of each of the first through eighth wells and an empty well of the 96-well plate, thereby obtaining a measured fluorescence for each of the empty well and the first through eighth wells;

(11) subtracting the measured fluorescence of the empty well from each of the measured fluorescences of the first through eighth wells, thereby obtaining a blank-subtracted fluorescence for each of the first through eighth mixtures;

(12) normalizing each of the blank-subtracted fluorescences of the first through eighth mixtures to the blank-subtracted fluorescence of the first mixture, thereby obtaining a relative fluorescence for each of the first through eighth mixtures, the relative fluorescence being 1 for the first mixture;

(13) obtaining a line of best fit of the pHs of the first through eighth buffers versus the respective relative fluorescences of the plurality of the first through eighth mixtures; and

(14) determining the $pK_a$ as the pH on the line of best fit at which a relative fluorescence of 0.5 is obtained.

24. The method of claim 23, wherein the $pK_a$ is from 6.07 to 6.8.

25. The method of claim 24, wherein the lipids comprise from 40 mole % to 60 mole % tertiary amine cationic lipid.

26. The method of claim 24, wherein the immune response against the immunogen further comprises a cell-mediated immune response against the immunogen.

27. The method of claim 24, wherein the lipids comprise from 35 mole % to 50 mole % cholesterol.

28. The method of claim 23, wherein the lipids comprise from 40 mole % to 60 mole % tertiary amine cationic lipid.

29. The method of claim 23, wherein the lipids comprise from 35 mole % to 50 mole % cholesterol.

30. The method of claim 21, wherein the lipids comprise from 40 mole % to 60 mole % tertiary amine cationic lipid.

31. The method of claim 17, wherein the lipids comprise from 40 mole % to 60 mole % tertiary amine cationic lipid.

32. The method of claim 17, wherein the lipids comprise from 35 mole % to 50 mole % cholesterol.

33. The method of claim 1, wherein the RNA molecules further comprise a sequence that encodes a replicase, and wherein the RNA molecules are self-replicating RNA molecules.

34. The method of claim 1, wherein the immune response against the immunogen further comprises a cell-mediated immune response against the immunogen.

35. The method of claim 1, wherein the lipids comprise from 40 mole % to 60 mole % tertiary amine cationic lipid.

36. The method of claim 1, wherein the lipids comprise from 35 mole % to 50 mole % cholesterol.

37. A method of eliciting an immune response against an immunogen in a subject, the method comprising:
   administering to the subject an immunologically effective unit dose of a formulation comprising:
      ribonucleic acid molecules comprising a sequence that encodes the immunogen, wherein the immunogen comprises a respiratory syncytial virus immunogen, an Epstein-Barr virus immunogen, a cytomegalovirus immunogen, a coronavirus spike polypeptide immunogen, an influenza virus A immunogen, a *Varicella zoster* virus immunogen, or a flavivirus immunogen; and
      lipids comprising a tertiary amine cationic lipid, a polyethylene glycol-conjugated lipid, and cholesterol;
   wherein the tertiary amine cationic lipid is not 1,2-dilinoleyloxy-N,N-dimethyl-3-aminopropane;
   wherein the lipids encapsulate at least half of the RNA molecules; and
   wherein the immune response against the immunogen comprises an antibody response against the immunogen.

* * * * *